US011807875B2

(12) United States Patent
Ralph et al.

(10) Patent No.: US 11,807,875 B2
(45) Date of Patent: Nov. 7, 2023

(54) FERULOYL-COA:MONOLIGNOL TRANSFERASES

(71) Applicant: WISCONSIN ALUMNI RESEARCH FOUNDATION, Madison, WI (US)

(72) Inventors: John Ralph, Madison, WI (US); Steven D. Karlen, Madison, WI (US); Rebecca Anne Smith, Madison, WI (US); Brian Fox, Madison, WI (US); Emily Beebe, Stoughton, WI (US); Craig Bingman, Fitchburg, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 90 days.

(21) Appl. No.: 17/107,024

(22) Filed: Nov. 30, 2020

(65) Prior Publication Data

US 2021/0207104 A1    Jul. 8, 2021

Related U.S. Application Data

(62) Division of application No. 15/945,463, filed on Apr. 4, 2018, now Pat. No. 10,883,089.

(60) Provisional application No. 62/481,281, filed on Apr. 4, 2017.

(51) Int. Cl.
*C12N 15/82*    (2006.01)
*C12N 9/10*    (2006.01)

(52) U.S. Cl.
CPC ....... *C12N 9/1029* (2013.01); *C12N 15/8255* (2013.01)

(58) Field of Classification Search
None
See application file for complete search history.

(56) References Cited

U.S. PATENT DOCUMENTS

| | | | |
|---|---|---|---|
| 4,490,838 A | 12/1984 | Akira et al. | |
| 5,258,300 A | 11/1993 | Glassman et al. | |
| 5,384,253 A | 1/1995 | Krzyzek et al. | |
| 5,472,869 A | 12/1995 | Krzyzek et al. | |
| 5,489,520 A | 2/1996 | Adams et al. | |
| 5,538,877 A | 7/1996 | Lundquist et al. | |
| 5,538,880 A | 7/1996 | Lundquist et al. | |
| 5,550,318 A | 8/1996 | Adams et al. | |
| 5,641,673 A | 6/1997 | Brand et al. | |
| 5,985,557 A | 11/1999 | Brow et al. | |
| 6,001,567 A | 12/1999 | Brow et al. | |
| 7,705,215 B1 | 4/2010 | Adams et al. | |
| 8,481,593 B2 | 7/2013 | Okombi et al. | |
| 8,569,465 B2 | 10/2013 | Ralph et al. | |
| 9,089,499 B2 | 7/2015 | Okombi et al. | |
| 9,428,763 B2 | 8/2016 | Sanz Molinero | |
| 9,441,235 B2 | 9/2016 | Wilkerson et al. | |
| 9,487,794 B2 | 11/2016 | Wilkerson et al. | |
| 9,493,783 B2 | 11/2016 | Wilkerson et al. | |
| 2006/0159283 A1 | 7/2006 | Alexandrov et al. | |
| 2007/0183996 A1 | 8/2007 | Okombi et al. | |
| 2007/0283460 A9 | 12/2007 | Liu et al. | |
| 2008/0112245 A1 | 5/2008 | Ostermayr et al. | |
| 2011/0237551 A1 | 9/2011 | Okombi et al. | |
| 2013/0272983 A1 | 10/2013 | Okombi et al. | |
| 2015/0020234 A1 | 1/2015 | Wilkerson et al. | |
| 2015/0307892 A1 | 10/2015 | Bartley et al. | |
| 2015/0376640 A1 | 12/2015 | Shoresh et al. | |
| 2016/0046955 A1 | 2/2016 | Wilkerson et al. | |
| 2017/0218004 A1 | 8/2017 | Wilkerson et al. | |
| 2018/0298353 A1 | 10/2018 | Beebe et al. | |

FOREIGN PATENT DOCUMENTS

| | | | | |
|---|---|---|---|---|
| EP | 0 154 204 B1 | 2/1985 | | |
| EP | 0 218 571 A2 | 4/1987 | | |
| EP | 321 201 A2 | 6/1989 | | |
| EP | 0 604 662 A1 | 6/1994 | | |
| EP | 0 672 752 A1 | 9/1995 | | |
| WO | WO 1995/06128 A2 | 3/1995 | | |
| WO | WO 2012/012698 A1 | 1/2012 | | |
| WO | WO 2012/012741 A1 | 1/2012 | | |
| WO | WO-2012012698 A1 * | 1/2012 | ............... | C07G 1/00 |
| WO | WO 2013/052660 A1 | 4/2013 | | |
| WO | WO 2013/090814 A3 | 6/2013 | | |
| WO | WO-2014100742 A2 * | 6/2014 | ......... | C12N 15/8246 |

OTHER PUBLICATIONS

Wells (Biochemistry29:8509-8517,1990).*
Guo et al. (PNAS,101:9205-9210,2004).*
Ngo et al.,(TheProteinFoldingProblemandTertiaryStructurePrediction, K.Merz.,and S.LeGrand(eds.) pp. 492-495,1994).*
Thornton et al.(NaturestructuralBiology,structura lgenomics supplement, Nov. 2000).*
Keskin et al.(ProteinScience,13:1043-1055,2004).*
Doerks et al.,(TIG,14:248-250,1998).*
Smith et al.(NatureBiotechnology,15:1222-1223,1997).*
Bork et al.(TIG,12:425-427,1996).*
McConnell et al.(Nature,411:709-713,2001).*
Hanzawa et al.(PNAS,102:7748-7753,2005).*
Wishart et al.(JBC,270:26782-26785,1995).*
Nishimura et al.(PlantCellPhysiol.,41(5):583-590,2000).*
Yang et al.(PNAS,98:11438-11443,2001).*
Paterson et al. (NCBI, GenBank Sequence Accession No. XP_002441966.1, Published Jul. 13, 2009).*

(Continued)

*Primary Examiner* — Vinod Kumar
(74) *Attorney, Agent, or Firm* — Daniel A. Blasiole; DeWitt LLP

(57) ABSTRACT

The invention relates to feruloyl-CoA:monolignol transferase enzymes and nucleic acids encoding the feruloyl-CoA:monolignol transferase enzymes. The enzymes and/or the nucleic acids enable incorporation of monolignol ferulates into the lignin of plants. The monolignol ferulates include, for example, p-coumaryl ferulate, coniferyl ferulate, and/or sinapyl ferulate.

11 Claims, 17 Drawing Sheets

Specification includes a Sequence Listing.

(56) References Cited

OTHER PUBLICATIONS

Alexandrov et al. (NCBI, GenBank Sequence Accession No. EU970537.1, Published Dec. 10, 2008).
Alexandrov et al. Insights into corn genes derived from large-scale cDNA sequencing, *Plant Mol. Biol.*, (2009) 69 (1-2), 179-194.
Alexandrov et al. (GenBank Sequence Accession No. ACG42655; pp. 1-2; 2008).
Altschul S, Gish W, Miller W, Myers E, Lipman D., Basic local alignment search tool. (1990) J Mol Biol 215(3), 403-410.
An. S.M., et al., Binary ti vectors for plant transformation and promoter analysis, *Methods in Enzymology*. (1987) 153:292.
An. S.M., et al., p-Coumaric acid, a constituent of *Sasa quelpaertensis* Nakai, inhibits cellular melanogenesis stimulated by alpha-melanocyte stimulating hormone, *Brit J Dermatol.*, (2008) 159(2), 292-299.
Bell-Lelong et al., Cinnamate-4-hydroxylase expression in *Arabidopsis*: regulation in response to development and the environment, *Plant Physiol.* (1997) 113, 729-738.
Bevan et al., Structure and transcription of the nopaline synthase gene region of T-DNA, *Nucleic Acid Research*. (1983)11:369-385.
Beuerle and Pichersky, Anal. Biochem. 302(2): 305-12 (2001).
Bodini et al., Quorum sensing inhibition activity of garlic extract and p-coumaric acid, *Lett Appl Microbiol*. (2009) 49(5), 551-555.
Boerjan et al., Lignin biosynthesis, *Annual Reviews in Plant Biology* (2003) 54, 519-546.
Bork et al., Go hunting in sequence databases but watch out for the traps, *TIG*, (1996) 12:425-427.
Cabrita et al., Conversion of hydroxycinnamic acids into volatile phenols in a synthetic medium and red wine by Dekkera bruxellensis. *Ciencia e Tecnologia de Alimentos, Campinas*. (2012) 32(1):106-11.
Camacho et al., BLAST+: architecture and applications, *BMC Bioinformatics*. (2009) 10:421.
Cech Science, The chemistry of self-splicing RNA and RNA enzymes, 236:1532-1539 (1987).
Cech. Ann. Rev. Biochem., Self-splicing of group I introns, 59:543-568 (1990).
Cech, Thomas R. Ribozyme engineering. Curr. Opin. Struct. Biol. 2:605-609 (1992) (No Copy Available).
Chandler et al., Two regulatory genes of the maize anthocyanin pathway are homologous: Isolation of B utilizing R genomic sequences, *The Plant Cell*. (1989) 1:1175-1183.
Christou et al., Stable transformation of soybean by electroporation and root formation from transformed callus, *PNAS*. (1987) 84:3962-3966.
Claverie and States, Information Enhancement Methods for Large Scale Sequence Analysis, *Comput. Chem*. (1993) 17:191-201.
Clough et al., Floral dip: A simplified method for *Agrobacterium*-mediated transformation of *Arabidopsis thaliana, Plant Journal* (1998) 16, 735-743.
Coe et al., in *Corn and Corn Improvement*, eds. Sprague, G.F. & Dudley, J.W. (Am. Soc. Agron., Madison, WI), pp. 81-258 (1988) (Book—Copy Not Provided).
Corpet, Multiple sequence alignment with hierarchial clustering, *Nucleic Acids Res*. (1988) 16:10881-90.
Coruzzi et al., Tissue-specific and light-regulated expression of a pea nuclear gene encoding the small subunit of ribulose-1,5-bisphosphate carboxylas, *EMBO J*. (1984) (8):1671-1679).
Couture and Stinchcomb, Anti-gene therapy: the use of ribozymes to inhibit gene function, Trends Genet. 12:510-515 (1996).
Current Protocols in Molecular Biology, Chapters 2 and 19, Ausubel, et al., eds, Greene Publishing and Wiley-Interscience, New York (1995) (Book—Copy Not Provided).
Da Costa Sousa et al., Next-Generation ammonia pretreatment enhances cellulosic biofuel production,. *Energy Environ. Sci*. (2016), 9, 1215-1223.
Dekeyser et al., Transient gene expression in intact and organized rice tissues, *The Plant Cell*. (1990) 2:591-602.

Dellaporta et al., In: *Chromosome Structure and Function: Impact of New Concepts*, 18th Stadler Genetics Symposium, J.P. Gustafson and R. Appels, eds. (New York: Plenum Press) (1988) pp. 263-282.
Doerks et al., Protein annotation: detective work for function prediction, *TIG*, (1998) 14:248-250.
Ebert et al., Identification of an essential upstream element in the nopaline synthase promoter by stable and transient assays, *Proc. Natl. Acad. Sci. USA*. (1987) 84:5745-5749.
Elbashir et al. Duplexes of 21-nucleotide RNAs mediate RNA interference in cultured mammalian cells, (2001) Nature 411:494-498.
Eudes et al., Exploiting members of the BAHD acyltransferase family to synthesize multiple hydroxycinnamate and benzoate conjugates in yeast, *Microb Cell Fact* (2016) 15:198.
Feng and Doolittle, Progressive Sequence Alignment as a Prerequisite to Correct Phylogenetic Trees, *J. Mol. Evol.*, (1987) 25:351-60.
Ferguson et al., Bacterial antimutagenesis by hydroxycinnamic acids from plant cell walls, *Mutation Research-Genetic Toxicology and Environmental Mutagenesis* (2003) 542(1-2), 49-58.
Ferguson et al., Antioxidant and antigenotoxic effects of plant cell wall hydroxycinnamic acids in cultured HT-29 cells. *Molecular Nutrition & Food Research* (2005) 49(6), 585-593.
Fire et al. Potent and specific genetic interference by double-stranded RNA in Caenorhabditis elegans, (1998) Nature 391:806-811.
Gordon Kamm et al., Transformation of maize cells and regeneration of fertile transgenic plants, *The Plant Cell*. (1990) 2:603 618.
Grefen et al., A ubiquitin-10 promoter-based vector set for fluorescent protein tagging facilitates temporal stability and native protein distribution in transient and stable expression studies, *The Plant Journal* (2010) 64, 355-365.
Guo et al. Protein tolerance to random amino acid change, *PNAS* (2004) 101: 9205-9210, 2004.
Grishok et al., Genetic requirements for inheritance of RNAi in C. elegans, Science 287(5462):2494-7 (2000).
Grishok et al. Genes and mechanisms related to RNA interference regulate expression of the small temporal RNAs that control C. elegans developmental timing, (2001) Cell 106:23-34.
Hamilton & Baulcombe, A species of small antisense RNA in posttranscriptional gene silencing in plants, Science 286(5441):950-952 (1999).
Haseloff et al., Simple RNA enzymes with new and highly specific endoribonuclease activities, Nature 334:585-591 (1988).
Hatfield et al., Composition of cell walls isolated from cell types of grain sorghum stems, *J. Sci. Food Agric*. (1999) 79: 891-899.
Hayashimoto et al., A polyethylene glycol-mediated protoplast transformation system for production of fertile transgenic rice plants, *Plant Physiol*. (1990) 93:857-863.
Helm, R. F., Ralph, J., and Hatfield, R.D., Synthesis of feruloylated and p-coumaroylated methyl glycosides. (1992) Carbohydr. Res. 229(1), 183.194.
Henikoff and Henikoff, Amino acid substitution matrices from protein blocks, *Proc. Natl. Acad. Sci. USA* (1989) 89:10915.
Higgins and Sharp, Clustal: a package for performing multiple sequence alignment on a microcomputer, *Gene* (1988) 73:237-44.
Higgins and Sharp, Fast and sensitive multiple sequence alignments on a microcomputer, *Cabios Communications* (1989) 5:151-3.
Hinchee et al., Production of transgenic soybean plants using *Agrobacterium*-mediated DNA transfer, *Bio/Technology*. (1988) 6:915-922.
Holmberg et al., Syringyl methacrylate, a hardwood lignin-based monomer for high-Tg polymeric materials, *ACS Macro Letters* (2016) 5(5), 574-578.
Horsch et al., Somatic embryogenesis from cultured leaf segments of *Zea mays, Science* (1985) 227:1229-1231.
Hsiao & Chiang, Lignins from the Wood of *Aralia bipinnata, Phytochemistry*, (1995) 39: 899-902.
Huang et al., Parallelization of a local similarity algorithm, *Computer Applications in the Biosciences* (1992) 8:155-65.
Hudspeth et al., Structure and expression of the maize gene encoding the phosphoenolpyruvate carboxylase isozyme involved in C4 photosynthesis, *Plant Molecular Biology*. (1989) 12:579-589.

(56) References Cited

OTHER PUBLICATIONS

Ikuta et al., The α-Amylase gene as a marker for gene cloning: Direct screening of recombinant clones, *Bio/Technology* (1990) 8:241-242.
Jefferson, Assaying Chimeric genes in Plants: The GUS Gene Fusion System, *Plant Molecular Biology Reporter* (1987) 5:387-405.
Kaneko et al., Thermotropic liquid-crystalline polymer derived from natural cinnamoyl biomonomers. (2004) *Macromol Rapid Comm* 25(5), 673-677.
Karimi M, Inze D 5 Depicker A. (2002) Gateway vectors for Agrobacterium-mediated plant transformation. Trends in Plant Science 7(5):193-195).
Karlen, S. D. et al., Monolignol ferulate conjugates are naturally incorporated into plant lignins. *Science Advances* (2016) 2 (10), e1600393:1600391-1600399.
Karlen, S.D., Smith, R.A., Kim, H , Padmakshan, D., Bartuce, A., Mobley, J.K., Free, H.C.A., Smith, B.G., Harris, P.J. and Ralph, J. (2017) Highly decorated lignins occur in leaf base cell walls of the Canary Island date palm Phoenix canadensis. Plant Physiology, 175:1058-1067.
Katz et al., Cloning and expression of the tyrosinase gene from *StreptomyKellces antibioticus* in *Streptomyces lividans, J. Gen. Microbiol.* (1983) 129:2703 2714.
Keller et al., Vascular expression of a bean cell wall glycine-rich protein—glucuronidase gene fusion in transgenic tobacco, *EMBO J.* (1989) 8:1309-1314.
Keskin et al. A new, structurally nonredundant, diverse data set of protein-protein interfaces and its implications, *Protein Science*, (2004) 13:1043-1055.
Ketting et al. Mut-7 of C. elegans, required for transposon silencing and RNA interference, is a homolog of Werner syndrome helicase and RNaseD , (1999) Cell 99:133-141.
Kim et al., Solution-state 2D NMR of ball-milled plant cell wall gels in DMSO-$d_6$/pyridine-$d_5$, *Org. Biomol. Chem.* (2010) 8(3), 576-591.
Kim et al., Impact of lignin polymer backbone esters on ionic liquid pretreatment of poplar, *Biotechnology for Biofuels* (2017) 10(1):101.
Kim, H., Ralph, J., and Akiyama, T. (2008) Solution-state 2D NMR of Ball-milled Plant Cell Wall Gels in DMSO-d6. BioEnergy Research 1(1):56-66.
Kumar, P.; Barrett, D. M.; Delwiche, M. J.; Stroeve, P. (2009) Methods for Pretreatment of Lignocellulosic Biomass for Efficient Hydrolysis and Biofuel Production . Industrial A Engineering Chemistry Research 48(8):3713-3729.
Lawton et al., Expression of a soybean β-conclycinin gene under the control of the Cauliflower Mosaic Virus 35S and 19S promoters in transformed petunia tissues, *Plant Molecular Biology.* (1987) 9:315-324.
Li et al., Time-course accumulation of main bioactive components in the rhizome of Ligusticum chuanxiong, *Planta medica* (2006) 72.03: 278-280.
Li and Zhang, Reverse genetics by fast neutron mutagenesis in higher plants, 2002, Fund Integr Genomics 2:254-258.
Lin and Avery, RNA interference. Policing rogue genes, (1999) Nature 402:128-129.
Liu et al., Application of CRISPR/Cas9 in plant biology, *Acta pharm. Sinica B*, (2017) 7(3): 292-302.
Lu, F., and Ralph, J. Facile synthesis of 4-hydroxycinnamyl p-coumarates. (1998) J. Agr. Food Chem. 46(8), 2911-2913.
Lu et al., Derivatization followed by reductive cleavage (DFRC Method), A new method for lignin analysis: protocol for analysis of DFRC monomers, *Journal of Agricultural and Food Chemistry* (1997) 45, 2590-2592.
Lu et al., Detection and determination of p-coumaroylated units in lignins, *Journal of Agricultural and Food Chemistry* (1999) 47, 1988-1992.
Lu et al., Non-degradative dissolution and acetylation of ball-milled plant cell walls; high-resolution solution-state NMR, *Plant J.* (2003) 35(4), 535-544).
Lu, F., Karlen, S.D., Regner, M., Kim, H., Ralph, S.A., Sun, R.C., Kuroda, K.I., Augustin, M.A., Mawson, R., Sabarez, H., Singh, T., Jimenez-Monteon, G., Hill, S., Harris, PL, Boeijan, W., Mansfield, S.D. and Ralph, J. (2015) Naturally p-hydroxybenzoylated lignins in palms. Bioenerg Res. 8:934-952.
Luterbacher et al., Nonenzymatic sugar production from biomass using biomass-derived γ-valerolactone, *Science* (2014) 343.6168:277-280.
Luterbacher et al., Solvent-enabled nonenyzmatic sugar production from biomass for chemical and biological upgrading, *ChemSusChem* (2015) 8.8:1317-1322.
Luterbacher et al., Lignin monomer production integrated into the γ-valerolactone sugar platform, *Energy and Environmental Science* (2015) 8(9), 2657-2663.
Makino et al., Cell-free protein synthesis for functional and structural studies, *Methods in Molecular Biology* (2014) 1091, 161-178.
Mansfield, S.D., Kim, H., Lu, F. and Ralph, J. (2012) Whole plant cell wall characterization using solution-state 2D-NMR. Nature Protocols, 7:1579-1589.
Martinez et al. Single-stranded antisense siRNAs guide target RNA cleavage in RNAi, Cell 110(5):563 (2002).
Marita et al., Identification and suppression of the p-coumaroyl CoA:hydroxycinnamyl alcohol transferase in Zea mays L. Plant J. (2014) 78 (5), 850-864.
McCabe et al., Stable transformation of soybean (glycine max) by particle acceleration, *Bio/Technology* (1988) 6:923-926.
McCallum et al. Targeted screening for induced mutations, (2000) Nat Biotech 18:455.
McCallum et al. Targeting induced local lesions IN genomes (TILLING) for plant functional genomics, (2000) Plant Physiol. 123:439-442.
McConnell et al., Role of Phabulosa and Phavoluta in determining radial patterning in shoots, *Nature* (2001) 411:709-713.
McElroy et al., Isolation of an Efficient Actin Promoter for Use in Rice Transformation, *The Plant Cell* (1990) 2:163-171.
Meinkoth and Wahl, Hybridization of Nucleic Acids immobilized on Solid Supports, *Anal. Biochem.* (1984) 138:267-84.
Mellmer et al. Effects of γ-valerolactone in hydrolysis of lignocellulosic biomass to monosaccharides, *Green Chemistry* (2014) 16.11:4659-4662.
Meyer et al., Lignin monomer composition is determined by the expression of a cytochrome P450-dependent monooxygenase in *Arabidopsis, Proc. Natl. Acad. Sci. USA* (1998) 95(12), 6619-6623.
Montgomery et al. RNA as a target of double-stranded RNA-mediated genetic interference in Caenorhabditis elegans, (1998) Proc. Natl. Acad. Sci. USA. 95:15502-15507.
Murakami et al., The bialaphos biosynthetic genes of Streptomyces hygroscopicus: Molecular cloning and characterization of the gene cluster, *Mol. Gen. Genet.* (1986) 205:42 50.
Nagata et al., Synthesis and characterization of photocrosslinkable biodegradable polymers derived from 4-hydroxycinnamic acid, *Macromol Biosci* (2003) 3(8), 412-419.
Nambudiri et al., Conversion of p-coumarate into caffeate by Streptomyces nigrifaciens. Purification and properties of the hydroxylating enzyme,. *Biochem J.* (1972)130(2):425-33.
Needleman and Wunsch, A General Method Applicable to the Search for Similarities in the Amino Acid Sequence of Two Proteins, *J. Mol. Biol.* (1970) 48:443-53.
Ngo et al., The Protein Folding Problem and Tertiary Structure Prediction, K. Merz., and S. Le Grand (eds.) (1994) pp. 492-495.
Niedz et al., Green fluorescent protein: an in vivo reporter of plant gene expression, *Plant Cell Reports* (1995) 14:403.
Nishimura et al., Over-Expression of Tobacco knotted1-Type Class1 Homeobox Genes Alters Various Leaf Morphology, *Plant Cell Physiol.*, (2000) 41(5):583-590.
Odell et al., Identification of DNA sequences required for activity of the cauliflower mosaic virus 35S promoter, *Nature* (1985) 313:810-812.
Ow et al., Transient and stable expression of the firefly luciferase gene in plant cells and transgenic plants, *Science* (1986) 234:856-859.

(56) References Cited

OTHER PUBLICATIONS

Patterson et al., Hypothetical protein SORBIDRAFT_09g002910 [Sorghum bicolor] (NCBI, Gen Bank Sequence Accession No. XP_002439238.1 Published Jul. 13, 2009).
Paula et al., Lignans from *Ochroma lagopus* Swartz, *Tetrahedron* (1995) 51.45:12453-12462.
PCT International Search Report and Written Opinion, dated Mar. 25, 2020, PCT/US19/60554.
Pearson and Lipman, Improved tools for biological sequence comparison, *Proc. Natl. Acad. Sci. USA* (1988) 85:2444.
Pearson, Using the FASTA Program to Search Protein and DNA Sequence Databases, *Meth. Mol. Biol.* (1994) 24:307-31.
Petrik et al., p-Coumaroyl-CoA:Monolignol Transferase (PMT) acts specifically in the lignin biosynthetic pathway in *Brachypodium distachyon*, *The Plant Journal* (2014) 77 (5), 713-726.
Petrik et al. BdCESA7, BdCESA8, and BdPMT utility promoter Reconstructs for targeted expression to secondary cell-wall-forming cells of grasses, (2016) *Frontiers in Plant Science* (2016) 7, 1-14.
Potrykus et al., Direct gene transfer to cells of a graminaceous monocot, *Mol. Gen. Genet.* 199:183-188 (1985).
Potrykus I., Gene transfer to cereals: an assessment, *Trends Biotech.* (1989) 7:269-273.
Prasher et al., Cloning and expression of the cDNA Coding for Aequorin, a Bioluminescent Calcium-Binding Protein, *Biochem. Biophys. Res. Comm.* (1985) 126:1259-1268.
Ralph et al., Pathway of p-coumaric acid incorporation into maize lignin as revealed by NMR, *J. Am. Chem. Soc.* (1994) 116: 9448-9456.
Ralph et al., Lignins: natural polymers from oxidative coupling of 4-hydroxyphenylpropanoids, *Phytochem. Revs.* (2004) 3(1), 29-60.
Ralph, J., Brunow, G., and Boerjan, W. (2007) Lignins. In: Rose, F., and Osborne, K. (eds). Encyclopedia of Life Sciences, DOI: 10.1002/9780470015902.a0020104, John Wiley & Sons, Ltd., Chichester, UK (Book—Copy Not Provided).
Razzaghi-Asl et al., Antioxidant properties of hydroxycinnamic acids: A review of structure-activity relationships, *Current Medicinal Chemistry* (2013) 20(36), 4436-4450.
Regner, M., Bartuce, A., Padmakshan, D., Ralph, J. and Karlen, S.D. (2018) Reductive cleavage method for quantitation of monolignols and low-abundance monolignol conjugates. ChemSusChem 11:1600-1605.
Rinaldi et al. (2016) Paving the way for lignin valorisation: Recent Advances in Bioengineering, Biorefining and Catalysis. Angew Chem Int Ed Engl. 55(29):8164-8215).
Sambrook et al. (Molecular Cloning: a Laboratory Manual. Second Edition (Cold Spring Harbor, NY: Cold Spring Harbor Press (1989) (Book—Copy Not Provided).
Sambrook et al.,Molecular Cloning: a Laboratory Manual. Third Edition (Cold Spring Harbor, NY: Cold Spring Harbor Press (2000) (Book—Copy Not Provided).
Santoro et al., A high-throughput platform for screening milligram quantities of plant biomass for lignocellulose digestibility, *Bioenergy Research* (2010) 3(1), 93-102.
Sawasaki et al., "Construction of an efficient expression vector for coupled transcription/translation in a wheat germ cell-free system." *Nucleic acids Symposium Series*. (2000) vol. 44. No. 1. Oxford University Press.
Seca et al., Phenolic constituents from the core of kenaf (*Hibiscus cannabinus*), *Phytochemistry* (2001) 56.7:759-767.
Sengupta-Gopalan, C., Developmentally regulated expression of the bean β-phaseolin gene in tobacco seed, *Proc. Natl. Acad. Sci. USA.* (1985) 83:3320-3324.
Shuai et al., Formaldehyde stabilization facilitates lignin monomer production during biomass depolymerization, *Science* (2016) 354(6310), 329-333.
Sibout et al., Structural redesigning *Arabidopsis* lignins into alkalisoluble lignins through the expression of p-coumaroyl-CoA:monolignol transferase PMT. *Plant Physiol.* (2016) 170 (3), 1358-66.
Sharp, RNAi and double-strand RNA, (1999) Genes Dev. 13:139-141.
Sharp and Zamore, Molecular biology. RNA interference, (2000) Science 287:2431-2433.
Smith, D.C.C. (1955a) Ester groups in lignin. Nature 176:267-268.
Smith, D.C.C. (1955b) p-Hydroxybenzoates groups in the lignin of Aspen (Populus tremula) Journal of the Chemical Society 2347).
Sievers et al., Fast, scalable generation of high-quality protein multiple sequence alignments using Clustal Omega. *Mol Syst Biol.* (2011) 7:539.
Smith and Waterman, Comparison of Biosequences, (1981) *Adv. Appl. Math* 2:482.
Smith et al., The challenges of genome sequence annotation or "The devil is in the details", *Nature Biotechnology* (1997) 15:1222-1223.
Smith et al., Engineering monolignol p-coumarate conjugates into poplar and arabidopsis lignins, *Plant Physiology* (2015) 169, 2992-3001.
Smith et al., Defining the diverse cell populations contributing to lignification in *Arabidopsis thaliana* 13 stems, *Plant Physiology* (2017) 174, 1028-1036.
Stalker et al., Herbicide resistance in transgenic plants expressing a bacterial detoxification gene, *Science* (1988) 242:419-423.
Stewart et al., The effects on lignin structure of overexpression of ferulate 5-hydroxylase in hybrid poplar, *Plant Physiol.* (2009) 150(2), 621-635.
Stiefel et al., Expression of a maize cell wall hydroxyproline-rich glycoprotein gene in early leaf and root vascular differentiation, *The Plant Cell.* (1990) 2:785-793.
Sullivan et al., Isolation and characterization of a maize chlorophyll a/b binding protein gene that produces high levels of mRNA in the dark, *Mol. Gen. Genet.* (1989) 215:431.
Sutcliffe, J. G., Complete nucleotide sequence of the *Escherichia coli* plasmid pBR322, *Proc. Natl. Acad. Sci. USA.* (1978) 75:3737-3741.
Tabara et al. The rde-1 gene, RNA interference, and transposon silencing in C. elegans (1999) Cell 99:123-132.
Thillet et al., Site-directed mutagenesis of mouse dihydrofolate reductase. Mutants with increased resistance to methotrexate and trimethoprim, *J. Biol. Chem.* (1988) 263:12500-12508.
Thornton et al., From structure to function: Approaches and limitations, *Nature structural Biology, structural genomics supplement*, (Nov. 2000).
Tijssen, Laboratory Techniques in Biochemistry and Molecular Biology—Hybridization With Nucleic Acid Probes, part 1, chapter 2, "Overview of principles of hybridization and the strategy of nucleic acid probe assays," Elsevier, N.Y. (1993) (Book—Copy Not Provided).
Tuominen et al., Differential phylogenetic expansions in BAHD acyltransferases across five angiosperm taxa and evidence of divergent expression among *Polulus* paralogues, *BMC Genomics*, (2011) 12-236.
Twell et al., Transient Expression of Chimeric Genes Delivered into Pollen by Microprojectile Bombardment, *Plant Physiol.* (1989) 91:1270 1274.
UNIPROTKB—A0A2K2CDA7 (A0A2K2CDA7_POPTR), Mar. 28, 2018 [online]. [Retrieved on Jan. 24, 2020]. Retrieved from the internet ,https://www.uniprot.org/uniprot/A0A2K2CDA7>.
Upton et al., Strategies for the conversion of lignin to high-value polymeric materials: Review and perspective, *Chemical Reviews* (2016) 116(4), 2275-2306.
Vanholme et al., Lignin engineering, *Curr. Opin. Plant Biol.* (2008) 11(3), 278-285.
Vanholme et al., Lignin biosynthesis and structure, *Plant Physiol.* (2010) 153(3), 895-905.
Vanholme et al., Metabolic engineering of novel lignin in biomass crops, *New Phytol.* (2012) 196(4), 978-1000.
Walker et al., DNA sequences required for anaerobic expression of the maize alcohol dehydrogenase 1 gene, *Proc. Natl. Acad. Sci. USA.* (1987) 84:6624-6628.
Wang et al., Characterization of cis-acting elements regulating transcription from the promoter of a constitutively active rice actin gene, *Mol. Cell. Biol.* (1992) 12:3399.

(56) References Cited

OTHER PUBLICATIONS

Ware NCBI, GenBank Sequence Accession No. AQK78565.1; Published (Feb. 7, 2017).

Wells, Additivity of Mutational Effects in Proteins, *Biochemistry* (1990) 29:8509-8517.

Wilkerson et al., (GenBank Sequence Accession No. AHL24755; pp. 1-2; 2014).

Wilkerson et al., Monolignol ferulate transferase introduces chemically labile linkages into the lignin backbone, *Science* (2014) 344:91.

Wishart et al., A single Mutation Converts a Novel Phosphotyrosine Binding Domain into a Dual-specificity Phosphatase, *JBC*, (1995) 270:26782-26785.

Withers et al., Identification of a grass-specific enzyme that acylates monolignols with p-coumarate, *Journal of Biological Chemistry* (2012) 287, 8347-8355.

Wooten and Federhen, Statistics of Local Complexity in Amino Acid Sequences and Sequence Databases, *Comput. Chem.* (1993) 17:149-63.

Yang et al., Maize sucrose synthase-1 promoter directs phloem cell-specific expression of Gus gene in transgenic tobacco plants, *Proc. Natl. Acad. Sci. USA.* (1990) 87:4144-4148.

Yang et al., Expression of the REB transcriptional activator in rice grains improves the yield of recombinant proteins whose genes are controlled by a Reb-responsive promoter, *PNAS*, (2001) 98:11438-11443.

Yelle et al., Characterization of non-derivatized plant cell walls using high-resolution solution-state NMR spectroscopy, *Magn. Reson. Chem.* (2008) 46(6), 508-517.

Zukowski et al., Chromogenic identification of genetic regulatory signals in *Bacillus subtilis* based on expression of a cloned *Pseudomonas* gene, *Proc. Natl. Acad. Sci. USA.* (1983) 80:1101.

Hanzawa, et al. "A single amino acid converts a repressor to an activator of flowering," PNAS, 102, 2005, 7748-7753.

U.S. Appl. No. 15/956,089, filed Apr. 18, 2018, John Ralph.

\* cited by examiner monolignols
(ML)

*p*-coumaroyl-CoA
(*p*CA-CoA)

feruloyl-CoA
(FA-CoA)

monolignol *p*-coumarate
(ML-*p*CA)

monolignol ferulate
(ML-FA)

Brachypodium BdFMT

Brachypodium BdFMT

```
ZmFMT   --MASITVTRKSQSFVVPSSTPTP---TTETLELSPIDRVPGLRHTVRSLHVFRRKDAAA
SbFMT   MATTIITVTRKSQSFVVPSSSSAPVPTTAETLELSAIDRVPGLRHTVRSLHVFRRKADDD
PvFMT   --MVNITVTRKSQSFVVPASSEPA--SAETTLELSAIDRVPGLRHTVRSLHVFRNKKESA
BdFMT   -MAEICTVNRKSQSFVKPAAPTPTPQTPPPLLELSAIDRVPGLRHTVRSLHVFRPPPH--
              **.*******  *::           ****  ******************

ZmFMT   SAA-HYDAAAAGRPAEVIRAALSRALVDYRPFAGRFVGSLYAGEASVECTDDGAWFVDAV
SbFMT   AA--AAAAAASRRPAEVIRAALSRALVDYRPFAGRFVGSLYAGEACVECTDEGAWFVEAV
PvFMT   AGAGCDDDDAASRPGEVIRAALSRALVDYRPFAGRFVGSVAAGETCVECTDDGAWFVEAV
BdFMT   -----GDGAACSRPAEVIRAALARALVEYPAFAGRLVVGGSGSDCGVACTGDGAWFVEAA
             *. **.*******.****:*   ****:*  .   ..:  * **.:*****:*.

ZmFMT   TDCSLEDVNGL-DYPLMVSEEELLPA-PEEGVDPTSIPIMMQVTEFACGGFVVGLVAVHT
SbFMT   ADCSLDDVNGLDDYPLMVSEEELLPA-PEEGVDPTSIPMMMQVTEFSCGGFVVGLVAVHT
PvFMT   ADCSLEGVNGL-DYPLMVSEEELLPA-PEEGVDPTSIPIMMQVTEFACGGFVVGLVAVHT
BdFMT   AGCNLEDVNEL-DYPLVVCEEELLPTAPEGELDPTSIPVMMQVTEFSCGGFVVGLVAVHT
        :.*.*:.** * ****:*.******: **    :******:*******:**********

ZmFMT   LADGLGAAQFINAISEFARGVVKPTIAPIWARELIPNPPKMPPGPPPSFECFGFKHFVMD
SbFMT   LADGLGAAQFINAISEFARGLDKLTIAPVWARSLIPNPPKLPPAPPPSFESFGFKHFVMD
PvFMT   LADGLGAAQFINAISEFARGMEKPTVAPVWARALIPNPPKLPGAPPSFKSFGFQHFTVD
BdFMT   FADGLGAAQFINAIAEFARGLNRPTVNPIWARATIPNPPKFPPGPPPSFQSFGFQHFATD
        :************:*****:   :  *: *:***  ******: *. ****:.***:**. *

ZmFMT   VAVNNIAHVKSEYFQTNGHYCSTFDVAIAKVWQARTRAIKYEPNFKVHVCFFANTRHLLT
SbFMT   VTFDNIAHVKTEYFQANGQYCSTFDVAIAKVWQARTRAIKYNPDVKVHVCFFANTRHLLT
PvFMT   VTSDRIAYVKTQYHQATGQYCSTFDVAIAKVWQARTKAIKYSLESQVHVCFFANTRHLLT
BdFMT   IRPDRIAHAKAEYLKATGTHCSAFDVAVAKVWQARTRAVRYGPEAQVQVCFFANTRHLLG
        :    :.**:..*::* ::.* :**:****:**********:::*   : :*:**********

ZmFMT   HVLPKVGGFYGNCFYPVTVTATAEVVA-SSRLLDVIRMIRDGKARLPLEFSRWSTGN---
SbFMT   RELPNDGGFYGNCFYPVTVTATAEGVA-SGGLHDVIRMIRDGKARLPLEFAKWSMGD---
PvFMT   QVLPKNGGFYGNCFYPVSVTATAEDVV-TAGLLDVIRMIRNGKARLPLEFSKWAAGD---
BdFMT   ELLPE--GFYGNCFFPVTVKARAGDVAGSKDLLGIIRMIRDGKARLPLEFADWASGLGGG
          **:   ******:**:** . * *   *  . : *****:*********:  *:  *

ZmFMT   --------VKVDPYQLTFKHNVLFVSDWTRLGFFEVDYGWGVPNHILPFTYADYMAVAVL
SbFMT   --------VKVDPYQLTFKHNVLFVSDWTRLGFFEVDYGWGVPNHIIPFTYADYMAVAVL
PvFMT   --------VSVDPYQLTFEHNVLFVSDWTRLGFSEVDYGWGAPDHIVPFTYADYMAVAVL
BdFMT   GAGDKMKFVQDDPYELRFEHNVLFVSDWTRLGFLEVDYGWGVPSHVIPFNYADYMAVAVL
                *.  ***:* *:******.******* *******.*.*::**.**********

ZmFMT   GAPPSM--KKGTRIMTQCVEEEHLVDFKAEMKAFF*    SEQ ID NO:2
SbFMT   GAPPTTVKNKGTRIMTQCVEEKHLMEFKDEMKAFF*    SEQ ID NO:4
PvFMT   GAPPSP--KKGTRIMTQCVEEKHLMDFKDEMKAFF*    SEQ ID NO:6
BdFMT   GAPPAP--VKGTRVMTQCVEEKHLKEFRDEMEGSF*    SEQ ID NO:9
        ****:    ****:*******.**  *:. **
```

*FIG. 12*

```
ZmFMT   --MASITVTRKSQSFVVPSSTPTP---TTETLELSPIDRVPGLRHTVRSLHVFRRKDAAA
SbFMT   MATTIITVTRKSQSFVVPSSSSAPVPTTAETLELSAIDRVPGLRHTVRSLHVFRRKADDD
PvFMT   --MVNITVTRKSQSFVVPASSEPA--SAETTLELSAIDRVPGLRHTVRSLHVFRNKKESA
          . ************.*:         : ***** *****************.*

ZmFMT   SAA-HYDAAAAGRPAEVIRAALSRALVDYRPFAGRFVGSLYAGEASVECTDDGAWFVDAV
SbFMT   AA--AAAAAASRRPAEVIRAALSRALVDYRPFAGRFVGSLYAGEACVECTDEGAWFVEAV
PvFMT   AGAGCDDDDAASRPGEVIRAALSRALVDYRPFAGRFVGSVAAGETCVECTDDGAWFVEAV
        :.         *: **.********************..***:.*****.*****.**

ZmFMT   TDCSLEDVNGL-DYPLMVSEEELLPAPEEGVDPTSIPIMMQVTEFACGGFVVGLVAVHTL
SbFMT   ADCSLDDVNGLDDYPLMVSEEELLPAPEEGVDPTSIPMMMQVTEFSCGGFVVGLVAVHTL
PvFMT   ADCSLEGVNGL-DYPLMVSEEELLPAPEEGVDPTSIPIMMQVTEFACGGFVVGLVAVHTL
        :****:.****  **************************:*******:***********

ZmFMT   ADGLGAAQFINAISEFARGVVKPTIAPIWARELIPNPPKMPPGPPPSFECFGFKHFVMDV
SbFMT   ADGLGAAQFINAISEFARGLDKLTIAPVWARSLIPNPPKLPPAPPPSFESFGFKHFVMDV
PvFMT   ADGLGAAQFINAISEFARGMEKPTVAPVWARALIPNPPKLLPGAPPSFKSFGFQHFTVDV
        *******************:  *.**.***.*******: *..****:.***:**.:**

ZmFMT   AVNNIAHVKSEYFQTNGHYCSTFDVAIAKVWQARTRAIKYEPNFKVHVCFFANTRHLLTH
SbFMT   TFDNIAHVKTEYFQANGQYCSTFDVAIAKVWQARTRAIKYNPDVKVHVCFFANTRHLLTR
PvFMT   TSDRIAYVKTQYHQATGQYCSTFDVAIAKVWQARTKAIKYSLESQVHVCFFANTRHLLTQ
        : :.**.**::*.*:.*.*****************:****.  :.*************:

ZmFMT   VLPKVGGFYGNCFYPVTVTATAEVVASSRLLDVIRMIRDGKARLPLEFSRWSTGNVKVDP
SbFMT   ELPNDGGFYGNCFYPVTVTATAEGVASGGLHDVIRMIRDGKARLPLEFAKWSMGDVKVDP
PvFMT   VLPKNGGFYGNCFYPVSVTATAEDVVTAGLLDVIRMIRNGKARLPLEFSKWAAGDVSVDP
        **: ************.******  *:.. * ******:********::*: *:*.***

ZmFMT   YQLTFKHNVLFVSDWTRLGFFEVDYGWGVPNHILPFTYADYMAVAVLGAPPSM--KKGTR
SbFMT   YQLTFKHNVLFVSDWTRLGFFEVDYGWGVPNHIIPFTYADYMAVAVLGAPPTTVKNKGTR
PvFMT   YQLTFEHNVLFVSDWTRLGFSEVDYGWGAPDHIVPFTYADYMAVAVLGAPPSP--KKGTR
        *****:************** ******.*:**:*****************:   :****

ZmFMT   IMTQCVEEEHLVDFKAEMKAFF*    SEQ ID NO:2
SbFMT   IMTQCVEEKHLMEFKDEMKAFF*    SEQ ID NO:4
PvFMT   IMTQCVEEKHLMDFKDEMKAFF*    SEQ ID NO:6
        ********.**..** ******
```

*FIG. 13*

|        | ZmFMT  | SbFMT  | PvFMT  | BdFMT  |
|--------|--------|--------|--------|--------|
| ZmFMT  | 100.00 | 85.65  | 80.83  | 68.94  |
| SbFMT  | 85.65  | 100.00 | 81.29  | 70.16  |
| PvFMT  | 80.83  | 81.29  | 100.00 | 70.42  |
| BdFMT  | 68.94  | 70.16  | 70.42  | 100.00 |

*FIG. 14*

FERULOYL-CoA:MONOLIGNOL TRANSFERASES

STATEMENT REGARDING FEDERALLY SPONSORED RESEARCH

This invention was made with government support under DE-FC02-07ER64494 awarded by the US Department of Energy. The government has certain rights in the invention.

FIELD OF THE INVENTION

The invention is directed to nucleic acids encoding feruloyl-CoA:monolignol transferase enzymes and feruloyl-CoA:monolignol transferase enzymes, as well as expression cassettes, plant cells, and plants that have or encode such nucleic acids and enzymes, and methods of making and using such nucleic acids, polypeptides, expression cassettes, cells, and plants.

BACKGROUND

Lignin is an important cell wall component that provides structural support to plants and is needed for plant vascular tissue function. It is one of the most abundant organic polymers on Earth, constituting about 30% of non-fossil organic carbon and from a quarter to a third of the dry mass of wood. Because the chemical structure of lignin is difficult to degrade by chemical and enzymatic means, lignin makes the task of producing paper and biofuels from plant cell walls difficult.

SUMMARY OF THE INVENTION

The invention relates to the identification and isolation of new acyltransferase nucleic acids and polypeptides. The acyltransferase is a feruloyl-CoA:monolignol transferase (FMT, also called a monolignol ferulate transferase) that produces monolignol ferulates, which can be used for making plants that contain a readily cleavable lignin. Use of the feruloyl-CoA:monolignol transferase nucleic acids and/or polypeptides in plants can simplify the processes used for making biofuels and paper from those plants because these plants have lignin that is more readily removed by chemical treatment or pretreatment.

One aspect of the invention is an isolated nucleic acid encoding a feruloyl-CoA:monolignol transferase polypeptide with a SEQ ID NO:2, SEQ ID NO:4, SEQ ID NO:6, or SEQ ID NO:7 sequence.

Such feruloyl-CoA:monolignol transferases can catalyze the synthesis of monolignol ferulate(s) from monolignol(s) and feruloyl-CoA. For example, the monolignol can be coniferyl alcohol, p-coumaryl alcohol, sinapyl alcohol or a combination thereof, and the feruloyl-CoA:monolignol transferase can, for example, synthesize coniferyl ferulate, p-coumaryl ferulate, sinapyl ferulate or a combination thereof. Feruloyl-CoA:monolignol transferases with SEQ ID NO:2, SEQ ID NO:4, SEQ ID NO:6, or SEQ ID NO:7 sequences are unique in that they are selective for generating monolignol ferulates and have minimal to no relevant activity in generating monolignol coumarates. This is important as these transferases can be used to generate readily cleavable lignin containing monolignol ferulates without conducting other extraneous activity.

In some embodiments, the feruloyl-CoA:monolignol transferase nucleic acid encodes a feruloyl-CoA:monolignol transferase polypeptide with a SEQ ID NO:2, SEQ ID NO:4, SEQ ID NO:6, or SEQ ID NO:7 sequence. In other embodiments, the nucleic acids can, for example, encode a feruloyl-CoA:monolignol transferase that can catalyze the synthesis of monolignol ferulate(s) from a monolignol(s) and feruloyl-CoA with at least about 50%, of the activity of a feruloyl-CoA:monolignol transferase with the SEQ ID NO:2, SEQ ID NO:4, SEQ ID NO:6, or SEQ ID NO:7 amino acid sequence.

Another aspect of the invention is a transgenic plant cell comprising an isolated nucleic acid encoding a feruloyl-CoA:monolignol transferase. The nucleic acid can include any of the feruloyl-CoA:monolignol transferase nucleic acids described herein. For example, the nucleic acid can include a nucleic acid segment that can selectively hybridize to a DNA with a SEQ ID NO:1, SEQ ID NO:3, or SEQ ID NO:5 sequence, or a nucleic acid that encodes a SEQ ID NO:2, SEQ ID NO:4, SEQ ID NO:6, or SEQ ID NO:7 amino acid sequence, or a nucleic acid that encodes a feruloyl-CoA:monolignol transferase that can catalyze the synthesis of monolignol ferulate(s) from a monolignol(s) and feruloyl-CoA with at least about 50%, of the activity of a feruloyl-CoA:monolignol transferase with the SEQ ID NO:2, SEQ ID NO:4, SEQ ID NO:6, or SEQ ID NO:7 amino acid sequence.

Another aspect of the invention is an expression cassette comprising one of the feruloyl-CoA:monolignol transferase nucleic acids described herein that is operably linked to a promoter functional in a host cell. Such a nucleic acid can include a nucleic acid segment that can selectively hybridize to a DNA with a SEQ ID NO:1, SEQ ID NO:3, or SEQ ID NO:5 sequence, or a nucleic acid that encodes a SEQ ID NO:2, SEQ ID NO:4, SEQ ID NO:6, or SEQ ID NO:7 amino acid sequence, or a nucleic acid that encodes a feruloyl-CoA:monolignol transferase that can catalyze the synthesis of monolignol ferulate(s) from a monolignol(s) and feruloyl-CoA with at least about 50%, of the activity of a feruloyl-CoA:monolignol transferase with the SEQ ID NO:2, SEQ ID NO:4, SEQ ID NO:6, or SEQ ID NO:7 amino acid sequence. The expression cassette can further comprise a selectable marker gene. In some embodiments, the expression cassette further comprises plasmid DNA. For example, the expression cassette can be within an expression vector. Promoters that can be used within such expression cassettes include promoters functional during plant development or growth.

Another aspect of the invention is a plant cell that includes an expression cassette comprising one of the feruloyl-CoA:monolignol transferase nucleic acids described herein that is operably linked to a promoter functional in a host cell. Such a nucleic acid can include a nucleic acid segment that can selectively hybridize to a DNA with a SEQ ID NO:1, SEQ ID NO:3, or SEQ ID NO:5 sequence, or a nucleic acid that encodes a SEQ ID NO:2, SEQ ID NO:4, SEQ ID NO:6, or SEQ ID NO:7 amino acid sequence, or a nucleic acid that encodes a feruloyl-CoA:monolignol transferase that can catalyze the synthesis of monolignol ferulate(s) from a monolignol(s) and feruloyl-CoA with at least about 50%, of the activity of a feruloyl-CoA:monolignol transferase with the SEQ ID NO:2, SEQ ID NO:4, SEQ ID NO:6, or SEQ ID NO:7 amino acid sequence. The plant cell can be a monocot cell. The plant cell can also be a gymnosperm cell. For example, the plant cell can be a maize, grass or softwood cell. In some embodiments, the plant cell is a dicot cell. For example, the plant cell can be a hardwood cell.

Another aspect of the invention is a plant that includes an expression cassette comprising one of the feruloyl-CoA:monolignol transferase nucleic acids described herein that is operably linked to a promoter functional in a host cell. Such a plant can be a monocot. Such a nucleic acid can include a nucleic acid segment that can selectively hybridize to a DNA with a SEQ ID NO:1, SEQ ID NO:3, or SEQ ID NO:5 sequence, or a nucleic acid that encodes a SEQ ID NO:2, SEQ ID NO:4, SEQ ID NO:6, or SEQ ID NO:7 amino acid sequence, or a nucleic acid that encodes a feruloyl-CoA: monolignol transferase that can catalyze the synthesis of monolignol ferulate(s) from a monolignol(s) and feruloyl-CoA with at least about 50%, of the activity of a feruloyl-CoA:monolignol transferase with the SEQ ID NO:2, SEQ ID NO:4, SEQ ID NO:6, or SEQ ID NO:7 amino acid sequence. The plant can also be a gymnosperm. For example, the plant can be a maize, grass or softwood plant. In some embodiments, the plant is a dicot plant. For example, the plant can be a hardwood plant.

Another aspect of the invention is a method for incorporating monolignol ferulates into lignin of a plant that includes:

a) stably transforming plant cells with the expression cassette comprising one of the feruloyl-CoA:monolignol transferase nucleic acids described herein to generate transformed plant cells;

b) regenerating the transformed plant cells into at least one transgenic plant, wherein feruloyl-CoA:monolignol transferase is expressed in at least one transgenic plant in an amount sufficient to incorporate monolignol ferulates into the lignin of the transgenic plant.

For example, such a nucleic acid can be a nucleic acid that can selectively hybridize to a DNA with a SEQ ID NO:1, SEQ ID NO:3, or SEQ ID NO:5 sequence, or a nucleic acid that encodes a SEQ ID NO:2, SEQ ID NO:4, SEQ ID NO:6, or SEQ ID NO:7 amino acid sequence, or a nucleic acid that encodes a feruloyl-CoA:monolignol transferase that can catalyze the synthesis of monolignol ferulate(s) from a monolignol(s) and feruloyl-CoA with at least about 50%, of the activity of a feruloyl-CoA:monolignol transferase with the SEQ ID NO:2, SEQ ID NO:4, SEQ ID NO:6, or SEQ ID NO:7 amino acid sequence. The method can be used to generate a transgenic plant that is fertile. The method can further include recovering transgenic seeds from the transgenic plant, wherein the transgenic seeds include the nucleic acid encoding a feruloyl-CoA:monolignol transferase. The plant containing monolignol ferulates within its lignin can be a monocot. The plant can also be a gymnosperm. For example, the plant can be a maize, grass or softwood plant. In some embodiments, the plant is a dicot plant. For example, the plant can also be a hardwood plant. Such a method can further include stably transforming the plant cell(s) or the plant with at least one selectable marker gene. The selectable marker can be linked or associated with the expression cassette.

In some embodiments, the lignin in the plant that has the nucleic acid encoding a feruloyl-CoA:monolignol transferase can include at least 1% monolignol ferulate. In other embodiments, the lignin in the plant can include at least 5% monolignol ferulate, or at least 10% monolignol ferulate, or at least 20% monolignol ferulate, or at least 25% monolignol ferulate. In further embodiments, the lignin in the plant includes about 1-30% monolignol ferulate, or about 2-30% monolignol ferulate.

The method for incorporating monolignol ferulates into lignin of a plant can also include breeding the fertile transgenic plant to yield a progeny plant, where the progeny plant has an increase in the percentage of monolignol ferulates in the lignin of the progeny plant relative to the corresponding untransformed plant.

Another aspect of the invention is a lignin isolated from the transgenic plant comprising any of the feruloyl-CoA: monolignol transferase isolated nucleic acids described herein. Another aspect of the invention is a woody material isolated from the transgenic plant comprising any of the feruloyl-CoA:monolignol transferase isolated nucleic acids described herein. The lignin or woody tissue can include any of the nucleic acids described herein that encode a feruloyl-CoA:monolignol transferase. In other embodiments, the lignin or woody tissue can include any of the feruloyl-CoA: monolignol transferase amino acid or polypeptide sequences described herein.

Another aspect of the invention is a method of making a product from a transgenic plant comprising: (a) providing a transgenic plant that includes one of the isolated nucleic acids described herein that encodes a feruloyl-CoA:monolignol transferase; and (b) processing the transgenic plant's tissues under conditions sufficient to digest the lignin; to thereby generate the product from the transgenic plant, wherein the transgenic plant's tissues comprise lignin having an increased percent of monolignol ferulates relative to a corresponding untransformed plant. Such a corresponding untransformed plant is typically a plant of the same species, strain and/or accession as the transformed plant. The conditions sufficient to digest the lignin can include conditions sufficient to cleave ester bonds within monolignol ferulate-containing lignin. In some embodiments, the conditions sufficient to digest the lignin include mildly alkaline conditions. In some embodiments, the conditions sufficient to digest the lignin include contacting the transgenic plant's tissues with ammonia for a time and a temperature sufficient to cleave ester bonds within monolignol ferulate-containing lignin. In some embodiments, the conditions sufficient to digest the lignin include acidic conditions. In some embodiments, the conditions sufficient to digest the lignin would not cleave substantially any of the ether and carbon-carbon bonds in lignin from a corresponding plant that does not contain the isolated nucleic acid encoding the feruloyl-CoA: monolignol transferase.

Another aspect of the invention is an isolated nucleic acid encoding a feruloyl-CoA:monolignol transferase, wherein the nucleic acid can selectively hybridize to a DNA with a SEQ ID NO:1, SEQ ID NO:3, or SEQ ID NO:5 sequence. For example, the nucleic acid can selectively hybridize to a DNA with a SEQ ID NO:1, SEQ ID NO:3, or SEQ ID NO:5 sequence under stringent hybridization conditions. In some embodiments, the stringent hybridization conditions comprise a wash in 0.1×SSC, 0.1% SDS at 65° C. Such an isolated nucleic acid can have at least about 79%, at least about 80%, at least about 90%, or at least 95% sequence identity with SEQ ID NO:1, SEQ ID NO:3, or SEQ ID NO:5. In some embodiments, the isolated nucleic acid with the SEQ ID NO:1, SEQ ID NO:3, or SEQ ID NO:5 sequence encodes a feruloyl-CoA:monolignol transferase.

Therefore, the invention embraces nucleic acids encoding feruloyl-CoA:monolignol transferase enzymes and feruloyl-CoA:monolignol transferase enzymes, as well as expression cassettes, plant cells, and plants that have or encode such nucleic acids and enzymes, and methods of making and using such nucleic acids, polypeptides, expression cassettes, cells, and plants.

BRIEF DESCRIPTION OF THE DRAWINGS

FIGS. 1A and 1B show examples of lignin structures that may be found in a softwood (spruce). FIGS. 1C and 1D show examples of lignin structures that may be present in a hardwood (poplar). [Ralph, J., Brunow, G., and Boerjan, W. (2007) Lignins. In: Rose, F., and Osborne, K. (eds). Encyclopedia of Life Sciences, DOI: 10.1002/9780470015902.a0020104, John Wiley & Sons, Ltd., Chichester, UK]. The softwood lignin is generally more branched and contains a lower proportion of β-ether units. Note that each of these structures represents only one of billions of possible isomers [Ralph, J., Lundquist, K., Brunow, G., Lu, F., Kim, H., Schatz, P. F., Marita, J. M., Hatfield, R. D., Ralph, S. A., Christensen, J. H., and Boerjan, W. Lignins: natural polymers from oxidative coupling of 4-hydroxyphenylpropanoids. (2004) Phytochem. Revs. 3(1), 29-60]. Thus, these structures are merely illustrative of some of the linkage types that may be present different lignins. An "S" within a ring indicates a syringyl unit while a "G" within a unit indicates a guaiacyl unit.

FIG. 2A shows the structure of sinapyl alcohol as a possible reactant. Coniferyl alcohol, another possible reactant, lacks one of the two methoxy groups present on sinapyl alcohol. p-Hydroxycinnamyl alcohol (p-coumaryl alcohol), another possible reactant, lacks both of the two methoxy groups present on sinapyl alcohol. FIG. 2B shows the structure of p-coumaroyl-CoA, another possible reactant. FIG. 2C shows the structure of feruloyl-CoA, another possible reactant. FIG. 2D shows the structure of sinapyl p-coumarate as a possible product resulting from the conjugation of sinapyl alcohol with p-coumaryl-CoA. Coniferyl p-coumarate, a possible product resulting from the conjugation of coniferyl alcohol with p-coumaryl-CoA, lacks one of the two methoxy groups present on sinapyl p-coumarate. p-Hydroxycinnamyl coumarate (p-coumaryl coumarate), a possible product resulting from the conjugation of p-hydroxycinnamyl alcohol and p-coumaryl-CoA, lacks both of the two methoxy groups present on sinapyl p-coumarate. FIG. 2E shows the structure of sinapyl ferulate as a possible product resulting from the conjugation of sinapyl alcohol with feruloyl-CoA. Coniferyl ferulate, a possible product resulting from the conjugation of coniferyl alcohol with feruloyl-CoA, lacks one of the two methoxy groups present on sinapyl ferulate. p-Hydroxycinnamyl ferulate (p-coumaryl ferulate), a possible product resulting from the conjugation of p-hydroxycinnamyl alcohol and feruloyl-CoA, lacks both of the two methoxy groups present on sinapyl ferulate.

FIG. 12 shows an alignment of the amino acid sequences of ZmFMT (SEQ ID NO:2), SbFMT (SEQ ID NO:4), PvFMT (SEQ ID NO:6), and BdFMT (SEQ ID NO:16) using Clustal Omega (Sievers F, Wilm A, Dineen D, Gibson T J, Karplus K, Li W, Lopez R, McWilliam H, Remmert M, Soding J, Thompson J D, Higgins D G. Fast, scalable generation of high-quality protein multiple sequence alignments using Clustal Omega. Mol Syst Biol. 2011 Oct. 11; 7:539). An "*" (asterisk) indicates positions which have a single, fully conserved residue. A ":" (colon) indicates conservation between groups of strongly similar properties (scoring >0.5 in the Gonnet PAM 250 matrix). A "." (period) indicates conservation between groups of weakly similar properties (scoring=<0.5 in the Gonnet PAM 250 matrix).

FIG. 13 shows an alignment the amino acid sequences of ZmFMT (SEQ ID NO:2), SbFMT (SEQ ID NO:4), and PvFMT (SEQ ID NO:6) using Clustal Omega. An "*" (asterisk) indicates positions which have a single, fully conserved residue. A ":" (colon) indicates conservation between groups of strongly similar properties (scoring >0.5 in the Gonnet PAM 250 matrix). A "." (period) indicates conservation between groups of weakly similar properties (scoring=<0.5 in the Gonnet PAM 250 matrix).

FIG. 14 shows an identity matrix of the amino acid sequences of ZmFMT (SEQ ID NO:2), SbFMT (SEQ ID NO:4), PvFMT (SEQ ID NO:6), and BdFMT (SEQ ID NO:16) using Clustal Omega. Numbers indicate percent identity.

Figure 1A:
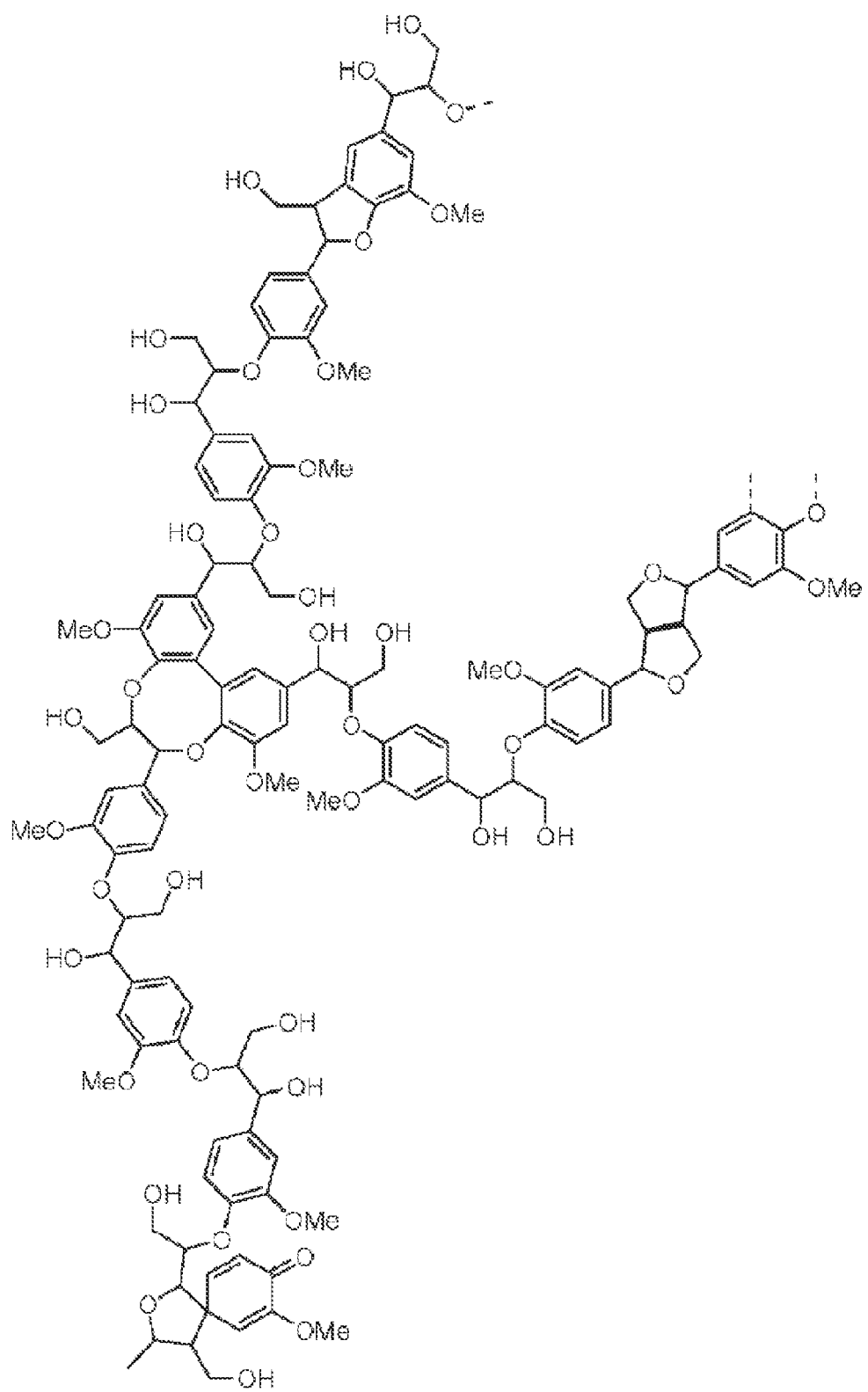
FIGS. 1A, 1B, 1C, and 1D illustrate structural models for some types of lignin polymers.
Figure 1B:
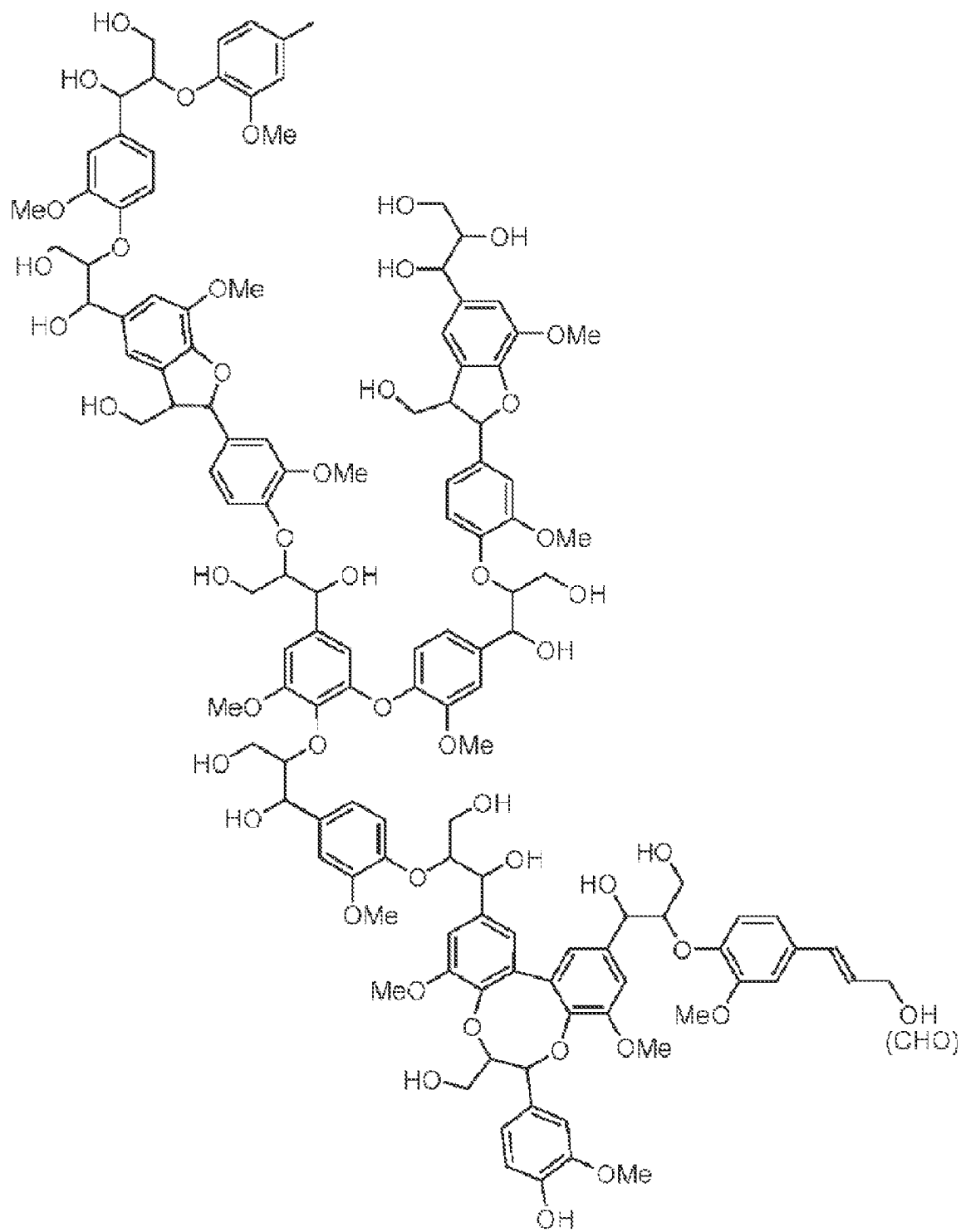
Figure 1C:
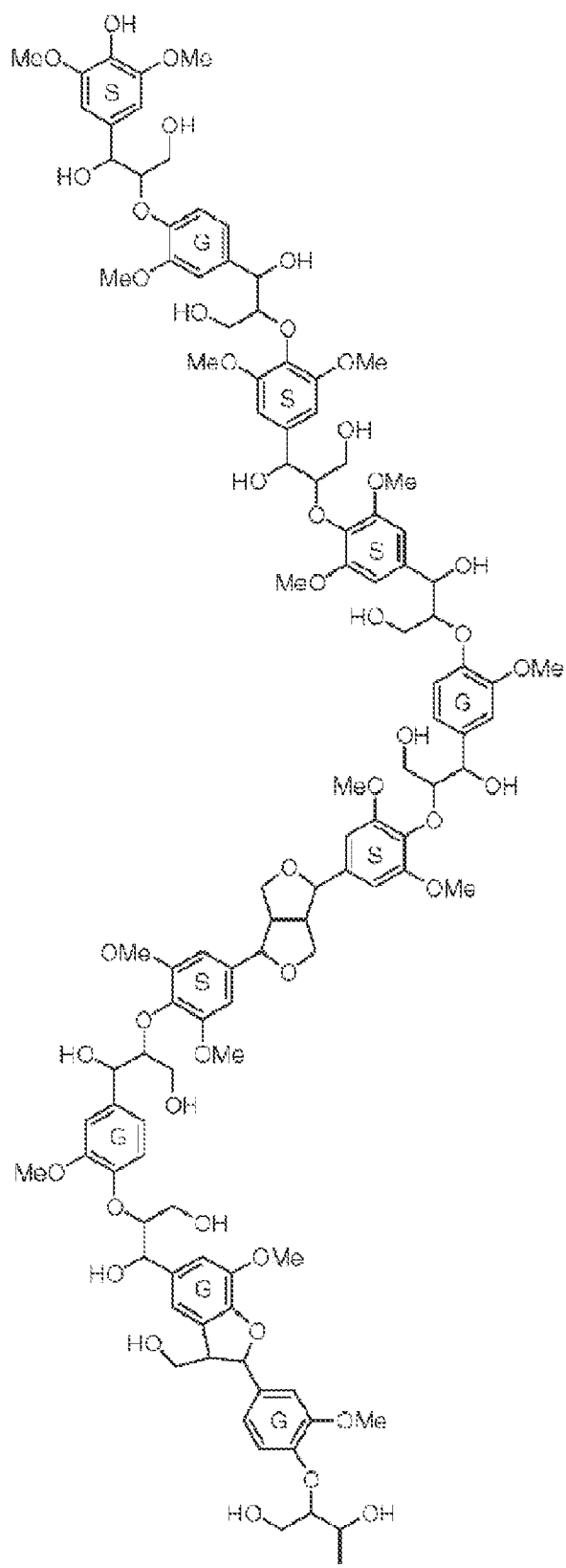
Figure 1D:
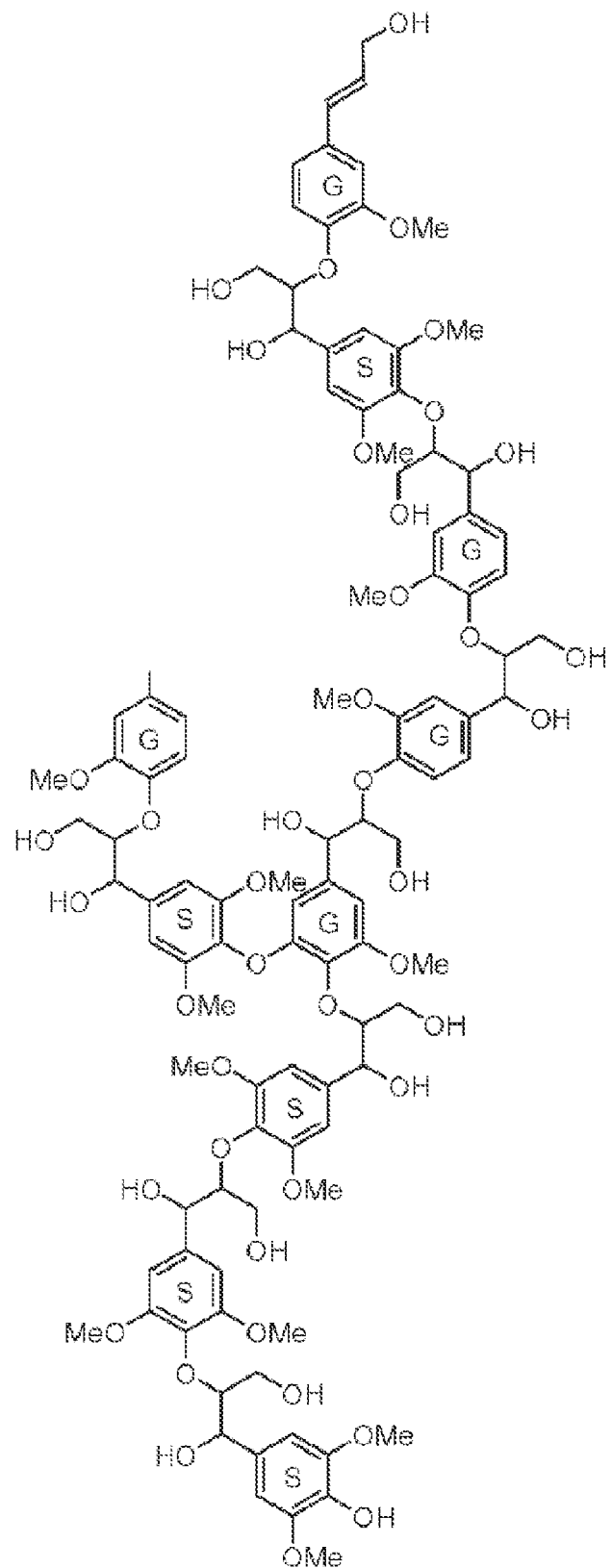

Unless defined otherwise, all technical and scientific terms used herein have the same meaning as commonly understood by one of ordinary skill in the art to which this invention belongs. Unless mentioned otherwise, the techniques employed or contemplated herein are standard methodologies well known to one of ordinary skill in the art. The materials, methods and examples are illustrative only and not limiting. The following is presented by way of illustration and does not limit the scope of the invention.

DETAILED DESCRIPTION OF THE INVENTION

The invention provides nucleic acids and methods useful for altering lignin structure and/or the lignin content in plants. Plants with such altered lignin structure/content are more easily and economically processed into useful products such as biofuels and paper.

Acyl-CoA Dependent Acyltransferases

Plant acyl-CoA dependent acyltransferases constitute a large but specific protein superfamily, named BAHD. Members of this family take an activated carboxylic acid (i.e., a CoA thioester form of the acid) as an acyl donor and either an alcohol or, more rarely, a primary amine, as an acyl acceptor and catalyze the formation of an ester or an amide bond, respectively. The acyl donors and acyl acceptors that act as substrates by BAHD acyltransferases are quite diverse, and different BAHD family members exhibit a range of substrate specificities.

The invention relates to a new type of BAHD acyltransferase nucleic acids and enzymes that enable the production of transgenic plants with altered lignin. The BAHD nucleic acids can be used in the expression cassettes, expression vectors, transgenic plant cells, transgenic plants and transgenic seeds as described herein. The BAHD nucleic acids and encoded proteins are isolated or heterologous nucleic acids or proteins. The term "isolated" when used in conjunction with a nucleic acid or polypeptide, refers to a nucleic acid segment or polypeptide that is present in a form or setting that is different from that in which it is found in nature. For example, an isolated nucleic acid or an isolated polypeptide is identified and separated from at least one contaminant nucleic acid or polypeptide with which it is ordinarily associated in its natural state. In contrast, native nucleic acids, such as DNA, RNA and polypeptides are found in the state they exist in nature. The term "heterologous" when used in reference to a nucleic acid refers to a nucleic acid segment that has been manipulated in some way. For example, a heterologous nucleic acid includes a nucleic acid segment from one species that has been introduced into another species. A heterologous nucleic acid also includes a nucleic acid segment that is native to an organism that has been altered in some way (e.g., mutated, multiple copies are added, the heterologous nucleic acid is linked to a non-native promoter or enhancer sequence, etc.). A heterologous nucleic acid also includes a nucleic acid comprising a combination of genetic elements not occurring in nature. Non-limiting examples of such genetic elements include coding sequences, promoters, enhancers, ribosome binding sites (e.g., Shine Dalgarno sequences, Kozak sequences), etc. The term "heterologous" can also refer to any such individual genetic element when included in such a non-naturally occurring combination. Heterologous nucleic acids can include plant nucleic acid segments such as cDNA forms of a plant gene where the cDNA sequences are expressed in a sense direction to produce mRNA. In some embodiments, heterologous nucleic acids can be distinguished from endogenous plant genes in that the heterologous nucleic acid segments are joined to nucleotide sequences comprising regulatory elements such as promoters that are not found naturally associated with the endogenous gene in its natural chromosome. In some embodiments, heterologous nucleic acid can be distinguished from endogenous plant genes in that the heterologous nucleic acid segments express the encoded protein (or portion of a protein) in parts of the plant where the protein (or portion thereof) is not normally expressed. The term "cDNA" refers to any DNA that includes a coding sequence for a polypeptide and lacks one or more introns present in naturally occurring genomic DNA also comprising that coding sequence, regardless of whether or not the cDNA is directly generated from mRNA.

The acyltransferases described herein are feruloyl-CoA:monolignol transferases that synthesize monolignol ferulates from any of three monolignols (p-coumaryl, coniferyl and sinapyl alcohols). For example, the feruloyl-CoA:monolignol transferases described herein can synthesize coniferyl ferulate from coniferyl alcohol and feruloyl-CoA, as shown below.

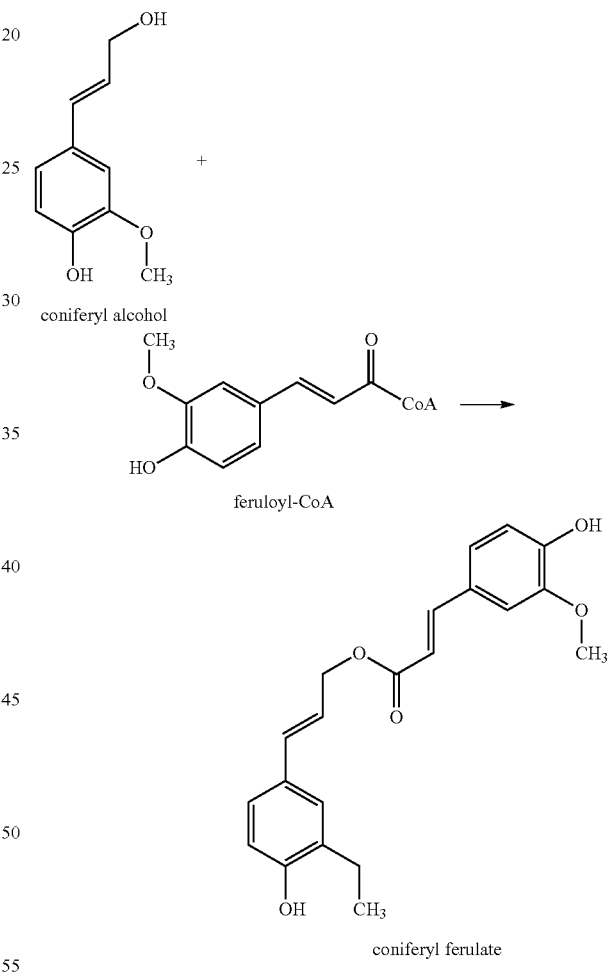

The feruloyl-CoA:monolignol transferases enable production of plants with lignin that is readily cleaved and/or removed, for example, because the lignin in these plants contains monolignol ferulates such as coniferyl ferulate (CAFA).

The terms "feruloyl-CoA:monolignol transferase(s)" and "monolignol ferulate transferase(s)" are used interchangeably herein.

Nucleic acids encoding the feruloyl-CoA:monolignol transferases that are useful for making monolignol ferulates include nucleic acids encoding a *Zea mays* (maize) feruloyl- CoA:monolignol transferase (ZmFMT). An exemplary nucleic acid encoding ZmFMT has the following nucleic acid sequence (SEQ ID NO:1).

ATGGCGAGCATCACCGTGACAAGGAAATCCCAATCCTTCGTCGTGCCAT

CGTCCACGCCAACTCCGACGACCGAGACGCTCGAGTTGTCGCCCATCGA

CCGCGTTCCAGGCCTGCGCCACACGGTGCGATCCCTGCACGTGTTCCGC

CGCAAGGACGCCGCCGCCTCCGCCGCCCACTACGATGCTGCTGCCGCCG

GCAGGCCGGCCGAGGTGATCCGCGCGGCGCTGTCCCGCGCGCTGGTGGA

CTACCGCCCGTTCGCCGGCCGTTTCGTCGGCTCACTGTACGCCGGGGAG

GCGAGCGTTGAGTGCACCGACGACGGTGCGTGGTTCGTGGACGCTGTCA

CAGATTGCAGCCTCGAGGACGTGAACGGCCTCGACTACCCGCTTATGGT

CTCCGAGGAAGAGCTGCTGCCGGCTCCAGAGGAAGGTGTTGACCCAACC

AGTATTCCGATTATGATGCAGGTCACGGAATTTGCTTGTGGAGGATTTG

TGGTGGGGCTAGTCGCAGTGCACACCCTTGCTGACGGGCTCGGTGCAGC

TCAATTCATCAATGCAATTTCTGAGTTTGCCCGTGGAGTAGTTAAACCT

ACAATAGCACCTATATGGGCACGGGAGTTAATACCAAACCCACCTAAAA

TGCCTCCTGGGCCACCACCATCCTTCGAGTGCTTCGGGTTCAAACATTT

TGTTATGGATGTGGCAGTTAACAATATTGCACATGTCAAGAGTGAATAC

TTTCAAACCAATGGACACTATTGCTCTACATTTGATGTTGCCATTGCCA

AGGTTTGGCAAGCTAGGACAAGGGCAATCAAGTACGAACCAAATTTCAA

GGTGCATGTTTGCTTCTTTGCCAACACTCGCCACCTCCTCACACATGTG

CTACCCAAGGTTGGTGGCTTCTATGGAAATTGCTTCTATCCAGTGACTG

TCACAGCAACTGCTGAGGTAGTTGCTAGTTCAAGATTGCTTGATGTGAT

TAGGATGATAAGGGATGGGAAGGCTAGGCTTCCTTTAGAGTTTTCCAGA

TGGTCCACGGGCAATGTGAAAGTAGACCCATATCAACTAACATTCAAGC

ACAATGTTCTATTTGTGTCCGATTGGACACGGCTTGGATTCTTTGAAGT

TGACTATGGGTGGGGTGTACCAAACCATATCCTCCCTTTCACTTATGCA

GACTACATGGCTGTAGCAGTTCTTGGAGCTCCACCGTCTATGAAGAAGG

GGACTCGAATAATGACACAATGTGTCGAGGAGGAGCATCTCGTGGACTT

CAAGGCCGAGATGAAAGCCTTCTTTTAG

SEQ ID NO:1 encodes the following ZmFMT amino acid sequence (SEQ ID NO:2).

MASITVTRKSQSFVVPSSTPTPTTETLELSPIDRVPGLRHTVRSLHVFRR

KDAAASAAHYDAAAAGRPAEVIRAALSRALVDYRPFAGRFVGSLYAGEAS

VECTDDGAWFVDAVTDCSLEDVNGLDYPLMVSEEELLPAPEEGVDPTSIP

IMMQVTEFACGGFVVGLVAVHTLADGLGAAQFINAISEFARGVVKPTIAP

IWARELIPNPPKMPPGPPPSFECFGFKHFVMDVAVNNIAHVKSEYFQTNG

HYCSTFDVAIAKVWQARTRAIKYEPNFKVHVCFFANTRHLLTHVLPKVGG

FYGNCFYPVTVTATAEVVASSRLLDVIRMIRDGKARLPLEFSRWSTGNVK

VDPYQLTFKHNVLFVSDWTRLGFFEVDYGWGVPNHILPFTYADYMAVAVL

GAPPSMKKGTRIMTQCVEEEHLVDFKAEMKAFF

Other nucleic acids encoding feruloyl-CoA:monolignol transferases useful for making monolignol ferulates include nucleic acids encoding a *Sorghum bicolor* (sorghum) feruloyl-CoA:monolignol transferase (SbFMT). An exemplary nucleic acid encoding SbFMT has the following nucleic acid sequence (SEQ ID NO:3).

ATGGCGACGACCATCATCACGGTGACAAGGAAATCCCAGTCGTTCGTCG

TGCCGTCGTCGTCGTCCGCGCCGGTGCCGACGACGGCCGAAACGCTGGA

GCTGTCGGCCATCGACCGCGTGCCGGGGCTGCGCCACACGGTGCGGTCC

CTGCACGTGTTCCGCCGCAAGGCGGACGACGACGCCGCCGCCGCCGCCG

CTGCTGCCAGCAGGAGGCCTGCGGAGGTGATCCGGGCAGCGCTGTCCCG

CGCTCTGGTGGACTACCGTCCGTTCGCCGGCCGCTTCGTCGGCTCGCTG

TACGCCGGGGAGGCGTGCGTCGAGTGCACCGACGAGGGCGCCTGGTTCG

TGGAGGCCGTCGCTGACTGCAGCCTCGATGACGTGAACGGCCTCGACGA

CTACCCGCTCATGGTCTCCGAGGAAGAGCTGCTGCCGGCCCCAGAGGAA

GGTGTTGACCCTACCAGTATTCCCATGATGATGCAGGTCACGGAATTTT

CTTGTGGAGGATTTGTGGTGGGGCTGGTCGCAGTCCACACCCTTGCAGA

TGGGCTCGGTGCAGCTCAATTCATCAATGCAATTTCCGAGTTTGCCCGT

GGACTAGATAAACTTACAATAGCACCTGTGTGGGCTCGGTCGTTAATAC

CAAACCCACCTAAGCTGCCTCCTGCGCCGCCACCATCCTTTGAGTCCTT

TGGGTTCAAACATTTTGTCATGGATGTTACTTTTGACAATATTGCACAT

GTCAAGACTGAGTACTTTCAAGCCAATGGACAATACTGCTCTACATTCG

ATGTTGCCATTGCCAAGGTTTGGCAAGCTAGGACCAGGGCAATCAAGTA

CAATCCAGATGTCAAGGTCCATGTTTGCTTCTTTGCCAACACTCGCCAC

CTCCTCACACGGGAGCTTCCAAACGATGGGGGCTTCTATGGAAATTGCT

TCTATCCGGTGACTGTAACAGCAACTGCTGAGGGTGTTGCTAGTGGAGG

ATTGCATGATGTGATTAGGATGATACGGGATGGGAAGGCTAGGCTGCCT

TTGGAGTTTGCCAAATGGTCCATGGGTGATGTGAAGGTAGACCCATATC

AACTGACATTCAAGCACAATGTTCTGTTTGTGTCTGATTGGACGAGGCT

TGGATTCTTTGAGGTTGACTATGGGTGGGGTGTACCAAACCATATCATA

CCTTTCACTTATGCAGACTACATGGCTGTAGCAGTTCTTGGGGCTCCAC

CTACTACAGTGAAGAACAAGGGGACTCGAATAATGACACAGTGCGTGGA

GGAGAAGCATCTCATGGAATTCAAGGATGAGATGAAGGCCTTCTTTTAG

SEQ ID NO:3 encodes the following SbFMT amino acid sequence (SEQ ID NO:4).

MATTIITVTRKSQSFVVPSSSSAPVPTTAETLELSAIDRVPGLRHTVRSL

HVFRRKADDDAAAAAAAASRRPAEVIRAALSRALVDYRPFAGRFVGSLYA

GEACVECTDEGAWFVEAVADCSLDDVNGLDDYPLMVSEEELLPAPEEGVD

PTSIPMMMQVTEFSCGGFVVGLVAVHTLADGLGAAQFINAISEFARGLDK

LTIAPVWARSLIPNPPKLPPAPPPSFESFGFKHFVMDVTFDNIAHVKTEY

FQANGQYCSTFDVAIAKVWQARTRAIKYNPDVKVHVCFFANTRHLLTREL

PNDGGFYGNCFYPVTVTATAEGVASGGLHDVIRMIRDGKARLPLEFAKWS

-continued
MGDVKVDPYQLTFKHNVLFVSDWTRLGFFEVDYGWGVPNHIIPFTYADYM

AVAVLGAPPTTVKNKGTRIMTQCVEEKHLMEFKDEMKAFF

Other nucleic acids encoding feruloyl-CoA:monolignol transferases useful for making monolignol ferulates include nucleic acids encoding a *Panicum virgatum* (switchgrass) feruloyl-CoA:monolignol transferase (PvFMT). An exemplary nucleic acid encoding PvFMT has the following nucleic acid sequence (SEQ ID NO:5).

ATGGTGAACATCACCGTGACAAGGAAATCCCAGTCCTTCGTCGTGCCGG

CGTCGTCCGAGCCGGCGTCGGCCGAGACGACGCTCGAGCTATCGGCGAT

CGACCGCGTGCCGGGCCTCCGCCACACGGTGCGGTCGCTGCACGTGTTC

CGCAACAAGAAGGAGTCCGCCGCAGGCGCCGGCTGCGACGACGACGATG

CTGCCAGCAGGCCGGGGAGGTGATCCGCGCGGCGCTGTCCCGCGCGCT

GGTGGATTACCGCCCGTTCGCCGGCCGCTTCGTCGGCTCGGTCGCCGCC

GGGGAGACCTGCGTCGAGTGCACCGACGACGGCGCGTGGTTCGTGGAGG

CCGTCGCCGACTGCAGTCTCGAGGGCGTGAATGGCCTCGACTACCCGCT

CATGGTCTCCGAGGAAGAGCTGCTGCCCGCTCCAGAGGAAGGCGTTGAC

CCTACAAGTATTCCGATCATGATGCAGGTTACAGAATTTGCATGCGGAG

GATTTGTGGTTGGGCTGGTAGCAGTCCACACTCTTGCTGACGGGCTCGG

CGCCGCCCAATTCATCAACGCGATTTCTGAGTTTGCTCGTGGGATGGAA

AAGCCCACGGTAGCACCCGTATGGGCTCGGGCTTTAATACCAAACCCAC

CCAAACTGCTTCCCGGGGCACCACCGTCCTTCAAGTCCTTTGGGTTCCA

GCACTTCACCGTGGATGTGACCTCTGACCGGATTGCCTACGTCAAGACC

CAGTACCATCAGGCCACTGGACAGTACTGCTCCACCTTTGATGTCGCCA

TTGCCAAGGTTTGGCAGGCAAGAACCAAGGCAATCAAGTACAGCTTGGA

GTCCCAAGTTCATGTCTGCTTCTTCGCCAACACCCGCCACCTCCTCACC

CAGGTGCTGCCCAAGAATGGGGGATTCTATGGCAACTGCTTCTACCCAG

TTTCTGTGACGGCCACTGCTGAGGATGTTGTCACTGCAGGGTTGCTTGA

TGTGATCAGGATGATAAGGAATGGGAAGGCCAGGCTTCCCCTGGAGTTT

TCCAAGTGGGCAGCAGGGGATGTGAGTGTGGATCCATACCAGTTGACAT

TTGAGCACAACGTGTTGTTTGTGTCTGATTGGACGAGACTTGGGTTCTC

CGAGGTTGACTATGGGTGGGGTGCACCGGATCATATCGTGCCATTCACC

TATGCAGACTACATGGCGGTGGCGGTTCTTGGGGCTCCGCCTTCGCCGA

AGAAGGGAACTCGGATTATGACGCAGTGTGTGGAGGAGAAGCACCTCAT

GGACTTCAAGGATGAGATGAAGGCCTTCTTTTAG

SEQ ID NO:5 encodes the following PvFMT amino acid sequence (SEQ ID NO:6).

MVNITVTRKSQSFVVPASSEPASAETTLELSAIDRVPGLRHTVRSLHVFR

NKKESAAGAGCDDDDAASRPGEVIRAALSRALVDYRPFAGRFVGSVAAGE

TCVECTDDGAWFVEAVADCSLEGVNGLDYPLMVSEEELLPAPEEGVDPTS

IPIMMQVTEFACGGFVVGLVAVHTLADGLGAAQFINAISEFARGMEKPTV

APVWARALIPNPPKLLPGAPPSFKSFGFQHFTVDVTSDRIAYVKTQYHQA

TGQYCSTFDVAIAKVWQARTKAIKYSLESQVHVCFFANTRHLLTQVLPKN

GGFYGNCFYPVSVTATAEDVVTAGLLDVIRMIRNGKARLPLEFSKWAAGD

VSVDPYQLTFEHNVLFVSDWTRLGFSEVDYGWGAPDHIVPFTYADYMAVA

VLGAPPSPKKGTRIMTQCVEEKHLMDFKDEMKAFF

Other nucleic acids encoding the feruloyl-CoA:monolignol transferases useful for making monolignol ferulates are nucleic acids that encode the following amino acid sequence (SEQ ID NO:7).

M$X_1X_2X_3X_4$ITVTRKSQSFVVP$X_5$S$X_6X_7X_8X_9X_{10}X_{11}X_{12}X_{13}X_{14}X_{15}$TLELS $X_{16}$IDRVPGLRHTVRSLHVFR$X_{17}$K$X_{18}X_{19}X_{20}X_{21}X_{22}X_{23}X_{24}X_{25}X_{26}X_{27}X_{28}$ $X_{29}X_{30}X_{31}X_{32}X_{33}$RP$X_{34}$EVIRAALSRALVDYRPFAGRFVGS$X_{35}X_{36}$AGEX$_{37}$ $X_{38}$VECTD$X_{39}$GAWFV$X_{40}$AV$X_{41}$DCSL$X_{42}X_{43}$VNGL$X_{44}$DYPLMVSEEELL

PAPEEGVDPTSIP$X_{45}$MMQVTEF$X_{46}$CGGFVVGLVAVHTLADGLGAAQFIN

AISEFARG$X_{47}X_{48}$K$X_{49}$T$X_{50}$AP$X_{51}$WAR$X_{52}$LIPNPPK$X_{53}X_{54}$P$X_{55}X_{56}$PPS

F$X_{57}X_{58}$FGF$X_{59}$HF$X_{60}X_{61}$DV$X_{62}X_{63}X_{64}X_{65}$IA$X_{66}$VK$X_{67}X_{68}$Y$X_{69}$Q$X_{70}X_{71}$

G$X_{72}$YCSTFDVAIAKVWQART$X_{73}$AIK$YX_{74}X_{75}X_{76}X_{77}X_{78}$VHVCFFANTRH

LLT$X_{79}X_{80}$LP$X_{81}X_{82}$GGFYGNCFYPV$X_{83}$VTATAE$X_{84}$V$X_{85}X_{86}X_{87}X_{88}$L$X_{89}$

DVIRMIR$X_{90}$GKARLPLEF$X_{91}X_{92}$W$X_{93}X_{94}$G$X_{95}$V$X_{96}$VDPYQLTF$X_{97}$HNVL

FVSDWTRLGF$X_{98}$EVDYGWG$X_{99}$P$X_{100}$HI$X_{101}$PFTYADYMAVAVLGAPP $X_{102}X_{103}X_{104}X_{105}X_{106}$KGTRIMTQCVEE$X_{107}$HL$X_{108}X_{109}$FK$X_{110}$EMKAFF wherein:
$X_1$=A, V, or a conservative substitution of any of the foregoing;
$X_2$=T, a conservative or non-conservative substitution thereof, or not present;
$X_3$=T, a conservative or non-conservative substitution thereof, or not present;
$X_4$=I, S, N, or a conservative or non-conservative substitution of any of the foregoing;
$X_5$=S, A, or a conservative substitution of any of the foregoing;
$X_6$=S, T, or a conservative substitution of any of the foregoing;
$X_7$=S, P, E, or a conservative or nonconservative substitution of any of the foregoing;
$X_8$=A, T, P, or a conservative or nonconservative substitution of any of the foregoing;
$X_9$=P, A, or a conservative or nonconservative substitution of any of the foregoing;
$X_{10}$=V, a conservative or nonconservative substitution of any of the foregoing, or not present;
$X_{11}$=P, a conservative or nonconservative substitution of any of the foregoing, or not present;
$X_{12}$=T, S, a conservative or nonconservative substitution of any of the foregoing, or not present;
$X_{13}$=T, A, or a conservative or nonconservative substitution of any of the foregoing;
$X_{14}$=A, T, E, or a conservative or nonconservative substitution of any of the foregoing;
$X_{15}$=E, T, or a conservative or nonconservative substitution of any of the foregoing;
$X_{16}$=A, P, or a conservative or nonconservative substitution of any of the foregoing;

$X_{17}$=R, N, or a conservative or nonconservative substitution of any of the foregoing;

$X_{18}$=A, D, K, or a conservative or nonconservative substitution of any of the foregoing;

$X_{19}$=D, A, E, or a conservative or nonconservative substitution of any of the foregoing;

$X_{20}$=D, A, S, or a conservative or nonconservative substitution of any of the foregoing;

$X_{21}$=D, A, or a conservative or nonconservative substitution of any of the foregoing;

$X_{22}$=A, S, or a conservative or nonconservative substitution of any of the foregoing;

$X_{23}$=A, G, or a conservative or nonconservative substitution of any of the foregoing;

$X_{24}$=A, a conservative or nonconservative substitution of any of the foregoing, or not present;

$X_{25}$=G, a conservative or nonconservative substitution of any of the foregoing, or not present;

$X_{26}$=A, H, C, or a conservative or nonconservative substitution of any of the foregoing;

$X_{27}$=A, Y, D, or a conservative or nonconservative substitution of any of the foregoing;

$X_{28}$=A, D, or a conservative or nonconservative substitution of any of the foregoing;

$X_{29}$=A, D, or a conservative or nonconservative substitution of any of the foregoing;

$X_{30}$=A, D, or a conservative or nonconservative substitution of any of the foregoing;

$X_{31}$=A or a conservative or nonconservative substitution thereof;

$X_{32}$=S, A, or a conservative or nonconservative substitution of any of the foregoing;

$X_{33}$=R, G, S, or a conservative or nonconservative substitution of any of the foregoing;

$X_{34}$=A, G, or a conservative substitution of any of the foregoing;

$X_{35}$=L, V, or a conservative substitution of any of the foregoing;

$X_{36}$=Y, A, or a conservative or nonconservative substitution of any of the foregoing;

$X_{37}$=A, T, or a conservative substitution of any of the foregoing;

$X_{38}$=C, S, or a conservative substitution of any of the foregoing;

$X_{39}$=E, D, or a conservative substitution of any of the foregoing;

$X_{40}$=E, D, or a conservative substitution of any of the foregoing;

$X_{41}$=A, T, or a conservative substitution of any of the foregoing;

$X_{42}$=D, E, or a conservative substitution of any of the foregoing;

$X_{43}$=D, G, or a conservative substitution of any of the foregoing;

$X_{44}$=D, or a conservative or nonconservative substitution of any of the foregoing or not present;

$X_{45}$=M, I, or a conservative substitution of any of the foregoing;

$X_{46}$=S, A, or a conservative substitution of any of the foregoing;

$X_{47}$=L, V, M, or a conservative substitution of any of the foregoing;

$X_{48}$=D, V, E, or a conservative or nonconservative substitution of any of the foregoing;

$X_{49}$=L, P, or a conservative or nonconservative substitution of any of the foregoing;

$X_{50}$=I, V, or a conservative substitution of any of the foregoing;

$X_{51}$=V, I, or a conservative substitution of any of the foregoing;

$X_{52}$=S, E, A, or a conservative or nonconservative substitution of any of the foregoing;

$X_{53}$=L, M, or a conservative substitution of any of the foregoing;

$X_{54}$=P, L, or a conservative or nonconservative substitution of any of the foregoing;

$X_{55}$=A, G, or a conservative substitution of any of the foregoing;

$X_{56}$=P, A, or a conservative or nonconservative substitution of any of the foregoing;

$X_{57}$=E, K, or a conservative substitution of any of the foregoing;

$X_{58}$=S, C, or a conservative substitution of any of the foregoing;

$X_{59}$=K, Q, or a conservative substitution of any of the foregoing;

$X_{60}$=V, T, or a conservative substitution of any of the foregoing;

$X_{61}$=M, V, or a conservative substitution of any of the foregoing;

$X_{62}$=T, A, or a conservative substitution of any of the foregoing;

$X_{63}$=F, V, S, or a conservative substitution of any of the foregoing;

$X_{64}$=D, N, or a conservative substitution of any of the foregoing;

$X_{65}$=N, R, or a conservative substitution of any of the foregoing;

$X_{66}$=H, Y, or a conservative substitution of any of the foregoing;

$X_{67}$=T, S, or a conservative substitution of any of the foregoing;

$X_{68}$=E, Q, or a conservative substitution of any of the foregoing;

$X_{69}$=F, H, or a conservative substitution of any of the foregoing;

$X_{70}$=A, T, or a conservative substitution of any of the foregoing;

$X_{71}$=N, T, or a conservative substitution of any of the foregoing;

$X_{72}$=Q, H, or a conservative substitution of any of the foregoing;

$X_{73}$=R, K, or a conservative substitution of any of the foregoing;

$X_{74}$=N, E, S, or a conservative substitution of any of the foregoing;

$X_{75}$=P, L, or a conservative or nonconservative substitution of any of the foregoing;

$X_{76}$=D, N, E, or a conservative substitution of any of the foregoing;

$X_{77}$=V, F, S, or a conservative substitution of any of the foregoing;

$X_{78}$=K, K, Q, or a conservative substitution of any of the foregoing;

$X_{79}$=R, H, Q, or a conservative substitution of any of the foregoing;

$X_{80}$=E, V, or a conservative or nonconservative substitution of any of the foregoing;

$X_{81}$=N, K, or a conservative substitution of any of the foregoing;

$X_{82}$=D, V, N, or a conservative or nonconservative substitution of any of the foregoing;

$X_{83}$=T, S, or a conservative substitution of any of the foregoing;

$X_{84}$=G, V, D, or a conservative or nonconservative substitution of any of the foregoing;

$X_{85}$=A, V, or a conservative substitution of any of the foregoing;

$X_{86}$=S, T, or a conservative substitution of any of the foregoing;

$X_{87}$=G, S, A, or a conservative substitution of any of the foregoing;

$X_{88}$=G, R, or a conservative or nonconservative substitution of any of the foregoing;

$X_{89}$=H, L, or a conservative or nonconservative substitution of any of the foregoing;

$X_{90}$=D, N, or a conservative substitution of any of the foregoing;

$X_{91}$=A, S, or a conservative substitution of any of the foregoing;

$X_{98}$=K, R, or a conservative substitution of any of the foregoing;

$X_{98}$=S, A, or a conservative substitution of any of the foregoing;

$X_{94}$=M, T, A, or a conservative or nonconservative substitution of any of the foregoing;

$X_{95}$=D, N, or a conservative substitution of any of the foregoing;

$X_{96}$=K, S, or a conservative substitution of any of the foregoing;

$X_{97}$=K, E, or a conservative substitution of any of the foregoing;

$X_{98}$=F, S, or a conservative or nonconservative substitution of any of the foregoing;

$X_{99}$=V, A, or a conservative substitution of any of the foregoing;

$X_{100}$=N, D, or a conservative substitution of any of the foregoing;

$X_{101}$=I, L, V, or a conservative substitution of any of the foregoing;

$X_{102}$=T, S, or a conservative substitution of any of the foregoing;

$X_{103}$=T, M, P, or a conservative or nonconservative substitution of any of the foregoing;

$X_{104}$=V, a conservative or nonconservative substitution of any of the foregoing, or not present;

$X_{105}$=K, a conservative or nonconservative substitution of any of the foregoing, or not present;

$X_{106}$=N, K, or a conservative substitution of any of the foregoing;

$X_{107}$=K, E, or a conservative substitution of any of the foregoing;

$X_{108}$=M, V, or a conservative substitution of any of the foregoing;

$X_{109}$=E, D, or a conservative substitution of any of the foregoing; and $X_{110}$=D, A, or a conservative or nonconservative substitution of any of the foregoing.

Nucleic acids encoding the above-referenced polypeptide can be designed using the genetic code. The above-referenced sequences for ZmFMT, SbFMT, and PvFMT can provide guidance. Exemplary conservative substitutions include substitutions among glycine, alanine, valine, leucine, and isoleucine; substitutions among serine, cysteine, threonine, and methionine; substitutions among phenylalanine, tyrosine, and tryptophan; substitutions among histidine, lysine, arginine; and substitutions among aspartate, glutamate, asparagine, and glutamine Other groupings of conservative substitutions are common in the art. Nonconservative substitutions are substitutions that are not conservative substitutions.

Nucleic acids encoding the aforementioned BAHD acyltransferases allow identification and isolation of related nucleic acids and their encoded enzymes that provide a means for production of altered lignins in plants.

For example, related nucleic acids can be isolated and identified by mutation of the SEQ ID NO:1, SEQ ID NO:3, or SEQ ID NO:5 sequence and/or by hybridization to DNA and/or RNA isolated from other plant species using SEQ ID NO:1, SEQ ID NO:3, or SEQ ID NO:5 nucleic acids as probes. The sequence of the feruloyl-CoA:monolignol transferase enzyme (e.g., SEQ ID NO:2, SEQ ID NO:4, SEQ ID NO:6, or SEQ ID NO:7) can also be examined and used a basis for designing alternative feruloyl-CoA:monolignol transferase nucleic acids that encode related feruloyl-CoA:monolignol transferase polypeptides.

In one embodiment, the BAHD acyltransferase nucleic acids of the invention include any nucleic acid that can selectively hybridize to SEQ ID NO:1, SEQ ID NO:3, or SEQ ID NO:5.

The term "selectively hybridize" includes hybridization, under stringent hybridization conditions, of a nucleic acid sequence to a specified nucleic acid target sequence (e.g., SEQ ID NO:1, SEQ ID NO:3, or SEQ ID NO:5) to a detectably greater degree (e.g., at least 2-fold over background) than its hybridization to non-target nucleic acid sequences. Such selective hybridization substantially excludes non-target nucleic acids. Selectively hybridizing sequences typically have about at least 40% sequence identity, or at least 50% sequence identity, or at least 60% sequence identity, or at least 70% sequence identity, or 60-99% sequence identity, or 70-99% sequence identity, or 80-99% sequence identity, or 90-95% sequence identity, or 90-99% sequence identity, or 95-97% sequence identity, or 97-99% sequence identity, or 100% sequence identity (or complementarity) with each other. In some embodiments, a selectively hybridizing sequence has at least about 70% or at least about 80% sequence identity or complementarity with SEQ ID NO:1, SEQ ID NO:3, or SEQ ID NO:5.

Thus, the nucleic acids of the invention include those with about 500 of the same nucleotides as SEQ ID NO:1, SEQ ID NO:3, or SEQ ID NO:5, or about 600 of the same nucleotides as SEQ ID NO:1, SEQ ID NO:3, or SEQ ID NO:5, or about 700 of the same nucleotides as SEQ ID NO:1, SEQ ID NO:3, or SEQ ID NO:5, or about 800 of the same nucleotides as SEQ ID NO:1, SEQ ID NO:3, or SEQ ID NO:5, or about 900 of the same nucleotides as SEQ ID NO:1, SEQ ID NO:3, or SEQ ID NO:5, or about 1000 of the same nucleotides as SEQ ID NO:1, SEQ ID NO:3, or SEQ ID NO:5, or about 1100 of the same nucleotides as SEQ ID NO:1, SEQ ID NO:3, or SEQ ID NO:5, or about 1200 of the same nucleotides as SEQ ID NO:1, SEQ ID NO:3, or SEQ ID NO:5, or about 1300 of the same nucleotides as SEQ ID NO:1, SEQ ID NO:3, or SEQ ID NO:5, or about 500-1325 of the same nucleotides as SEQ ID NO:1, SEQ ID NO:3, or SEQ ID NO:5. The identical nucleotides or amino acids can be distributed throughout the nucleic acid or the protein, and need not be contiguous.

Note that if a value of a variable that is necessarily an integer, e.g., the number of nucleotides or amino acids in a nucleic acid or protein, is described as a range, e.g., 90-99% sequence identity what is meant is that the value can be any integer between 90 and 99 inclusive, i.e., 90, 91, 92, 93, 94, 95, 96, 97, 98 or 99, or any range between 90 and 99 inclusive, e.g., 91-99%, 91-98%, 92-99%, etc.

The terms "stringent conditions" or "stringent hybridization conditions" include conditions under which a probe will hybridize to its target sequence to a detectably greater degree than other sequences (e.g., at least 2-fold over background). Stringent conditions are somewhat sequence-dependent and can vary in different circumstances. By controlling the stringency of the hybridization and/or washing conditions, target sequences can be identified with up to 100% complementarity to the probe (homologous probing). Alternatively, stringency conditions can be adjusted to allow some mismatching in sequences so that lower degrees of sequence similarity are detected (heterologous probing). The probe can be approximately 20-500 nucleotides in length, but can vary greatly in length from about 18 nucleotides to equal to the entire length of the target sequence. In some embodiments, the probe is about 10-50 nucleotides in length, or about 18-25 nucleotides in length, or about 18-50 nucleotides in length, or about 18-100 nucleotides in length.

Typically, stringent conditions will be those where the salt concentration is less than about 1.5 M Na ion (or other salts), typically about 0.01 to 1.0 M Na ion concentration (or other salts), at pH 7.0 to 8.3 and the temperature is at least about 30° C. for shorter probes (e.g., 10 to 50 nucleotides) and at least about 60° C. for longer probes (e.g., greater than 50 nucleotides). Stringent conditions may also be achieved with the addition of destabilizing agents such as formamide or Denhardt's solution. Exemplary low stringency conditions include hybridization with a buffer solution of 30 to 35% formamide, 1M NaCl, 1% SDS (sodium dodecyl sulfate) at 37° C., and a wash in 1×SSC to 2×SSC (where 20×SSC is 3.0 M NaCl, 0.3 M trisodium citrate) at 50 to 55° C. Exemplary moderate stringency conditions include hybridization in 40 to 45% formamide, 1M NaCl, 1% SDS at 37° C., and a wash in 0.5×SSC to 1×SSC at 55 to 60° C. Exemplary high stringency conditions include hybridization in 50% formamide, 1M NaCl, 1% SDS at 37° C., and a wash in 0.1×SSC at 60 to 65° C. Specificity is typically a function of post-hybridization washes, where the factors controlling hybridization include the ionic strength and temperature of the final wash solution.

For DNA-DNA hybrids, the $T_m$ can be approximated from the equation of Meinkoth and Wahl (Anal. Biochem. 138: 267-84 (1984)):

$T_m$=81.5° C.+16.6 (log M)+0.41 (% GC)−0.61 (% formamide)−500/L where M is the molarity of monovalent cations; % GC is the percentage of guanosine and cytosine nucleotides in the DNA, % formamide is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. The $T_m$ is reduced by about 1° C. for each 1% of mismatching. Thus, the $T_m$, hybridization and/or wash conditions can be adjusted to hybridize to sequences of the desired sequence identity. For example, if sequences with greater than or equal to 90% sequence identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can include hybridization and/or a wash at 1, 2, 3 or 4° C. lower than the thermal melting point ($T_m$). Moderately stringent conditions can include hybridization and/or a wash at 6, 7, 8, 9 or 10° C. lower than the thermal melting point ($T_m$). Low stringency conditions can include hybridization and/or a wash at 11, 12, 13, 14, 15 or 20° C. lower than the thermal melting point ($T_m$). Using the equation, hybridization and wash compositions, and a desired $T_m$, those of ordinary skill can identify and isolate nucleic acids with sequences related to SEQ ID NO:1, SEQ ID NO:3, or SEQ ID NO:5.

Those of skill in the art also understand how to vary the hybridization and/or wash solutions to isolate desirable nucleic acids. For example, if the desired degree of mismatching results in a $T_m$ of less than 45° C. (aqueous solution) or 32° C. (formamide solution) it is preferred to increase the SSC concentration so that a higher temperature can be used.

An extensive guide to the hybridization of nucleic acids is found in Tijssen, LABORATORY TECHNIQUES IN BIOCHEMISTRY AND MOLECULAR BIOLOGY—HYBRIDIZATION WITH NUCLEIC ACID PROBES, part 1, chapter 2, "Overview of principles of hybridization and the strategy of nucleic acid probe assays," Elsevier, N.Y. (1993); and in CURRENT PROTOCOLS IN MOLECULAR BIOLOGY, chapter 2, Ausubel, et al., eds, Greene Publishing and Wiley-Interscience, New York (1995).

Unless otherwise stated, in the present application high stringency is defined as hybridization in 4×SSC, 5×Denhardt's (5 g Ficoll, 5 g polyvinypyrrolidone, 5 g bovine serum albumin in 500 mL of water), 0.1 mg/mL boiled salmon sperm DNA, and 25 mM Na phosphate at 65° C., and a wash in 0.1×SSC, 0.1% SDS at 65° C.

The following terms are used to describe the sequence relationships between two or more nucleic acids or nucleic acids or polypeptides: (a) "reference sequence," (b) "comparison window," (c) "sequence identity," (d) "percentage of sequence identity" and (e) "substantial identity."

As used herein, "reference sequence" is a defined sequence used as a basis for sequence comparison. The reference sequence can be a nucleic acid sequence (e.g., SEQ ID NO:1, SEQ ID NO:3, or SEQ ID NO:5) or an amino acid sequence (e.g., SEQ ID NO:2, SEQ ID NO:4, SEQ ID NO:6, or SEQ ID NO:7). A reference sequence may be a subset or the entirety of a specified sequence. For example, a reference sequence may be a segment of a full-length cDNA or of a genomic DNA sequence, or the complete cDNA or complete genomic DNA sequence, or a domain of a polypeptide sequence.

As used herein, "comparison window" refers to a contiguous and specified segment of a nucleic acid or an amino acid sequence, wherein the nucleic acid/amino acid sequence can be compared to a reference sequence and wherein the portion of the nucleic acid/amino acid sequence in the comparison window may comprise additions or deletions (i.e., gaps) compared to the reference sequence (which does not comprise additions or deletions) for optimal alignment of the two sequences. The comparison window can vary for nucleic acid and polypeptide sequences. Generally, for nucleic acids, the comparison window is at least 20 contiguous nucleotides in length, and optionally can be 30, 40, 50, 100 or more nucleotides. For amino acid sequences, the comparison window is at least about 10 amino acids, and can optionally be 15, 20, 30, 40, 50, 100 or more amino acids. Those of skill in the art understand that to avoid a high similarity to a reference sequence due to inclusion of gaps in the nucleic acid or amino acid sequence, a gap penalty is typically introduced and is subtracted from the number of matches.

Methods of alignment of nucleotide and amino acid sequences for comparison are well known in the art. The local homology algorithm (BESTFIT) of Smith and Waterman, (1981) Adv. Appl. Math 2:482, may permit optimal alignment of compared sequences; by the homology alignment algorithm (GAP) of Needleman and Wunsch, (1970) J.

Mol. Biol. 48:443-53; by the search for similarity method (Tfasta and Fasta) of Pearson and Lipman, (1988) Proc. Natl. Acad. Sci. USA 85:2444; by computerized implementations of these algorithms, including, but not limited to: CLUSTAL in the PC/Gene program by Intelligenetics, Mountain View, Calif., GAP, BESTFIT, BLAST, FASTA and TFASTA in the Wisconsin Genetics Software Package, Version 8 (available from Genetics Computer Group (GCG™ programs (Accelrys, Inc., San Diego, Calif.)). The CLUSTAL program is well described by Higgins and Sharp (1988) Gene 73:237-44; Higgins and Sharp, (1989) CABIOS 5:151-3; Corpet, et al., (1988) Nucleic Acids Res. 16:10881-90; Huang, et al., (1992) Computer Applications in the Biosciences 8:155-65 and Pearson, et al., (1994) Meth. Mol. Biol. 24:307-31. An example of a good program to use for optimal global alignment of multiple sequences is PileUp (Feng and Doolittle, (1987) J. Mol. Evol., 25:351-60, which is similar to the method described by Higgins and Sharp, (1989) CABIOS 5:151-53 (and is hereby incorporated by reference). The BLAST family of programs that can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Current Protocols in Molecular Biology, Chapter 19, Ausubel, et al., eds., Greene Publishing and Wiley-Interscience, New York (1995). An updated version of the BLAST family of programs includes the BLAST+ suite. (Camacho, C., Coulouris, G., Avagyan, V., Ma, N, Papadopoulos J, Bealer K, Madden T L. BLAST+: architecture and applications. *BMC Bioinformatics.* 2009 Dec. 15; 10:421).

GAP uses the algorithm of Needleman and Wunsch, (1970) J. Mol. Biol. 48:443-53, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP makes a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package are 8 and 2, respectively. The gap creation and gap extension penalties can be expressed as an integer selected from the group of integers consisting of from 0 to 100. Thus, for example, the gap creation and gap extension penalties can be 0, 1, 2, 3, 4, 5, 6, 7, 8, 9, 10, 15, 20, 30, 40, 50 or more.

GAP presents one member of the family of best alignments. There may be many members of this family. GAP displays four figures of merit for alignments: Quality, Ratio, Identity and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see, Henikoff and Henikoff, (1989) Proc. Natl. Acad. Sci. USA 89:10915).

Sequence identity/similarity values provided herein can refer to the value obtained using the BLAST+2.5.0 suite of programs using default settings (blast.ncbi.nlm.nih.gov) (Camacho, C., Coulouris, G., Avagyan, V., Ma, N, Papadopoulos J, Bealer K, Madden T L. BLAST+: architecture and applications. *BMC Bioinformatics.* 2009 Dec. 15; 10:421).

As those of ordinary skill in the art will understand, BLAST searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, (1993) Comput. Chem. 17:149-63) and XNU ($C_1$-ayerie and States, (1993) Comput. Chem. 17:191-201) low-complexity filters can be employed alone or in combination.

The terms "substantial identity" indicates that a polypeptide or nucleic acid comprises a sequence with between 55-100% sequence identity to a reference sequence, with at least 55% sequence identity, or at least 60%, or at least 70%, or at least 80%, or at least 90% or at least 95% sequence identity or any percentage of value within the range of 55-100% sequence identity relative to the reference sequence over a specified comparison window. Optimal alignment may be ascertained or conducted using the homology alignment algorithm of Needleman and Wunsch, supra.

An indication that two polypeptide sequences are substantially identical is that both polypeptides have feruloyl-CoA:monolignol transferase activity, meaning that both polypeptides can synthesize monolignol ferulates from a monolignol and feruloyl-CoA. The polypeptide that is substantially identical to a feruloyl-CoA:monolignol transferase with a SEQ ID NO:2, SEQ ID NO:4, SEQ ID NO:6, or SEQ ID NO:7 sequence may not have exactly the same level of activity as the feruloyl-CoA:monolignol transferase with a SEQ ID NO:2, SEQ ID NO:4, SEQ ID NO:6, or SEQ ID NO:7. Instead, the substantially identical polypeptide may exhibit greater or lesser levels of feruloyl-CoA:monolignol transferase activity than the feruloyl-CoA:monolignol transferase with SEQ ID NO:2, SEQ ID NO:4, SEQ ID NO:6, or SEQ ID NO:7, as measured by assays available in the art or described herein (see, e.g., Example 1). For example, the substantially identical polypeptide can have at least about 40%, or at least about 50%, or at least about 60%, or at least about 70%, or at least about 80%, or at least about 90%, or at least about 95%, or at least about 97%, or at least about 98%, or at least about 100%, or at least about 105%, or at least about 110%, or at least about 120%, or at least about 130%, or at least about 140%, or at least about 150%, or at least about 200% of the activity of the feruloyl-CoA:monolignol transferase with the SEQ ID NO:2, SEQ ID NO:4, SEQ ID NO:6, or SEQ ID NO:7 sequence when measured by similar assay procedures.

Alternatively, substantial identity is present when second polypeptide is immunologically reactive with antibodies raised against the first polypeptide (e.g., a polypeptide with SEQ ID NO:2, SEQ ID NO:4, SEQ ID NO:6, or SEQ ID NO:7). Thus, a polypeptide is substantially identical to a first polypeptide, for example, where the two polypeptides differ only by a conservative substitution. In addition, a polypeptide can be substantially identical to a first polypeptide when they differ by a non-conservative change if the epitope that the antibody recognizes is substantially identical. Polypeptides that are "substantially similar" share sequences as noted above except that some residue positions, which are not identical, may differ by conservative amino acid changes.

The feruloyl-CoA:monolignol transferase polypeptides of the present invention may include the first 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and 99 N-terminal amino acid residues of a the SEQ ID NO:2, SEQ ID NO:4, SEQ ID NO:6, or SEQ ID NO:7 sequence. Alternatively, the feruloyl-CoA:monolignol transferase polypeptides of the present invention may include the first 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and 99 C-terminal amino acid residues of a the SEQ ID NO:2, SEQ ID NO:4, SEQ ID NO:6, or SEQ ID NO:7 sequence.

Lignin

Lignin broadly refers to a biopolymer that is typically part of secondary cell walls in plants. Lignin is a complex moderately cross-linked aromatic polymer (see, e.g., FIGS. 1A-1D). Lignin may also be covalently linked to hemicelluloses. Hemicellulose broadly refers to a class of branched sugar polymers composed of pentoses and hexoses. Hemicelluloses typically have an amorphous structure with up to hundreds or thousands of pentose units and they are generally at least partially soluble in dilute alkali. Cellulose broadly refers to an organic compound with the formula $(C_6H_{10}O_5)_z$ where z is an integer. Cellulose is a linear polysaccharide that can include linear chains of beta-1-4-linked glucose residues of several hundred to over ten thousand units.

Lignocellulosic biomass represents an abundant, inexpensive, and locally available feedstock for conversion to carbonaceous fuel (e.g., ethanol, biodiesel, biofuel and the like). However, the complex structure of lignin, which includes ether and carbon-carbon bonds that bind together the various subunits of lignin, and the crosslinking of lignin to other plant cell wall polymers, make it the most recalcitrant of plant polymers. Thus, significant quantities of lignin in a biomass can inhibit the efficient usage of plants as a source of fuels and other commercial products. Gaining access to the carbohydrate and polysaccharide polymers of plant cells for use as carbon and energy sources therefore requires significant energy input and often harsh chemical treatments, especially when significant amounts of lignin are present. For example, papermaking procedures in which lignin is removed from plant fibers by delignification reactions are typically expensive, can be polluting and generally require use of high temperatures and harsh chemicals largely because the structure of lignin is impervious to mild conditions. Plants with altered lignin structures that could be more readily cleaved under milder conditions would reduce the costs of papermaking and make the production of biofuels more competitive with currently existing procedures for producing oil and gas fuels.

Plants make lignin from a variety of subunits or monomers that are generally termed monolignols. Such primary monolignols include p-coumaryl alcohol, coniferyl alcohol, and sinapyl alcohol.

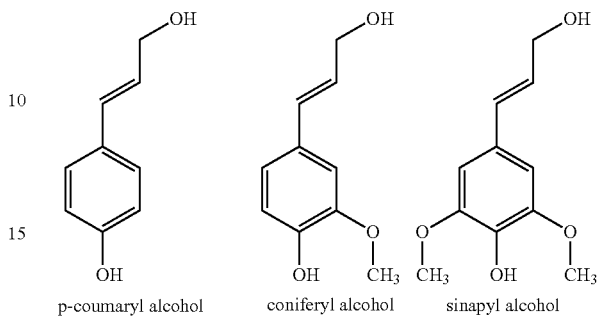

p-coumaryl alcohol   coniferyl alcohol   sinapyl alcohol

Monolignols destined for lignin polymerization in normal plants can be preacylated with acetate, p-hydroxybenzoate, or p-coumarate (Ralph et al., *Phytochem. Rev.* 3:29-60 (2004)). p-Coumarates can acylate the γ-position of phenylpropanoid side chains mainly found in the syringyl units of lignin. Studies indicate that monolignols, primarily sinapyl alcohol, are enzymatically preacylated with p-coumarate prior to their incorporation into lignin, indicating that the monolignol p-coumarate conjugates, coniferyl p-coumarate and sinapyl p-coumarate, can also be 'monomer' precursors of lignin.

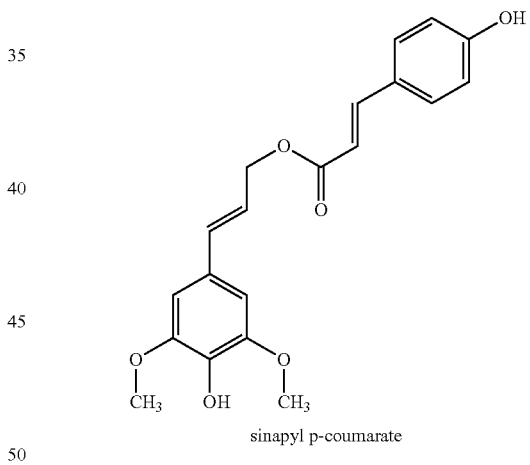

sinapyl p-coumarate

While monolignol p-coumarate-derived units may comprise up to 40% of the lignin in some grass tissues, the p-coumarate moiety from such conjugates does not enter into the radical coupling (polymerization) reactions occurring during lignifications. Instead, the p-coumarate moieties substantially remain as terminal units with an unsaturated side chain and a free phenolic group (Ralph et al., *J. Am. Chem. Soc.* 116: 9448-9456 (1994); Hatfield et al., *J. Sci. Food Agric.* 79: 891-899 (1999)). Thus, the presence of sinapyl p-coumarate conjugates produces a lignin 'core' with terminal p-coumarate groups and no new bonds in the backbone of the lignin polymer, resulting in a lignin that is not significantly more easily cleaved.

In contrast to p-coumarate, ferulate esters do undergo radical coupling reactions under lignification conditions. Model ferulates, such as the ferulate shown below (where R is $CH_3$—, $CH_3$—$CH_2$—, a sugar, a polysaccharide, pectin, cell-wall (arabino)xylan or other plant component), readily undergo radical coupling reactions with each other and with lignin monomers and oligomers to form cross-linked networks.

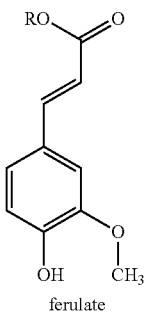
ferulate

If present during lignification, ferulates can become inextricably bound into the lignin by ether and C—C bonds. Although such ferulate moieties are no more extractable or cleavable from the lignin structure than other lignin units under most conditions, the ester itself can be readily cleaved using conditions generally employed for ester cleavage. Upon cleavage of such ester bonds, other plant cell wall components can be released. For example, an arabinoxylan (hemicellulose) chain can be released from a ferulate-mediated lignin attachment by cleaving the ester.

Ferulate-monolignol ester conjugates, such as coniferyl ferulate or sinapyl ferulate, are made by plants as secondary metabolites during, among other things, lignin biosynthesis. [Paula et al, *Tetrahedron* 51: 12453-12462 (1994); Seca et al., *Phytochemistry* 56: 759-767 (2001); Hsiao & Chiang, *Phytochemistry* 39: 899-902 (1995); Li et al., *Planta Med.* 72: 278-280 (2005)]. The structures of coniferyl ferulate and sinapyl ferulate are shown below.

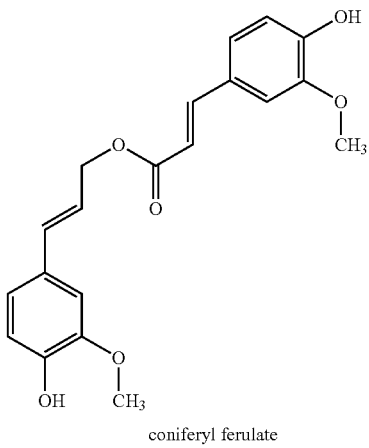
coniferyl ferulate

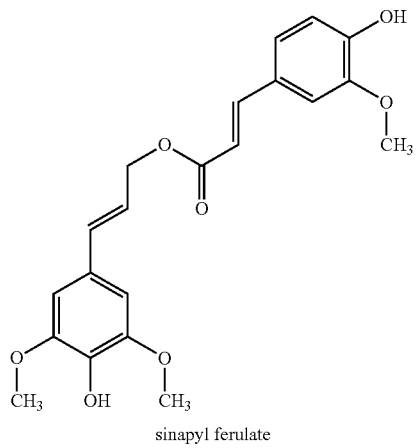
sinapyl ferulate

For example, the feruloyl-CoA:monolignol transferases provided herein biosynthesize coniferyl ferulate from coniferyl alcohol and feruloyl-CoA as shown below.

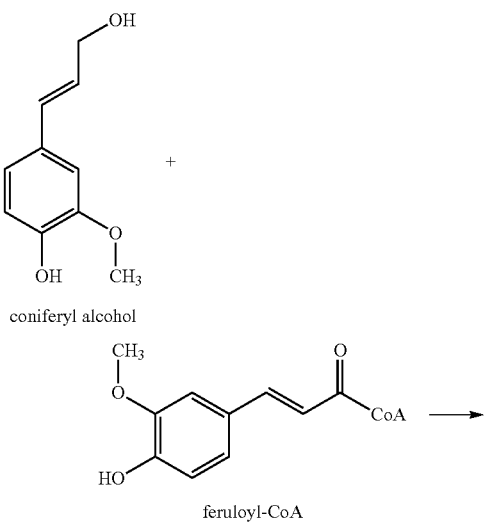

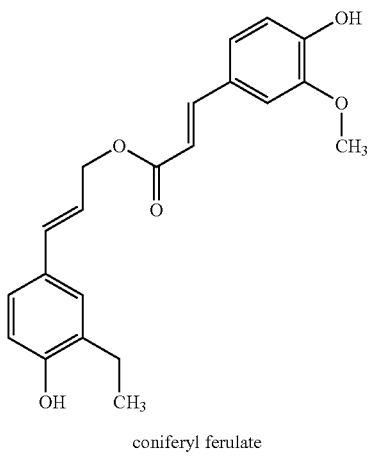
coniferyl ferulate

The incorporation of monolignol ferulates into the lignin of plants allows the cell wall materials and lignin to be readily cleaved or processed into useful products. See also, U.S. Pat.

Nos. 9,441,235, 9,487,794, and 9,493,783, the contents of all of which are specifically incorporated herein by reference in their entireties.

The monolignol ferulates made by the methods and feruloyl-CoA:monolignol transferases provided herein can be incorporated by radical coupling into plant lignins. Both the monolignol and the ferulate moieties can undergo such coupling, resulting in a lignin that can be complex. However, such 'double-ended-incorporation' still yields readily cleavable ester linkages that have been engineered into the backbone of the lignin polymer network. Esters are readily cleaved under much less stringent conditions by the same chemical processes used to cleave lignin, but the lignin resulting from the methods described herein is significantly easier to cleave, and provides more facile and less costly access to the plant cell wall polysaccharides. See also, U.S. Pat. Nos. 9,441,235, 9,487,794, and 9,493,783, the contents of all of which are specifically incorporated herein by reference in their entireties.

Lignins can be degraded by chemical or enzymatic means to yield a variety of smaller monomers and oligomers. While enzymatic processes are generally preferred because they do not require high temperatures and harsh chemicals, such enzymatic processes have previously not been as effective at solubilizing lignin moieties away from valuable plant cell constituents (e.g., polysaccharides and carbohydrates).

According to the invention, plants with the feruloyl-CoA:monolignol transferase nucleic acids and/or enzymes described herein supply monolignol ferulates for facile lignification in plants, thereby yielding plants with lignins that are more readily cleaved or processed to release cellulose, hemicelluloses and lignin breakdown products.

Conditions for releasing the cellulose, hemicelluloses and lignin breakdown products from plants containing the feruloyl-CoA:monolignol transferase nucleic acids and/or enzymes described herein include conditions typically employed for cleaving ester bonds. Thus, the ester bonds within monolignol ferulate-rich lignins can be cleaved by milder alkaline and/or acidic conditions than the conditions typically used to break down the lignin of plants that are not rich in monolignol ferulates. For example, mildly alkaline conditions involving use of ammonia may be used to cleave the ester bonds within monolignol ferulate-rich lignins, whereas such conditions would not cleave substantially any of the ether and carbon-carbon bonds in normal lignins. See also, U.S. patent application Ser. No. 12/830,905, filed Jul. 6, 2010 and to U.S. Patent Application Ser. No. 61/213,706, filed Jul. 6, 2009, the contents of both of which are specifically incorporated herein by reference in their entireties.

For acid digestion, exemplary methods include but are not limited to acid γ-valerolactone acid digestion (Luterbacher, J. S., Azarpira, A., Motagamwala, A. H., Lu, F., Ralph, J., and Dumesic, J. A. Aromatic monomer production integrated into the γ-valerolactone sugar platform. (2015) *Energy and Environmental Science* 8(9), 2657-2663), digestion as described in Santoro et al. (Santoro, N., Cantu, S. L., Tornqvist, C. E., Falbel, T. G., Bolivar, J. L., Patterson, S. E., Pauly, M., and Walton, J. D. A high-throughput platform for screening milligram quantities of plant biomass for lignocellulose digestibility. (2010) *Bioenergy Research* 3(1), 93-102), and ionic digestion (Kim, K. H., Dutta, T., Ralph, J., Mansfield, S. D., Simmons, B. A., and Singh, S. Impact of lignin polymer backbone esters on ionic liquid pretreatment of poplar. (2017) Biotechnology for Biofuels).

Plants Modified to Contain a Feruloyl-CoA:Monolignol Transferase

In order to engineer plants with lignins that contain significant levels of monolignol ferulates, one of skill in the art can introduce feruloyl-CoA:monolignol transferases or nucleic acids encoding such feruloyl-CoA:monolignol transferases into the plants. For example, one of skill in the art can inject feruloyl-CoA:monolignol transferase enzymes into young plants.

Alternatively, one of skill in the art can generate genetically-modified plants that contain nucleic acids encoding feruloyl-CoA:monolignol transferases within their somatic and/or germ cells. Such genetic modification can be accomplished by procedures available in the art. For example, one of skill in the art can prepare an expression cassette or expression vector that can express one or more encoded feruloyl-CoA:monolignol transferase enzymes. Plant cells can be transformed by the expression cassette or expression vector, and whole plants (and their seeds) can be generated from the plant cells that were successfully transformed with the feruloyl-CoA:monolignol transferase nucleic acids. Some procedures for making such genetically modified plants and their seeds are described below.

Promoters: The feruloyl-CoA:monolignol transferase nucleic acids of the invention can be operably linked to a promoter, which provides for expression of mRNA from the feruloyl-CoA:monolignol transferase nucleic acids. The promoter is typically a promoter functional in plants and/or seeds, and can be a promoter functional during plant growth and development. A feruloyl-CoA:monolignol transferase nucleic acid is operably linked to the promoter when it is located downstream from the promoter, to thereby form an expression cassette.

Most endogenous genes have regions of DNA that are known as promoters, which regulate gene expression. Promoter regions are typically found in the flanking DNA upstream from the coding sequence in both prokaryotic and eukaryotic cells. A promoter sequence provides for regulation of transcription of the downstream gene sequence and typically includes from about 50 to about 2,000 nucleotide base pairs. Promoter sequences also contain regulatory sequences such as enhancer sequences that can influence the level of gene expression. Some isolated promoter sequences can provide for gene expression of heterologous DNAs, that is a DNA different from the native or homologous DNA.

Promoter sequences are also known to be strong or weak, or inducible. A strong promoter provides for a high level of gene expression, whereas a weak promoter provides for a very low level of gene expression. An inducible promoter is a promoter that provides for the turning on and off of gene expression in response to an exogenously added agent, or to an environmental or developmental stimulus. For example, a bacterial promoter such as the $P_{tac}$ promoter can be induced to vary levels of gene expression depending on the level of isothiopropylgalactoside added to the transformed cells. Promoters can also provide for tissue specific or developmental regulation. An isolated promoter sequence that is a strong promoter for heterologous DNAs is advantageous because it provides for a sufficient level of gene expression for easy detection and selection of transformed cells and provides for a high level of gene expression when desired.

Suitable promoters for use in the present invention include native or heterologous promoters.

Expression cassettes generally include, but are not limited to, a plant promoter such as the CaMV 35S promoter (Odell et al., *Nature*. 313:810-812 (1985)), or others such as CaMV 19S (Lawton et al., *Plant Molecular Biology.* 9:315-324 (1987)), nos (Ebert et al., *Proc. Natl. Acad. Sci. USA.* 84:5745-5749 (1987)), Adh1 (Walker et al., *Proc. Natl. Acad. Sci. USA.* 84:6624-6628 (1987)), sucrose synthase (Yang et al., *Proc. Natl. Acad. Sci. USA.* 87:4144-4148 (1990)), α-tubulin, ubiquitin, actin (Wang et al., *Mol. Cell. Biol.* 12:3399 (1992)), cab (Sullivan et al., *Mol. Gen. Genet.* 215:431 (1989)), PEPCase (Hudspeth et al., *Plant Molecular Biology.* 12:579-589 (1989)) or those associated with the R gene complex (Chandler et al., *The Plant Cell.* 1:1175-1183 (1989)). Further suitable promoters include the poplar xylem-specific secondary cell wall specific cellulose synthase 8 promoter, cauliflower mosaic virus promoter, the Z10 promoter from a gene encoding a 10 kD zein protein, a Z27 promoter from a gene encoding a 27 kD zein protein, inducible promoters, such as the light inducible promoter derived from the pea rbcS gene (Coruzzi et al., *EMBO J.* 3:1671 (1971)) and the actin promoter from rice (McElroy et al., *The Plant Cell.* 2:163-171 (1990)). Seed specific promoters, such as the phaseolin promoter from beans, may also be used (Sengupta-Gopalan, *Proc. Natl. Acad. Sci. USA.* 83:3320-3324 (1985). Further suitable promoters include any of the promoters on the various genes of the conventional lignin monomer (monolignol) biosynthetic pathway. See, e.g., Vanholme et al. 2012 (Vanholme, R., Morreel, K., Darrah, C., Oyarce, P., Grabber, J. H., Ralph, J., and Boerjan, W. Metabolic engineering of novel lignin in biomass crops. (2012) *New Phytol.* 196(4), 978-1000); Vanholme et al. 2010 (Vanholme, R., Demedts, B., Morreel, K., Ralph, J., and Boerjan, W. Lignin biosynthesis and structure. (2010) *Plant Physiol.* 153(3), 895-905), Vanholme et al. 2008 (Vanholme, R., Morreel, K., Ralph, J., and Boerjan, W. Lignin engineering. (2008) *Curr. Opin. Plant Biol.* 11(3), 278-285), Voerjan et al. 2003 (Boerjan, W., Ralph, J., and Baucher, M. Lignin biosynthesis. (2003) Annual Reviews in Plant Biology 54, 519-546). An exemplary promoter from this pathway is the cinnamate-4-hydroxylase (C4H) promoter (Bell-Lelong, D. A., Cusumano, J. C., Meyer, K., and Chapple, C. Cinnamate-4-hydroxylase expression in *Arabidopsis*: regulation in response to development and the environment. (1997) *Plant Physiol.* 113, 729-738), the sequence of which is SEQ ID NO:8:

aagcttagaggagaaactgagaaaatcagcgtaatgagagacgagagca atgtgctaagagaagagattgggaagagagaagagacgataaaggaaac ggaaaagcatatggaggagcttcatatggagcaagtgaggctgagaaga cggtcgagtgagcttacggaagaagtggaaaggacgagagtgtctgcat cggaaatggctgagcagaaagagaagctataagacagctttgtatgtc tcttgaccattacagagatgggtacgacaggctttggagagttgttgcc ggccataagagtaagagagtagtggttttaacaacttgaagtgtaagaa caatgagtcaatgactacgtgcaggacattggacataccgtgtgttctt ttggattgaaatgttgtttcgaagggctgttagttgatgttgaaaatag gttgaagttgaataatgcatgttgatatagtaaatatcaatggtaatat tttctcatttcccaaaactcaaatgatatcatttaattataaactaacg taaactgttgacaatacacttatggttaaaaatttggagtcttgtttta gtatacgtatcaccaccgcacggtttcaaaaccacataattgtaaatgt tattggaaaaaagaacccgcaatacgtattgtattttggtaaacatagc tctaagcctctaatatataagctctcaacaattctggctaatggtccca agtaagaaaagcccatgtattgtaaggtcatgatctcaaaaacgagggt gaggtggaatactaacatgaggagaaagtaaggtgacaaattttttgggg caatagtggtggatatggtggggaggtaggtagcatcatttctccaagt cgctgtctttcgtggtaatggtaggtgtgtctctctttatattatttat tactactcattgttaatttcttttttctacaatttttcttactcca aaatacgtcacaaatataatactaggcaaataatttatttaattgtaagt caatagagtggttgttgtaaaattgattttgatattgaaagagttcat ggacggatgtgtatgcgccaaatgctaagcccttgtagtcttgtactgt gccgcgcgtatattttaaccaccactagttgtttctcttttcaaaaac acacaaaaaataatttgttttcgtaacggcgtcaaatctgacggcgtct caatacgttcaatttttcttcttcacatggtttctcatagctttgc attgaccataggtaaagggataaggataaaggttttttctcttgtttgt tttatcttattattcaaaatggataaaaaaacagtcttattttgattt ctttgattaaaaaagtcattgaaattcatatttgattttttgctaaatg tcaactcagagacacaaacgtaatgcactgtcgccaatattcatggatc atgaccatgaatatcactagaataattgaaaatcagtaaaatgcaaaca aagcattttctaattaaaacagtcttctacattcacttaattggaattt cctttatcaaacccaaagtccaaaacaatcggcaatgtttttgcaaatg ttcaaaactattggcgggttggtctatccgaattgaagatcttttctcc atatgatagaccaacgaaattcggcatacgtgtttttttttttgttttg aaaacccttttaaacaaccttaattcaaaatactaatgtaactttattga acgtgcatctaaaaattttgaactttgcttttgagaaataatcaatgta ccaataaagaagatgtagtacatacattataattaaatacaaaaaagga atcaccatatagtacatggtagacaatgaaaaactttaaaacatataca atcaataatactctttgtgcataactttttttgtcgtctcgagtttata tttgagtacttatacaaactattagattacaaactgtgctcagatacat taagttaatcttatatacaagagcactcgagtgttgtccttaagttaat cttaagatatcttgaggtaaatagaaatagttaactcgttttattttc ttttttttaccatgagcaaaaaagatgaagtaagttcaaaacgtgacg aatctacatgttactacttagtatgtgtcaatcattaaatcgggaaaac ttcatcatttcaggagtactacaaaactcctaagagtgagaacgactac atagtacatattttgataaaagacttgaaaacttgctaaaacgaatttg cgaaaatataatcatacaagtagaaccactgatttgatcgaattattca tagcttttgtaggatgaacttaactaaataatatctcacaaaagtattga cagtaacctagtactatactatctatgttagaatgattatgatataa tttatcccctcacttattcatatgattttttgaagcaactactttcgttt ttttaacattttcttttttggtttttgttaatgaacatatttagtcgtt tcttaattccactcaaatagaaaatacaagagaacttttatttaataga tatgaacataatctcacatcctcctcctaccttcaccaaacacttttac

```
-continued
atacactttgtggtctttctttacctaccaccatcaacaacaacaccaa gccccactcacacacacgcaatcacgttaaatctaacgccgtttattat ctcatcattcaccaactcccacgtacctaacgccgtttaccttttgccg ttggtcctcatttctcaaaccaaccaaacctctccctcttataaaatcc tctctcccttctttatttcttcctcagcagcttcttctgctttcaatta ctctcgccgacgattttctcaccggaaaaaaacaatatcattgcggata cacaaactata
```

Other promoters useful in the practice of the invention are known to those of skill in the art.

Alternatively, novel tissue specific promoter sequences may be employed in the practice of the present invention. cDNA clones from a particular tissue can be isolated and those clones which are expressed specifically in that tissue are identified, for example, using Northern blotting. Preferably, the gene isolated not present in a high copy number, but is relatively abundant in specific tissues. The promoter and control elements of corresponding genomic clones can then be localized using techniques well known to those of skill in the art.

A feruloyl-CoA:monolignol transferase nucleic acid can be combined with the promoter by standard methods to yield an expression cassette, for example, as described in Sambrook et al. (MOLECULAR CLONING: A LABORATORY MANUAL. Second Edition (Cold Spring Harbor, N.Y.: Cold Spring Harbor Press (1989); MOLECULAR CLONING: A LABORATORY MANUAL. Third Edition (Cold Spring Harbor, N.Y.: Cold Spring Harbor Press (2000)). Briefly, a plasmid containing a promoter such as the 35S CaMV promoter can be constructed as described in Jefferson (*Plant Molecular Biology Reporter* 5:387-405 (1987)) or obtained from Clontech Lab in Palo Alto, Calif. (e.g., pBI121 or pBI221). Typically, these plasmids are constructed to have multiple cloning sites having specificity for different restriction enzymes downstream from the promoter. The feruloyl-CoA:monolignol transferase nucleic acids can be subcloned downstream from the promoter using restriction enzymes and positioned to ensure that the DNA is inserted in proper orientation with respect to the promoter so that the DNA can be expressed as sense RNA. Once the feruloyl-CoA:monolignol transferase nucleic acid is operably linked to a promoter, the expression cassette so formed can be subcloned into a plasmid or other vector (e.g., an expression vector).

In some embodiments, a cDNA clone encoding a feruloyl-CoA:monolignol transferase protein is isolated from *Angelica sinensis* tissue, for example, a root tissue. In other embodiments, cDNA clones from other species (that encode a feruloyl-CoA:monolignol transferase protein) are isolated from selected plant tissues, or a nucleic acid encoding a mutant or modified feruloyl-CoA:monolignol transferase protein is prepared by available methods or as described herein. For example, the nucleic acid encoding a mutant or modified feruloyl-CoA:monolignol transferase protein can be any nucleic acid with a coding region that hybridizes to SEQ ID NO:1, SEQ ID NO:3, or SEQ ID NO:5 and that has feruloyl-CoA:monolignol transferase activity. Using restriction endonucleases, the entire coding sequence for the feruloyl-CoA:monolignol transferase is subcloned downstream of the promoter in a 5' to 3' sense orientation.

Targeting Sequences: Additionally, expression cassettes can be constructed and employed to target the feruloyl-CoA:monolignol transferase nucleic acids to an intracellular compartment within plant cells or to direct an encoded protein to the extracellular environment. This can generally be achieved by joining a DNA sequence encoding a transit or signal peptide sequence to the coding sequence of the feruloyl-CoA:monolignol transferase nucleic acid. The resultant transit, or signal, peptide will transport the protein to a particular intracellular, or extracellular destination, respectively, and can then be posttranslational removed. Transit peptides act by facilitating the transport of proteins through intracellular membranes, e.g., vacuole, vesicle, plastid and mitochondrial membranes, whereas signal peptides direct proteins through the extracellular membrane. By facilitating transport of the protein into compartments inside or outside the cell, these sequences can increase the accumulation of a particular gene product in a particular location. For example, see U.S. Pat. No. 5,258,300.

3' Sequences: When the expression cassette is to be introduced into a plant cell, the expression cassette can also optionally include 3' nontranslated plant regulatory DNA sequences that act as a signal to terminate transcription and allow for the polyadenylation of the resultant mRNA. The 3' nontranslated regulatory DNA sequence preferably includes from about 300 to 1,000 nucleotide base pairs and contains plant transcriptional and translational termination sequences. For example, 3' elements that can be used include those derived from the nopaline synthase gene of *Agrobacterium tumefaciens* (Bevan et al., *Nucleic Acid Research.* 11:369-385 (1983)), or the terminator sequences for the T7 transcript from the octopine synthase gene of *Agrobacterium tumefaciens*, and/or the 3' end of the protease inhibitor I or II genes from potato or tomato. Other 3' elements known to those of skill in the art can also be employed. These 3' nontranslated regulatory sequences can be obtained as described in An (*Methods in Enzymology.* 153:292 (1987)). Many such 3' nontranslated regulatory sequences are already present in plasmids available from commercial sources such as Clontech, Palo Alto, Calif. The 3' nontranslated regulatory sequences can be operably linked to the 3' terminus of the feruloyl-CoA:monolignol transferase nucleic acids by standard methods.

Selectable and Screenable Marker Sequences: In order to improve identification of transformants, a selectable or screenable marker gene can be employed with the expressible feruloyl-CoA:monolignol transferase nucleic acids. "Marker genes" are genes that impart a distinct phenotype to cells expressing the marker gene and thus allow such transformed cells to be distinguished from cells that do not have the marker. Such genes may encode either a selectable or screenable marker, depending on whether the marker confers a trait which one can 'select' for by chemical means, i.e., through the use of a selective agent (e.g., a herbicide, antibiotic, or the like), or whether it is simply a trait that one can identify through observation or testing, i.e., by 'screening' (e.g., the R-locus trait). Of course, many examples of suitable marker genes are known to the art and can be employed in the practice of the invention.

Included within the terms selectable or screenable marker genes are also genes which encode a "secretable marker" whose secretion can be detected as a means of identifying or selecting for transformed cells. Examples include markers which encode a secretable antigen that can be identified by antibody interaction, or secretable enzymes that can be detected by their catalytic activity. Secretable proteins fall into a number of classes, including small, diffusible proteins detectable, e.g., by ELISA; and proteins that are inserted or trapped in the cell wall (e.g., proteins that include a leader sequence such as that found in the expression unit of extensin or tobacco PR-S).

With regard to selectable secretable markers, the use of a gene that encodes a polypeptide that becomes sequestered in the cell wall, where the polypeptide includes a unique epitope may be advantageous. Such a secreted antigen marker can employ an epitope sequence that would provide low background in plant tissue, a promoter-leader sequence that imparts efficient expression and targeting across the plasma membrane, and can produce protein that is bound in the cell wall and yet is accessible to antibodies. A normally secreted wall protein modified to include a unique epitope would satisfy such requirements.

Example of proteins suitable for modification in this manner include extensin or hydroxyproline rich glycoprotein (HPRG). For example, the maize HPRG (Stiefel et al., *The Plant Cell.* 2:785-793 (1990)) is well characterized in terms of molecular biology, expression, and protein structure and therefore can readily be employed. However, any one of a variety of extensins and/or glycine-rich wall proteins (Keller et al., *EMBO J.* 8:1309-1314 (1989)) could be modified by the addition of an antigenic site to create a screenable marker.

Numerous other possible selectable and/or screenable marker genes will be apparent to those of skill in the art in addition to the one set forth herein below. Therefore, it will be understood that the discussion herein is exemplary rather than exhaustive. In light of the techniques disclosed herein and the general recombinant techniques that are known in the art, the present invention readily allows the introduction of any gene, including marker genes, into a recipient cell to generate a transformed plant cell, e.g., a monocot cell or dicot cell.

Possible selectable markers for use in connection with the present invention include, but are not limited to, a neo gene (Potrykus et al., *Mol. Gen. Genet.* 199:183-188 (1985)) which codes for kanamycin resistance and can be selected for using kanamycin, G418, and the like; a bar gene which codes for bialaphos resistance; a gene which encodes an altered EPSP synthase protein (Hinchee et al., *Bio/Technology.* 6:915-922 (1988)) thus conferring glyphosate resistance; a nitrilase gene such as bxn from *Klebsiella ozaenae* which confers resistance to bromoxynil (Stalker et al., *Science.* 242:419-423 (1988)); a mutant acetolactate synthase gene (ALS) which confers resistance to imidazolinone, sulfonylurea or other ALS-inhibiting chemicals (European Patent Application 154,204 (1985)); a methotrexate-resistant DHFR gene (Thillet et al., *J. Biol. Chem.* 263:12500-12508 (1988)); a dalapon dehalogenase gene that confers resistance to the herbicide dalapon; or a mutated anthranilate synthase gene that confers resistance to 5-methyl tryptophan. Where a mutant EPSP synthase gene is employed, additional benefit may be realized through the incorporation of a suitable chloroplast transit peptide, CTP (European Patent Application 0 218 571 (1987)).

An illustrative embodiment of a selectable marker gene capable of being used in systems to select transformants is the gene that encode the enzyme phosphinothricin acetyltransferase, such as the bar gene from *Streptomyces hygroscopicus* or the pat gene from *Streptomyces viridochromogenes* (U.S. Pat. No. 5,550,318). The enzyme phosphinothricin acetyl transferase (PAT) inactivates the active ingredient in the herbicide bialaphos, phosphinothricin (PPT). PPT inhibits glutamine synthetase, (Murakami et al., *Mol. Gen. Genet.* 205:42-50 (1986); Twell et al., *Plant Physiol.* 91:1270-1274 (1989)) causing rapid accumulation of ammonia and cell death. The success in using this selective system in conjunction with monocots was surprising because of the major difficulties that have been reported in transformation of cereals (Potrykus, *Trends Biotech.* 7:269-273 (1989)).

Screenable markers that may be employed include, but are not limited to, a (3-glucuronidase or uidA gene (GUS) that encodes an enzyme for which various chromogenic substrates are known; an R-locus gene, which encodes a product that regulates the production of anthocyanin pigments (red color) in plant tissues (Dellaporta et al., In: *Chromosome Structure and Function: Impact of New Concepts,* 18$^{th}$ Stadler Genetics Symposium, J. P. Gustafson and R. Appels, eds. (New York: Plenum Press) pp. 263-282 (1988)); a β-lactamase gene (Sutcliffe, *Proc. Natl. Acad. Sci. USA.* 75:3737-3741 (1978)), which encodes an enzyme for which various chromogenic substrates are known (e.g., PADAC, a chromogenic cephalosporin); a xylE gene (Zukowsky et al., *Proc. Natl. Acad. Sci. USA.* 80:1101 (1983)) which encodes a catechol dioxygenase that can convert chromogenic catechols; an α-amylase gene (Ikuta et al., *Bio/technology* 8:241-242 (1990)); a tyrosinase gene (Katz et al., *J. Gen. Microbiol.* 129:2703-2714 (1983)) which encodes an enzyme capable of oxidizing tyrosine to DOPA and dopaquinone which in turn condenses to form the easily detectable compound melanin; a β-galactosidase gene, which encodes an enzyme for which there are chromogenic substrates; a luciferase (lux) gene (Ow et al., *Science.* 234:856-859.1986), which allows for bioluminescence detection; or an aequorin gene (Prasher et al., *Biochem. Biophys. Res. Comm.* 126:1259-1268 (1985)), which may be employed in calcium-sensitive bioluminescence detection, or a green or yellow fluorescent protein gene (Niedz et al., *Plant Cell Reports.* 14:403 (1995)).

For example, genes from the maize R gene complex can be used as screenable markers. The R gene complex in maize encodes a protein that acts to regulate the production of anthocyanin pigments in most seed and plant tissue. Maize strains can have one, or as many as four, R alleles that combine to regulate pigmentation in a developmental and tissue specific manner A gene from the R gene complex does not harm the transformed cells. Thus, an R gene introduced into such cells will cause the expression of a red pigment and, if stably incorporated, can be visually scored as a red sector. If a maize line carries dominant alleles for genes encoding the enzymatic intermediates in the anthocyanin biosynthetic pathway (C2, A1, A2, Bz1 and Bz2), but carries a recessive allele at the R locus, transformation of any cell from that line with R will result in red pigment formation. Exemplary lines include Wisconsin 22 that contains the rg-Stadler allele and TR112, a K55 derivative that is r-g, b, Pl. Alternatively any genotype of maize can be utilized if the C1 and R alleles are introduced together.

The R gene regulatory regions may be employed in chimeric constructs in order to provide mechanisms for controlling the expression of chimeric genes. More diversity of phenotypic expression is known at the R locus than at any other locus (Coe et al., in *Corn and Corn Improvement,* eds. Sprague, G. F. & Dudley, J. W. (Am. Soc. Agron., Madison, Wis.), pp. 81-258 (1988)). It is contemplated that regulatory regions obtained from regions 5' to the structural R gene can be useful in directing the expression of genes, e.g., insect resistance, drought resistance, herbicide tolerance or other protein coding regions. For the purposes of the present invention, it is believed that any of the various R gene family members may be successfully employed (e.g., P, S, Lc, etc.). However, one that can be used is Sn (particularly Sn:bol3).

Sn is a dominant member of the R gene complex and is functionally similar to the R and B loci in that Sn controls the tissue specific deposition of anthocyanin pigments in certain seedling and plant cells, therefore, its phenotype is similar to R.

A further screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It is also envisioned that this system may be developed for population screening for bioluminescence, such as on tissue culture plates, or even for whole plant screening.

Other Optional Sequences: An expression cassette of the invention can also further comprise plasmid DNA. Plasmid vectors include additional DNA sequences that provide for easy selection, amplification, and transformation of the expression cassette in prokaryotic and eukaryotic cells, e.g., pUC-derived vectors such as pUC8, pUC9, pUC18, pUC19, pUC23, pUC119, and pUC120, pSK-derived vectors, pGEM-derived vectors, pSP-derived vectors, or pBS-derived vectors. The additional DNA sequences include origins of replication to provide for autonomous replication of the vector, additional selectable marker genes, preferably encoding antibiotic or herbicide resistance, unique multiple cloning sites providing for multiple sites to insert DNA sequences or genes encoded in the expression cassette and sequences that enhance transformation of prokaryotic and eukaryotic cells.

Another vector that is useful for expression in both plant and prokaryotic cells is the binary Ti plasmid (as disclosed in Schilperoort et al., U.S. Pat. No. 4,940,838) as exemplified by vector pGA582. This binary Ti plasmid vector has been previously characterized by An (*Methods in Enzymology.* 153:292 (1987)) and is available from Dr. An. This binary Ti vector can be replicated in prokaryotic bacteria such as *E. coli* and *Agrobacterium*. The *Agrobacterium* plasmid vectors can be used to transfer the expression cassette to dicot plant cells, and under certain conditions to monocot cells, such as rice cells. The binary Ti vectors preferably include the nopaline T DNA right and left borders to provide for efficient plant cell transformation, a selectable marker gene, unique multiple cloning sites in the T border regions, the colE1 replication of origin and a wide host range replicon. The binary Ti vectors carrying an expression cassette of the invention can be used to transform both prokaryotic and eukaryotic cells, but is preferably used to transform dicot plant cells.

In Vitro Screening of Expression Cassettes: Once the expression cassette is constructed and subcloned into a suitable plasmid, it can be screened for the ability to substantially inhibit the translation of an mRNA coding for a seed storage protein by standard methods such as hybrid arrested translation. For example, for hybrid selection or arrested translation, a preselected antisense DNA sequence is subcloned into an SP6/T7 containing plasmids (as supplied by ProMega Corp.). For transformation of plants cells, suitable vectors include plasmids such as described herein. Typically, hybrid arrest translation is an in vitro assay that measures the inhibition of translation of an mRNA encoding a particular seed storage protein. This screening method can also be used to select and identify preselected antisense DNA sequences that inhibit translation of a family or subfamily of zein protein genes. As a control, the corresponding sense expression cassette is introduced into plants and the phenotype assayed.

DNA Delivery of the DNA Molecules into Host Cells: The present invention generally includes steps directed to introducing a feruloyl-CoA:monolignol transferase nucleic acids, such as a preselected cDNA encoding the selected feruloyl-CoA:monolignol transferase enzyme, into a recipient cell to create a transformed cell. In some instances the frequency of occurrence of cells taking up exogenous (foreign) DNA may be low. Moreover, it is most likely that not all recipient cells receiving DNA segments or sequences will result in a transformed cell wherein the DNA is stably integrated into the plant genome and/or expressed. Some may show only initial and transient gene expression. However, certain cells from virtually any dicot or monocot species may be stably transformed, and these cells regenerated into transgenic plants, through the application of the techniques disclosed herein.

Another aspect of the invention is a plant with lignin containing monolignol ferulates (e.g., coniferyl ferulate), wherein the plant has an introduced feruloyl-CoA:monolignol transferase nucleic acid. The plant can be a monocotyledon or a dicotyledon. Another aspect of the invention includes plant cells (e.g., embryonic cells or other cell lines) that can regenerate fertile transgenic plants and/or seeds. The cells can be derived from either monocotyledons or dicotyledons. Suitable examples of plant species include grasses, softwoods, hardwoods, wheat, rice, *Arabidopsis*, tobacco, maize, soybean, and the like. In some embodiments, the plant or cell is a monocotyledon plant or cell. For example, the plant or cell can be a softwood plant or cell, or a maize plant or cell. In some embodiments, the plant or cell is a dicotyledon plant or cell. For example, the plant or cell can be a hardwood plant or cell. The cell(s) may be in a suspension cell culture or may be in an intact plant part, such as an immature embryo, or in a specialized plant tissue, such as callus, such as Type I or Type II callus.

Transformation of the plant cells can be conducted by any one of a number of methods known to those of skill in the art. Examples are: Transformation by direct DNA transfer into plant cells by electroporation (U.S. Pat. Nos. 5,384,253 and 5,472,869, Dekeyser et al., *The Plant Cell.* 2:591-602 (1990)); direct DNA transfer to plant cells by PEG precipitation (Hayashimoto et al., *Plant Physiol.* 93:857-863 (1990)); direct DNA transfer to plant cells by microprojectile bombardment (McCabe et al., *Bio/Technology.* 6:923-926 (1988); Gordon-Kamm et al., *The Plant Cell.* 2:603-618 (1990); U.S. Pat. Nos. 5,489,520; 5,538,877; and 5,538,880) and DNA transfer to plant cells via infection with *Agrobacterium*. Methods such as microprojectile bombardment or electroporation can be carried out with "naked" DNA where the expression cassette may be simply carried on any *E. coli*-derived plasmid cloning vector. In the case of viral vectors, it is desirable that the system retain replication functions, but lack functions for disease induction.

One method for dicot transformation, for example, involves infection of plant cells with *Agrobacterium tumefaciens* using the leaf-disk protocol (Horsch et al., *Science* 227:1229-1231 (1985). Monocots such as *Zea mays* can be transformed via microprojectile bombardment of embryogenic callus tissue or immature embryos, or by electroporation following partial enzymatic degradation of the cell wall with a pectinase-containing enzyme (U.S. Pat. Nos. 5,384,253; and 5,472,869). For example, embryogenic cell lines derived from immature *Zea mays* embryos can be transformed by accelerated particle treatment as described by Gordon-Kamm et al. (*The Plant Cell.* 2:603-618 (1990)) or U.S. Pat. Nos. 5,489,520; 5,538,877 and 5,538,880, cited above. Excised immature embryos can also be used as the target for transformation prior to tissue culture induction, selection and regeneration as described in U.S. application Ser. No. 08/112,245 and PCT publication WO 95/06128. Furthermore, methods for transformation of monocotyledonous plants utilizing *Agrobacterium tumefaciens* have been described by Hiei et al. (European Patent 0 604 662, 1994) and Saito et al. (European Patent 0 672 752, 1995).

Methods such as microprojectile bombardment or electroporation are carried out with "naked" DNA where the expression cassette may be simply carried on any *E. coli*-derived plasmid cloning vector. In the case of viral vectors, it is desirable that the system retain replication functions, but lack functions for disease induction.

The choice of plant tissue source for transformation will depend on the nature of the host plant and the transformation protocol. Useful tissue sources include callus, suspensions, culture cells, protoplasts, leaf segments, stem segments, tassels, pollen, embryos, hypocotyls, tuber segments, meristematic regions, and the like. The tissue source is selected and transformed so that it retains the ability to regenerate whole, fertile plants following transformation, i.e., contains totipotent cells. Type I or Type II embryonic maize callus and immature embryos are preferred *Zea mays* tissue sources. Similar tissues can be transformed for softwood or hardwood species. Selection of tissue sources for transformation of monocots is described in detail in U.S. application Ser. No. 08/112,245 and PCT publication WO 95/06128.

The transformation is carried out under conditions directed to the plant tissue of choice. The plant cells or tissue are exposed to the DNA or RNA carrying the feruloyl-CoA: monolignol transferase nucleic acids for an effective period of time. This may range from a less than one second pulse of electricity for electroporation to a 2-3 day co-cultivation in the presence of plasmid-bearing *Agrobacterium* cells. Buffers and media used will also vary with the plant tissue source and transformation protocol. Many transformation protocols employ a feeder layer of suspended culture cells (tobacco or Black Mexican Sweet corn, for example) on the surface of solid media plates, separated by a sterile filter paper disk from the plant cells or tissues being transformed.

Electroporation: Where one wishes to introduce DNA by means of electroporation, it is contemplated that the method of Krzyzek et al. (U.S. Pat. No. 5,384,253) may be advantageous. In this method, certain cell wall-degrading enzymes, such as pectin-degrading enzymes, are employed to render the target recipient cells more susceptible to transformation by electroporation than untreated cells. Alternatively, recipient cells can be made more susceptible to transformation, by mechanical wounding.

To effect transformation by electroporation, one may employ either friable tissues such as a suspension cell cultures, or embryogenic callus, or alternatively, one may transform immature embryos or other organized tissues directly. The cell walls of the preselected cells or organs can be partially degraded by exposing them to pectin-degrading enzymes (pectinases or pectolyases) or mechanically wounding them in a controlled manner Such cells would then be receptive to DNA uptake by electroporation, which may be carried out at this stage, and transformed cells then identified by a suitable selection or screening protocol dependent on the nature of the newly incorporated DNA.

Microprojectile Bombardment: A further advantageous method for delivering transforming DNA segments to plant cells is microprojectile bombardment. In this method, microparticles may be coated with DNA and delivered into cells by a propelling force. Exemplary particles include those comprised of tungsten, gold, platinum, and the like.

It is contemplated that in some instances DNA precipitation onto metal particles would not be necessary for DNA delivery to a recipient cell using microprojectile bombardment. In an illustrative embodiment, non-embryogenic BMS cells were bombarded with intact cells of the bacteria *E. coli* or *Agrobacterium tumefaciens* containing plasmids with either the β-glucuronidase or bar gene engineered for expression in maize. Bacteria were inactivated by ethanol dehydration prior to bombardment. A low level of transient expression of the β-glucuronidase gene was observed 24-48 hours following DNA delivery. In addition, stable transformants containing the bar gene were recovered following bombardment with either *E. coli* or *Agrobacterium tumefaciens* cells. It is contemplated that particles may contain DNA rather than be coated with DNA. Hence it is proposed that particles may increase the level of DNA delivery but are not, in and of themselves, necessary to introduce DNA into plant cells.

An advantage of microprojectile bombardment, in addition to it being an effective means of reproducibly stably transforming monocots, is that the isolation of protoplasts (Christou et al., *PNAS.* 84:3962-3966 (1987)), the formation of partially degraded cells, or the susceptibility to *Agrobacterium* infection is not required. An illustrative embodiment of a method for delivering DNA into maize cells by acceleration is a Biolistics Particle Delivery System, which can be used to propel particles coated with DNA or cells through a screen, such as a stainless steel or Nytex screen, onto a filter surface covered with maize cells cultured in suspension (Gordon-Kamm et al., *The Plant Cell.* 2:603-618 (1990)). The screen disperses the particles so that they are not delivered to the recipient cells in large aggregates. It is believed that a screen intervening between the projectile apparatus and the cells to be bombarded reduces the size of projectile aggregate and may contribute to a higher frequency of transformation, by reducing damage inflicted on the recipient cells by an aggregated projectile.

For bombardment, cells in suspension are preferably concentrated on filters or solid culture medium. Alternatively, immature embryos or other target cells may be arranged on solid culture medium. The cells to be bombarded are positioned at an appropriate distance below the macroprojectile stopping plate. If desired, one or more screens are also positioned between the acceleration device and the cells to be bombarded. Through the use of techniques set forth here-in one may obtain up to 1000 or more foci of cells transiently expressing a marker gene. The number of cells in a focus which express the exogenous gene product 48 hours post-bombardment often range from about 1 to 10 and average about 1 to 3.

In bombardment transformation, one may optimize the prebombardment culturing conditions and the bombardment parameters to yield the maximum numbers of stable transformants. Both the physical and biological parameters for bombardment can influence transformation frequency. Physical factors are those that involve manipulating the DNA/microprojectile precipitate or those that affect the path and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmid DNA.

One may wish to adjust various bombardment parameters in small scale studies to fully optimize the conditions and/or to adjust physical parameters such as gap distance, flight distance, tissue distance, and helium pressure. One may also minimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. Execution of such routine adjustments will be known to those of skill in the art.

An Example of Production and Characterization of Stable Transgenic Maize: After effecting delivery of a feruloyl-CoA:monolignol transferase nucleic acid to recipient cells by any of the methods discussed above, the transformed cells can be identified for further culturing and plant regeneration. As mentioned above, in order to improve the ability to identify transformants, one may desire to employ a selectable or screenable marker gene as, or in addition to, the expressible feruloyl-CoA:monolignol transferase nucleic acids. In this case, one would then generally assay the potentially transformed cell population by exposing the cells to a selective agent or agents, or one would screen the cells for the desired marker gene trait.

Selection: An exemplary embodiment of methods for identifying transformed cells involves exposing the bombarded cultures to a selective agent, such as a metabolic inhibitor, an antibiotic, herbicide or the like. Cells which have been transformed and have stably integrated a marker gene conferring resistance to the selective agent used, will grow and divide in culture. Sensitive cells will not be amenable to further culturing.

To use the bar-bialaphos or the EPSPS-glyphosate selective system, bombarded tissue is cultured for about 0-28 days on nonselective medium and subsequently transferred to medium containing from about 1-3 mg/l bialaphos or about 1-3 mM glyphosate, as appropriate. While ranges of about 1-3 mg/l bialaphos or about 1-3 mM glyphosate can be employed, it is proposed that ranges of at least about 0.1-50 mg/l bialaphos or at least about 0.1-50 mM glyphosate will find utility in the practice of the invention. Tissue can be placed on any porous, inert, solid or semi-solid support for bombardment, including but not limited to filters and solid culture medium. Bialaphos and glyphosate are provided as examples of agents suitable for selection of transformants, but the technique of this invention is not limited to them.

An example of a screenable marker trait is the red pigment produced under the control of the R-locus in maize. This pigment may be detected by culturing cells on a solid support containing nutrient media capable of supporting growth at this stage and selecting cells from colonies (visible aggregates of cells) that are pigmented. These cells may be cultured further, either in suspension or on solid media. The R-locus is useful for selection of transformants from bombarded immature embryos. In a similar fashion, the introduction of the C1 and B genes will result in pigmented cells and/or tissues.

The enzyme luciferase is also useful as a screenable marker in the context of the present invention. In the presence of the substrate luciferin, cells expressing luciferase emit light which can be detected on photographic or X-ray film, in a luminometer (or liquid scintillation counter), by devices that enhance night vision, or by a highly light sensitive video camera, such as a photon counting camera. All of these assays are nondestructive and transformed cells may be cultured further following identification. The photon counting camera is especially valuable as it allows one to identify specific cells or groups of cells which are expressing luciferase and manipulate those in real time.

It is further contemplated that combinations of screenable and selectable markers may be useful for identification of transformed cells. For example, selection with a growth inhibiting compound, such as bialaphos or glyphosate at concentrations below those that cause 100% inhibition followed by screening of growing tissue for expression of a screenable marker gene such as luciferase would allow one to recover transformants from cell or tissue types that are not amenable to selection alone. In an illustrative embodiment embryogenic Type II callus of Zea mays L. can be selected with sub-lethal levels of bialaphos. Slowly growing tissue was subsequently screened for expression of the luciferase gene and transformants can be identified.

Regeneration and Seed Production: Cells that survive the exposure to the selective agent, or cells that have been scored positive in a screening assay, are cultured in media that supports regeneration of plants. One example of a growth regulator that can be used for such purposes is dicamba or 2,4-D. However, other growth regulators may be employed, including NAA, NAA+2,4-D or perhaps even picloram. Media improvement in these and like ways can facilitate the growth of cells at specific developmental stages. Tissue can be maintained on a basic media with growth regulators until sufficient tissue is available to begin plant regeneration efforts, or following repeated rounds of manual selection, until the morphology of the tissue is suitable for regeneration, at least two weeks, then transferred to media conducive to maturation of embryoids. Cultures are typically transferred every two weeks on this medium. Shoot development signals the time to transfer to medium lacking growth regulators.

The transformed cells, identified by selection or screening and cultured in an appropriate medium that supports regeneration, can then be allowed to mature into plants. Developing plantlets are transferred to soilless plant growth mix, and hardened, e.g., in an environmentally controlled chamber at about 85% relative humidity, about 600 ppm $CO_2$, and at about 25-250 microeinsteins/sec·$m^2$ of light. Plants can be matured either in a growth chamber or greenhouse. Plants are regenerated from about 6 weeks to 10 months after a transformant is identified, depending on the initial tissue. During regeneration, cells are grown on solid media in tissue culture vessels. Illustrative embodiments of such vessels are petri dishes and Plant Con™. Regenerating plants can be grown at about 19° C. to 28° C. After the regenerating plants have reached the stage of shoot and root development, they may be transferred to a greenhouse for further growth and testing.

Mature plants are then obtained from cell lines that are known to express the trait. In some embodiments, the regenerated plants are self pollinated. In addition, pollen obtained from the regenerated plants can be crossed to seed grown plants of agronomically important inbred lines. In some cases, pollen from plants of these inbred lines is used to pollinate regenerated plants. The trait is genetically characterized by evaluating the segregation of the trait in first and later generation progeny. The heritability and expression in plants of traits selected in tissue culture are of particular importance if the traits are to be commercially useful.

Regenerated plants can be repeatedly crossed to inbred plants in order to introgress the feruloyl-CoA:monolignol transferase nucleic acids into the genome of the inbred plants. This process is referred to as backcross conversion. When a sufficient number of crosses to the recurrent inbred parent have been completed in order to produce a product of the backcross conversion process that is substantially isogenic with the recurrent inbred parent except for the presence of the introduced feruloyl-CoA:monolignol transferase nucleic acids, the plant is self-pollinated at least once in order to produce a homozygous backcross converted inbred containing the feruloyl-CoA:monolignol transferase nucleic acids. Progeny of these plants are true breeding.

Alternatively, seed from transformed monocot plants regenerated from transformed tissue cultures is grown in the field and self-pollinated to generate true breeding plants.

Seed from the fertile transgenic plants can then be evaluated for the presence and/or expression of the feruloyl-CoA: monolignol transferase nucleic acids (or the feruloyl-CoA: monolignol transferase enzyme). Transgenic plant and/or seed tissue can be analyzed for feruloyl-CoA:monolignol transferase expression using standard methods such as SDS polyacrylamide gel electrophoresis, liquid chromatography (e.g., HPLC) or other means of detecting a product of feruloyl-CoA:monolignol transferase activity (e.g., coniferyl ferulate).

Once a transgenic seed expressing the feruloyl-CoA: monolignol transferase sequence and having an increase in monolignol ferulates in the lignin of the plant is identified, the seed can be used to develop true breeding plants. The true breeding plants are used to develop a line of plants with an increase in the percent of monolignol ferulates in the lignin of the plant while still maintaining other desirable functional agronomic traits. Adding the trait of increased monolignol ferulate production in the lignin of the plant can be accomplished by back-crossing with this trait and with plants that do not exhibit this trait and studying the pattern of inheritance in segregating generations. Those plants expressing the target trait in a dominant fashion are preferably selected. Back-crossing is carried out by crossing the original fertile transgenic plants with a plant from an inbred line exhibiting desirable functional agronomic characteristics while not necessarily expressing the trait of an increased percent of monolignol ferulates in the lignin of the plant. The resulting progeny are then crossed back to the parent that expresses the increased monolignol ferulate trait. The progeny from this cross will also segregate so that some of the progeny carry the trait and some do not. This back-crossing is repeated until an inbred line with the desirable functional agronomic traits, and with expression of the trait involving an increase in monolignol ferulates (e.g., coniferyl ferulate) within the lignin of the plant. Such expression of the increased percentage of monolignol ferulates in plant lignin can be expressed in a dominant fashion.

Subsequent to back-crossing, the new transgenic plants can be evaluated for an increase in the weight percent of monolignol ferulates incorporated into the lignin of the plant. This can be done, for example, by NMR analysis of whole plant cell walls (Kim, H., and Ralph, J. Solution-state 2D NMR of ball-milled plant cell wall gels in DMSO-$d_6$/pyridine-$d_5$. (2010) *Org. Biomol. Chem.* 8(3), 576-591; Yelle, D. J., Ralph, J., and Frihart, C. R. Characterization of non-derivatized plant cell walls using high-resolution solution-state NMR spectroscopy. (2008) *Magn. Reson. Chem.* 46(6), 508-517; Kim, H., Ralph, J., and Akiyama, T. Solution-state 2D NMR of Ball-milled Plant Cell Wall Gels in DMSO-$d_6$. (2008) *BioEnergy Research* 1(1), 56-66; Lu, F., and Ralph, J. Non-degradative dissolution and acetylation of ball-milled plant cell walls; high-resolution solution-state NMR. (2003) *Plant J.* 35(4), 535-544). The new transgenic plants can also be evaluated for a battery of functional agronomic characteristics such as lodging, kernel hardness, yield, resistance to disease, resistance to insect pests, drought resistance, and/or herbicide resistance.

Plants that may be improved by these methods include but are not limited to oil and/or starch plants (canola, potatoes, lupins, sunflower and cottonseed), forage plants (alfalfa, clover and fescue), grains (maize, wheat, barley, oats, rice, sorghum, millet and rye), grasses (switchgrass, prairie grass, wheat grass, sudangrass, sorghum, straw-producing plants), softwood, hardwood and other woody plants (e.g., those used for paper production such as poplar species, pine species, and *eucalyptus*). In some embodiments the plant is a gymnosperm. Examples of plants useful for pulp and paper production include most pine species such as loblolly pine, Jack pine, Southern pine, *Radiata* pine, spruce, Douglas fir and others. Hardwoods that can be modified as described herein include aspen, poplar, *eucalyptus*, and others. Plants useful for making biofuels and ethanol include corn, grasses (e.g., *miscanthus*, switchgrass, and the like), as well as trees such as poplar, aspen, willow, and the like. Plants useful for generating dairy forage include legumes such as alfalfa, as well as forage grasses such as bromegrass, and bluestem.

Determination of Stably Transformed Plant Tissues: To confirm the presence of the feruloyl-CoA:monolignol transferase nucleic acids in the regenerating plants, or seeds or progeny derived from the regenerated plant, a variety of assays may be performed. Such assays include, for example, molecular biological assays available to those of skill in the art, such as Southern and Northern blotting and PCR; biochemical assays, such as detecting the presence of a protein product, e.g., by immunological means (ELISAs and Western blots) or by enzymatic function; plant part assays, such as leaf, seed or root assays; and also, by analyzing the phenotype of the whole regenerated plant.

Whereas DNA analysis techniques may be conducted using DNA isolated from any part of a plant, RNA may only be expressed in particular cells or tissue types and so RNA for analysis can be obtained from those tissues. PCR techniques may also be used for detection and quantification of RNA produced from introduced feruloyl-CoA:monolignol transferase nucleic acids. PCR also be used to reverse transcribe RNA into DNA, using enzymes such as reverse transcriptase, and then this DNA can be amplified through the use of conventional PCR techniques. Further information about the nature of the RNA product may be obtained by Northern blotting. This technique will demonstrate the presence of an RNA species and give information about the integrity of that RNA. The presence or absence of an RNA species can also be determined using dot or slot blot Northern hybridizations. These techniques are modifications of Northern blotting and also demonstrate the presence or absence of an RNA species.

While Southern blotting and PCR may be used to detect the feruloyl-CoA:monolignol transferase nucleic acid in question, they do not provide information as to whether the preselected DNA segment is being expressed. Expression may be evaluated by specifically identifying the protein products of the introduced feruloyl-CoA:monolignol transferase nucleic acids or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange, liquid chromatography or gel exclusion chromatography. The unique structures of individual proteins offer opportunities for use of specific antibodies to detect their presence in formats such as an ELISA assay. Combinations of approaches may be employed with even greater specificity such as Western blotting in which antibodies are used to locate individual gene products that have been separated by electrophoretic techniques. Additional techniques may be employed to absolutely confirm the identity of the feruloyl-CoA:monolignol transferase such as evaluation by amino acid sequencing following purification. The Examples of this application also provide assay procedures for detecting and quantifying feruloyl-CoA:monolignol transferase activity. Other procedures may be additionally used.

The expression of a gene product can also be determined by evaluating the phenotypic results of its expression. These assays also may take many forms including but not limited to analyzing changes in the chemical composition, morphology, or physiological properties of the plant. Chemical composition may be altered by expression of preselected DNA segments encoding storage proteins which change amino acid composition and may be detected by amino acid analysis.

Methods pertaining to feruloyl-CoA:monolignol transferase (FMT) enzymatic assays, size exclusion chromatography of FMT, NMR, synthesis of authentic coniferyl ferulate, genetically modifying poplar trees to express FMT, testing for expression and enzymatic activity in poplar trees modified to express FMT, and other methods are in U.S. Pat. Nos. 9,441,235, 9,487,794, and 9,493,783 for an *Angelica sinesis* FMT. These references are specifically incorporated herein by reference in their entireties. The methods described in these references can be adapted for use with the FMT enzymes provided herein.

Definitions

As used herein, "isolated" means a nucleic acid or polypeptide has been removed from its natural or native cell. Thus, the nucleic acid or polypeptide can be physically isolated from the cell or the nucleic acid or polypeptide can be present or maintained in another cell where it is not naturally present or synthesized.

As used herein, a "native" nucleic acid or polypeptide means a DNA, RNA or amino acid sequence or segment that has not been manipulated in vitro, i.e., has not been isolated, purified, and/or amplified.

The following non-limiting Examples illustrate how aspects of the invention have been developed and can be made and used.

Examples

Example 1: Identification and Testing of *Zea Mays*, *Panicum virgatum*, and *Sorghum bicolor* FMTs This Example illustrates isolation and expression of enzymatically active FMTs from *Zea mays, Panicum virgatum*, and *Sorghum bicolor* having unique selectivity for coupling monolignols to feruloyl-CoA.

Methods

Selection of genes. Gene sequences were obtained from NCBI GenBank and were selected by their close homology to monolignol acyl transferases, especially from rice (*Oryza sativa*, OsAT5/OsFMT) (Karlen, S. D., Zhang, C., Peck, M. L., Smith, R. A., Padmakshan, D., Helmich, K. E., Free, H. C. A., Lee, S., Smith, B. G., Lu, F., Sedbrook, J. C., Sibout, R., Grabber, J. H., Runge, T. M., Mysore, K. S., Harris, P. J., Bartley, L. E. and Ralph, J. (2016) Monolignol ferulate conjugates are naturally incorporated into plant lignins. *Science Advances*, 2, e1600393). Grass genes from sorghum, switchgrass, *Brachypodium*, maize, and rice (Karlen S D, et al. (2016) Monolignol ferulate conjugates are naturally incorporated into plant lignins. *Science Advances* 2(10):e1600393: 1600391-1600399) were prepared alongside *Angelica sinensis* FMT (AsFMT) (Wilkerson C G, et al. (2014) Monolignol ferulate transferase introduces chemically labile linkages into the lignin backbone. *Science* 344 (6179):90-93) (Table 1). Protein sequence comparisons were made with NCBI BLAST+2.5.0 using default settings (Camacho, C., Coulouris, G., Avagyan, V., Ma, N, Papadopoulos J, Bealer K, Madden T L. BLAST+: architecture and applications. *BMC Bioinformatics*. 2009 Dec. 15; 10:421). The sequence identity is reported both as a percentage, as well as a fraction, where the numerator is the number of identical residues, and the denominator is the length of the matched region.

Cloning vector. Coding sequences were synthesized by GenScript Corporation (Piscataway, N.J.) and cloned into the wheat germ cell-free expression vector, pEU (Sawasaki, T., Hasegawa, Y., Tsuchimochi, M., Kasahara, Y. and Endo, Y. (2000) Construction of an efficient expression vector for coupled transcription/translation in a wheat germ cell-free system. *Nucleic Acids Symp Ser*, 9-10), which contains an SP6 promoter and omega enhancer sequence from tobacco mosaic virus. Plasmid DNA was purified from *E. coli* using a commercial purification kit, then treated with proteinase K and re-purified to remove residual RNAse activity and to determine concentration of the DNA. The nucleic acid coding sequences and amino acid sequences encoded thereby for each of ZmFMT, SbFMT, and PvFMT are provided elsewhere herein. The nucleic acid coding sequence for the putative FMT from *Brachypodium distachyon* (BdFMT) is as follows (SEQ ID NO:9)

```
ATGGCAGAAATCTGCACCGTGAACAGGAAGTCCCAGTCCTTCGTCAAGC

CGGCCGCGCCAACGCCAACGCCTCAGACGCCGCCGCCGCTGCTGGAGCT

GTCGGCCATCGACCGCGTGCCCGGGCTGCGCCACACCGTGCGCTCTCTC

CACGTCTTCCGCCCGCCGCCGCACGGCGACGGCGCCGCCTGCAGCAGGC

CGGCCGAGGTGATCCGCGCCGCGCTGGCCCGCGCGCTCGTGGAGTACCC

CGCGTTCGCCGGGCGGCTCGTCGTCGGCGGCTCCGGCTCGGACTGCGGC

GTGGCGTGCACCGGCGACGGAGCGTGGTTCGTTGAAGCGGCCGCCGGCT

GTAACCTGGAGGACGTGAACGAGCGGACTACCCTCTCGTGGTCTGCGA

GGAGGAGCTGCTCCCCACCGCCCCTGAGGGAGAGCTGGATCCTACAAGC

ATTCCGGTCATGATGCAGGTGACCGAATTCAGCTGCGGAGGATTTGTGG

TGGGCCTGGTAGCAGTCCACACCTTCGCAGACGGGCTCGGCGCGGCCCA

ATTCATCAACGCCATCGCCGAATTCGCCCGTGGCCTAAACAGGCCCACA

GTGAATCCCATATGGGCCCGAGCCACAATCCCCAACCCGCCCAAATTCC

CTCCCGGCCCACCACCATCCTTCCAATCCTTCGGCTTCCAGCATTTCGC

CACGGACATCCGTCCAGACCGCATCGCCCACGCCAAAGCCGAGTACCTC

AAGGCCACGGGCACCCACTGCTCGGCCTTCGACGTCGCCGTGGCCAAGG

TCTGGCAGGCCCGAACCCGGGCCGTAAGGTACGGCCCAGAGGCCCAGGT

GCAGGTCTGCTTCTTCGCCAACACGAGGCACCTTCTCGGAGAGCTTCTC

CCCGAAGGTTTCTACGGCAACTGCTTCTTCCCGGTCACCGTGAAGGCCA
```

-continued

```
GAGCTGGGGATGTTGCCGGCAGCAAGGATTTACTTGGTATTATCCGGAT
GATCAGGGACGGGAAGGCCAGGCTGCCTTTGGAGTTCGCCGATTGGGCG
TCAGGTTTAGGAGGAGGAGGGGCTGGGGATAAGATGAAGTTTGTGCAGG
ATGATCCTTATGAGCTGAGGTTTGAGCATAATGTGTTGTTTGTGTCGGA
TTGGACGAGGCTTGGGTTCTTGGAGGTGGACTATGGCTGGGGCGTGCCT
AGCCATGTTATACCTTTCAATTATGCGGACTACATGGCGGTCGCGGTGC
TCGGTGCTCCGCCGGCGCCGGTGAAGGGGACTCGGGTCATGACGCAGTG
CGTGGAGGAGAAGCATCTTAAGGAGTTCAGGGATGAGATGGAAGGCTCC
TTTTAG
```

SEQ ID NO:9 encodes the putative BdFMT enzyme with the following amino acid sequence (SEQ ID NO:10).

```
MAEICTVNRKSQSFVKPAAPTPTPQTPPPLLELSAIDRVPGLRHTVRSLH
VFRPPPHGDGAACSRPAEVIRAALARALVEYPAFAGRLVVGGSGSDCGVA
CTGDGAWFVEAAAGCNLEDVNELDYPLVVCEEELLPTAPEGELDPTSIPV
MMQVTEFSCGGFVVGLVAVHTFADGLGAAQFINAIAEFARGLNRPTVNPI
WARATIPNPPKFPPGPPPSFQSFGFQHFATDIRPDRIAHAKAEYLKATGT
HCSAFDVAVAKVWQARTRAVRYGPEAQVQVCFFANTRHLLGELLPEGFYG
NCFFPVTVKARAGDVAGSKDLLGIIRMIRDGKARLPLEFADWASGLGGGG
AGDKMKFVQDDPYELRFEHNVLFVSDWTRLGFLEVDYGWGVPSHVIPFNY
ADYMAVAVLGAPPAPVKGTRVMTQCVEEKHLKEFRDEMEGSF
```

Each of the native genes for the ZmFMT, SbFMT, PvFMT, and BdFMT proteins include introns, which are excluded from the sequences provided above.

Transcription. Messenger RNA was prepared by adding 1.6 U of SP6 RNA polymerase and 1 U of RNasin RNase inhibitor (Promega Corporation, Madison, Wis.) to plasmid DNA (0.2 mg/mL or higher) in the presence of 2.5 mM each of UTP, CTP, ATP, and GTP and 20 mM magnesium acetate, 2 mM spermidine HCl, 10 mM DTT, and 80 mM HEPES-KOH, pH 7.8. Transcription reactions were incubated at 37° C. for 4 h and visually monitored for the appearance of insoluble pyrophosphate byproducts, which are indicative of successful transcription.

Cell free translation. The active enzymes were produced using a wheat germ cell-free translation bilayer method previously reported (Makino, S., Beebe, E. T., Markley, J. L. and Fox, B. G. (2014) Cell-free protein synthesis for functional and structural studies. *Methods in Molecular Biology*, 1091, 161-178). Briefly, a translation reaction mixture consisting of 60 OD wheat germ extract (CellFree Sciences, Matsuyama, Japan), 0.04 mg/mL creatine kinase, 0.3 mM each amino acid, 12.6 mM HEPES-KOH, pH 7.8, 52.6 mM potassium acetate, 1.3 mM magnesium acetate, 0.2 mM spermidine HCl, 2.1 mM DTT, 0.6 mM ATP, 0.13 mM GTP, 8.4 mM creatine phosphate, and 0.003% sodium azide was prepared and combined with non-purified, fresh transcription at a ratio of 4 parts reaction mix to 1 part transcription. A feeding layer was prepared consisting of 0.3 mM each amino acid, 24 mM HEPES-KOH, pH 7.8, 100 mM potassium acetate, 2.5 mM magnesium acetate, 0.4 mM spermidine HCl, 4 mM DTT, 1.2 mM ATP, 0.25 mM GTP, 16 mM creatine phosphate, and 0.005% sodium azide, of which 125 µL was added to wells of a U-bottom 96-well plate. 25 µL of the denser translation reaction mixture was carefully underlayed below the feeding layer, forming a bilayer. The plate was sealed and incubated at 22° C. for 18 h. The fully-diffused 150-µL bilayer reaction was then harvested and used for expression analysis by SDS-PAGE, and activity screening.

Figure 2A:
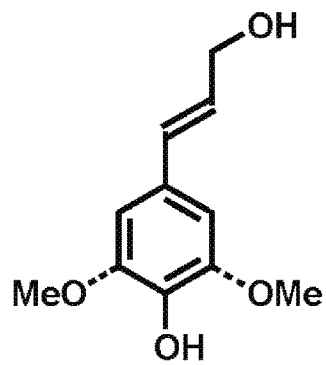
FIGS. 2A-2E show the structures of possible reactants and products of the activity of certain FMT enzymes.
Figure 2B:
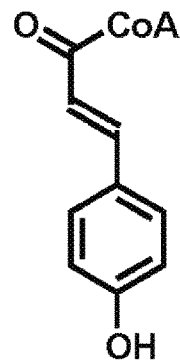
Figure 2C:
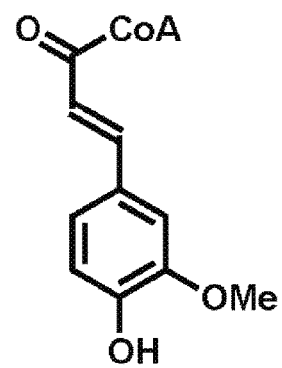
Figure 2D:
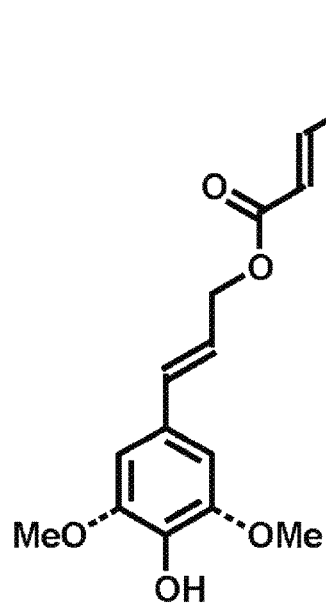
Figure 2E:
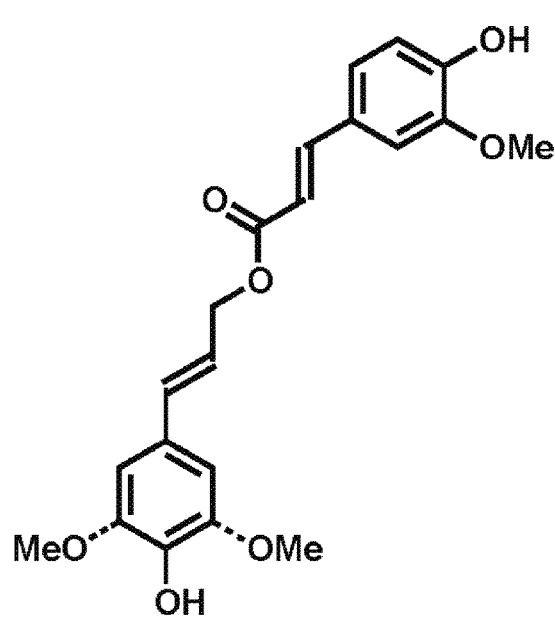
Figure 3:
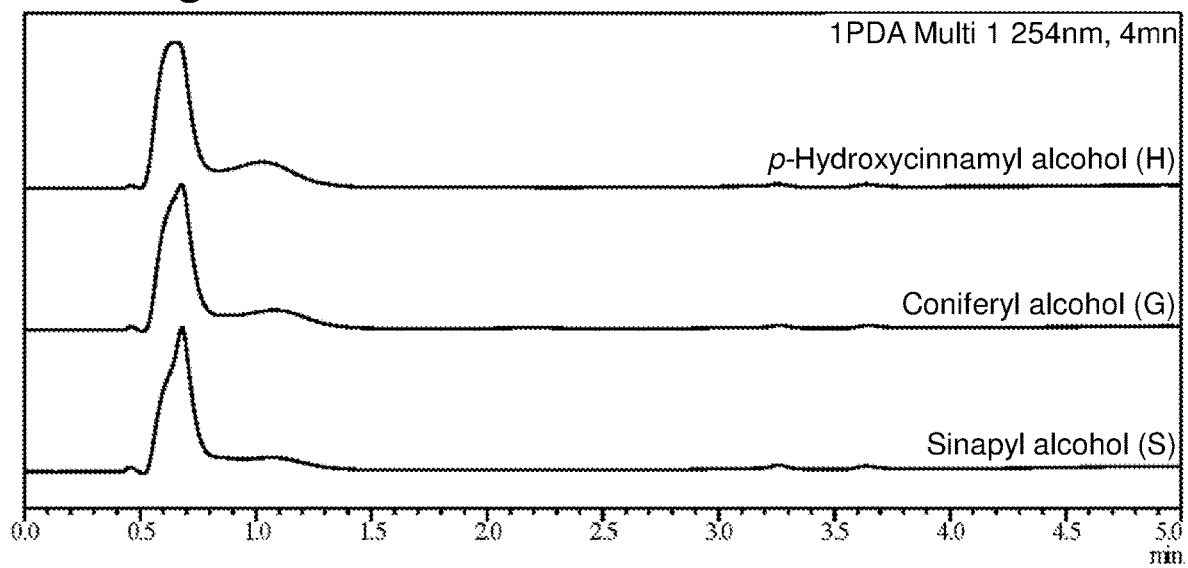
FIG. 3 shows liquid chromatography-mass spectrometry (LC-MS) traces of p-hydroxycinnamyl alcohol (H), coniferyl alcohol (G), and sinapyl alcohol (S).

Activity screening. The enzyme mixture was screened for activity with feruloyl-CoA (FIG. 2C) and p-coumaroyl-CoA (FIG. 2B) and all three monolignols (FIG. 2A) (p-coumaryl, coniferyl, and sinapyl alcohol). Each enzyme was tested individually alongside positive and negative controls following the procedure previously reported (Withers, S., Lu, F., Kim, H., Zhu, Y., Ralph, J. and Wilkerson, C. G. (2012) Identification of a grass-specific enzyme that acylates monolignols with p-coumarate. *Journal of Biological Chemistry*, 287, 8347-8355). Briefly, the assay was initiated by adding 10 µL of wheat germ cell-free translation containing one of the FMT enzymes at a concentration of 1.5-2 µM to a reaction containing 50 mM sodium phosphate buffer, pH 6, 1 mM dithiothreitol (DTT), 1 mM CoA thioester, 1 mM monolignol mixture (each monolignol at 1 mM concentration), and deionized water in a final volume of 50 pt. After a 30-min incubation, the reaction was stopped by the addition of an equal volume 100 mM hydrochloric acid. Reaction products were solubilized by adjusting the solution to 50% methanol. An identical assay with no enzyme added was performed for every reaction. Samples were filtered through 0.2 µm filters prior to analysis by liquid chromatography-mass spectrometry (LC-MS).

Sequence comparison. Alignments and an identity matrix of select sequences were generated with Clustal Omega (Sievers F, Wilm A, Dineen D, Gibson T J, Karplus K, Li W, Lopez R, McWilliam H, Remmert M, Soding J, Thompson J D, Higgins D G. Fast, scalable generation of high-quality protein multiple sequence alignments using Clustal Omega. *Mol Syst Biol*. 2011 Oct. 11; 7:539).

Results

Figure 4A:
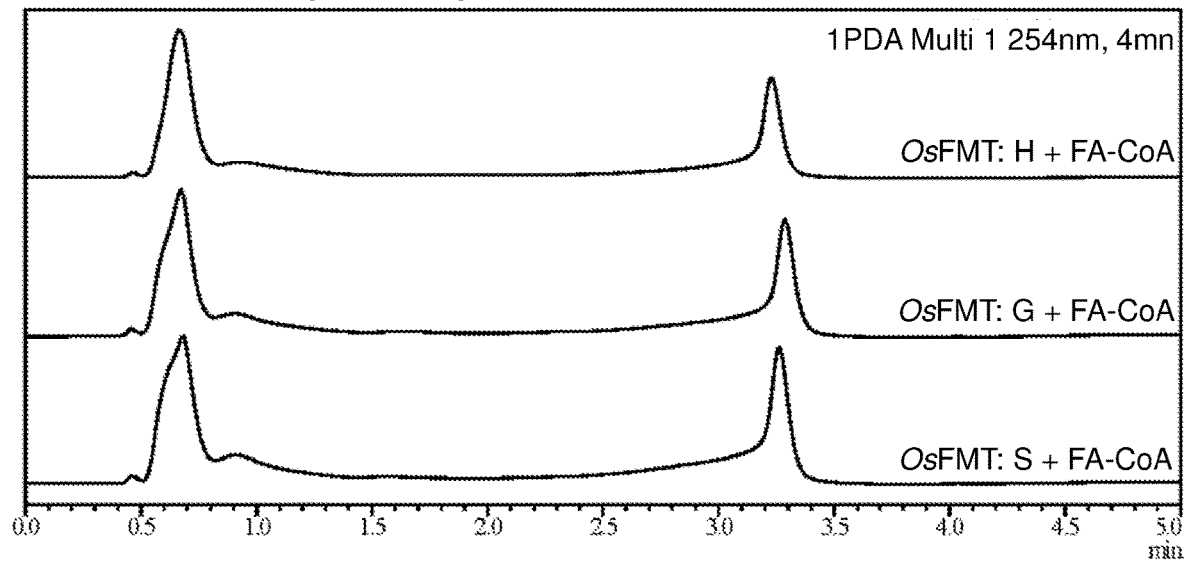
FIGS. 4A and 4B show LC-MS traces of chemical species present after incubating an Oryza sativa FMT (OsFMT) with each of p-hydroxycinnamyl alcohol (H), coniferyl alcohol (G), and sinapyl alcohol (S) and either feruloyl-CoA (FA-CoA) (FIG. 4A) or p-coumaroyl-CoA (pCA-CoA) (FIG. 4B).
Figure 4B:
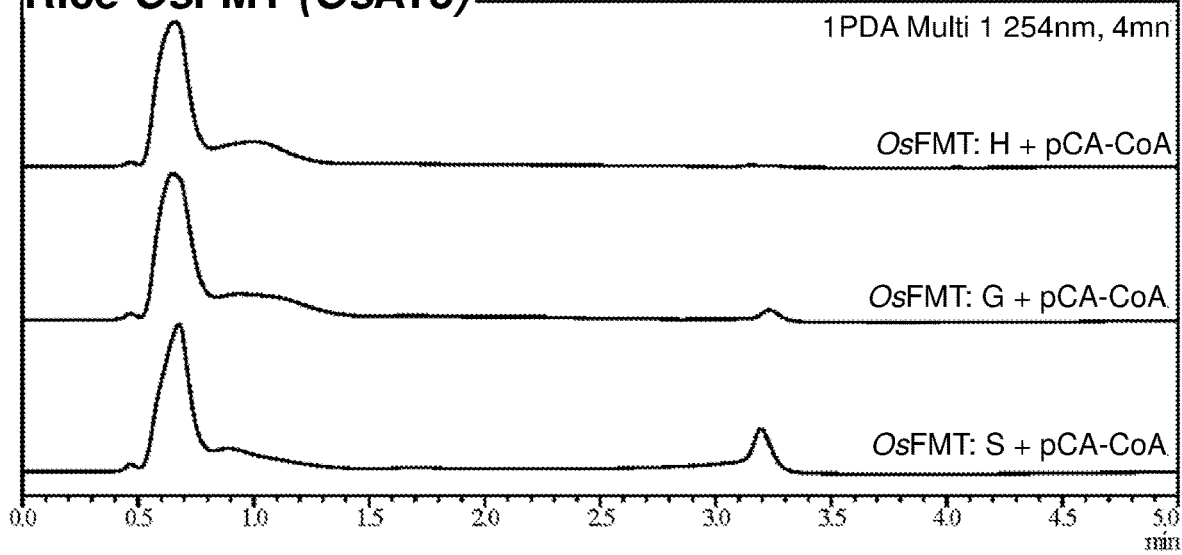
Figure 5A:
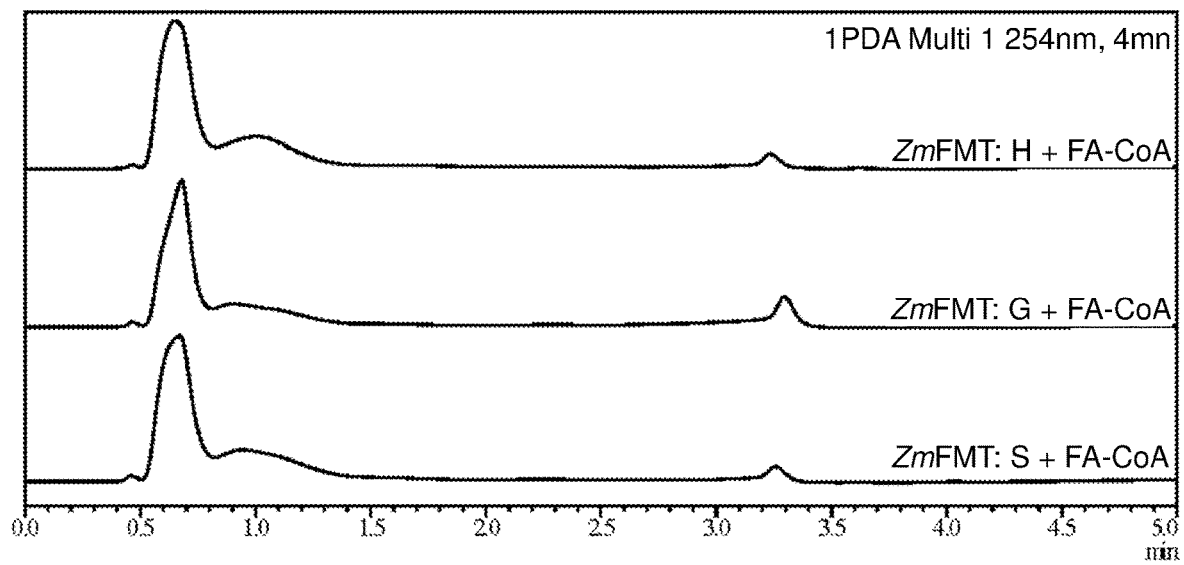
FIGS. 5A and 5B show LC-MS traces of chemical species present after incubating a Zea mays FMT (ZmFMT) with each of p-hydroxycinnamyl alcohol (H), coniferyl alcohol (G), and sinapyl alcohol (S) and either feruloyl-CoA (FA-CoA) (FIG. 5A) or p-coumaroyl-CoA (pCA-CoA) (FIG. 5B).
Figure 5B:
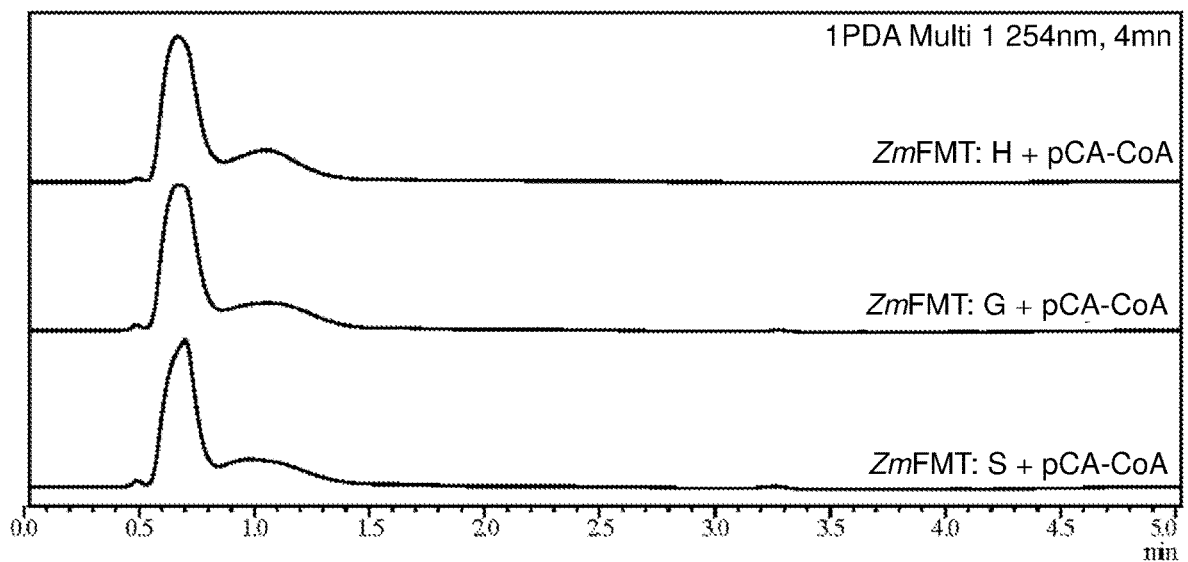
Figure 6A:
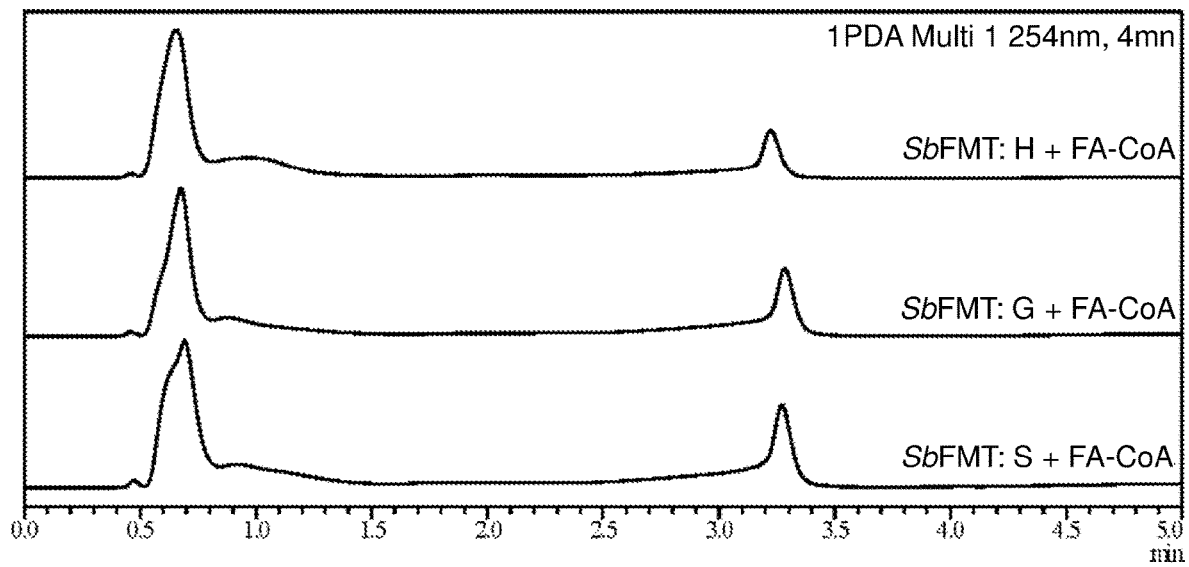
FIGS. 6A and 6B show LC-MS traces of chemical species present after incubating a Sorghum bicolor FMT (SbFMT) with each of p-hydroxycinnamyl alcohol (H), coniferyl alcohol (G), and sinapyl alcohol (S) and either feruloyl-CoA (FA-CoA) (FIG. 6A) or p-coumaroyl-CoA (pCA-CoA) (FIG. 6B).
Figure 6B:
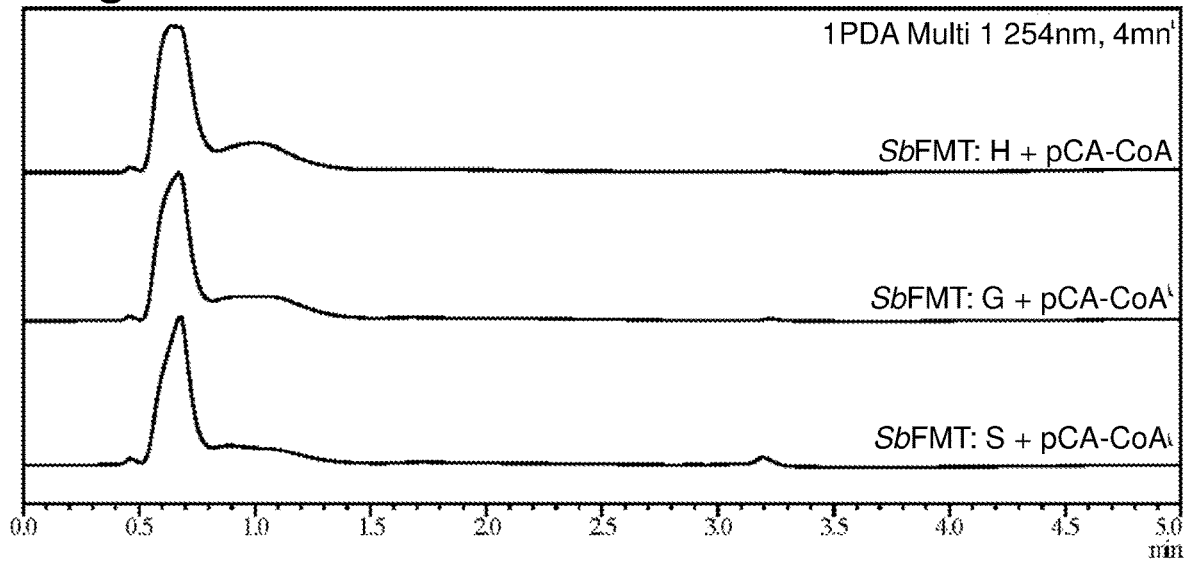
Figure 7A:
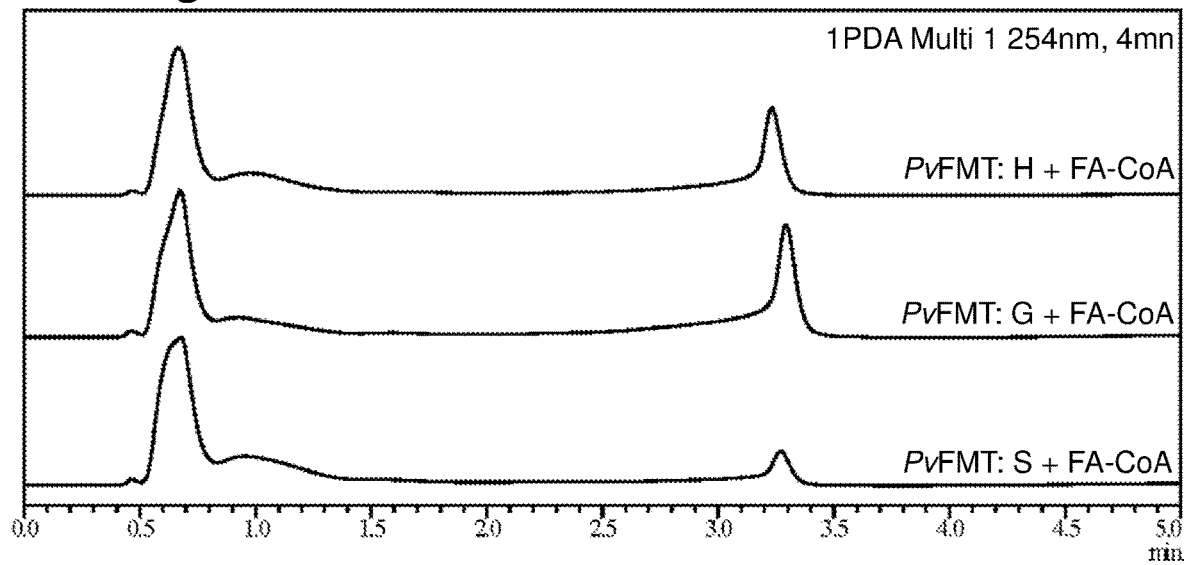
FIGS. 7A and 7B show LC-MS traces of chemical species present after incubating a Panicum virgatum FMT (PvFMT) with each of p-hydroxycinnamyl alcohol (H), coniferyl alcohol (G), and sinapyl alcohol (S) and either feruloyl-CoA (FA-CoA) (FIG. 7A) or p-coumaroyl-CoA (pCA-CoA) (FIG. 7B).
Figure 7B:
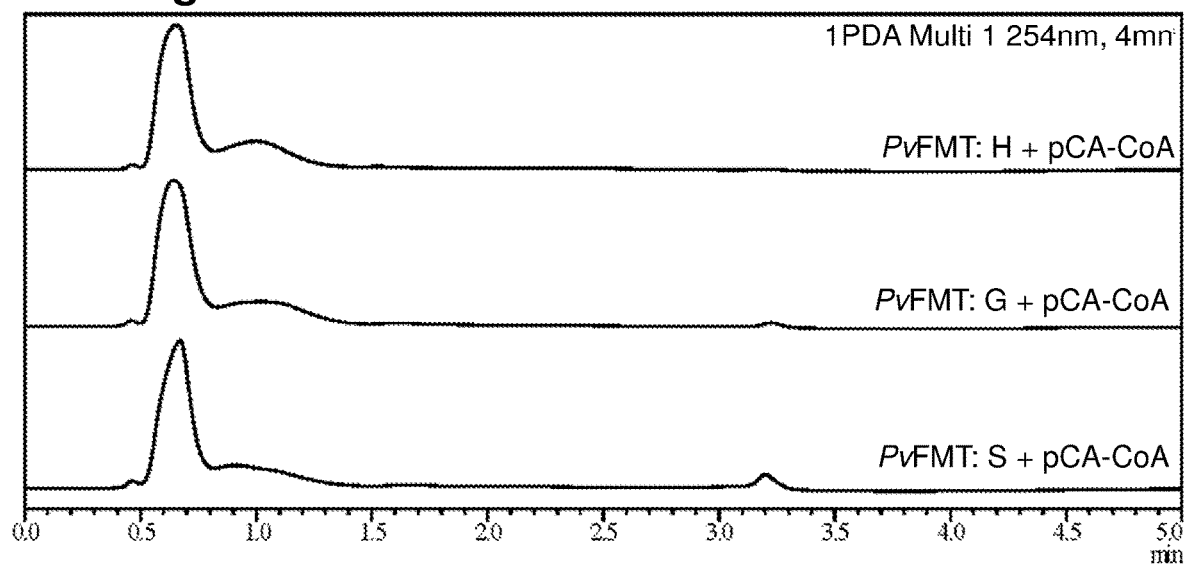
Figure 8A:
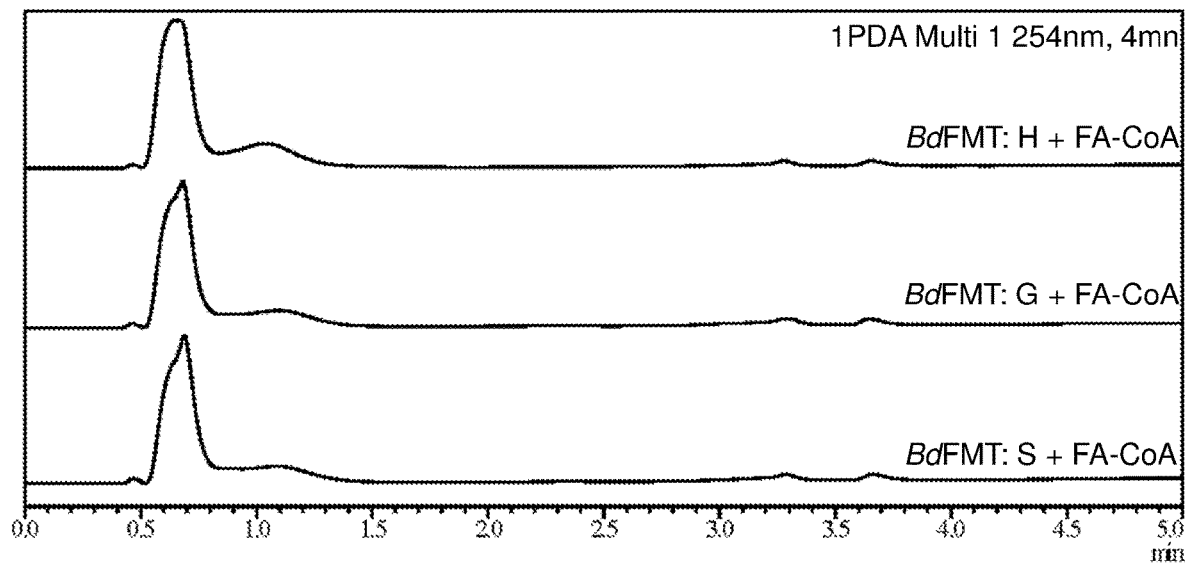
FIGS. 8A and 8B show LC-MS traces of chemical species present after incubating a putative Brachypodium distachyon FMT (BdFMT) with each of p-hydroxycinnamyl alcohol (H), coniferyl alcohol (G), and sinapyl alcohol (S) and either feruloyl-CoA (FA-CoA) (FIG. 8A) or p-coumaroyl-CoA (pCA-CoA) (FIG. 8B).
Figure 8B:
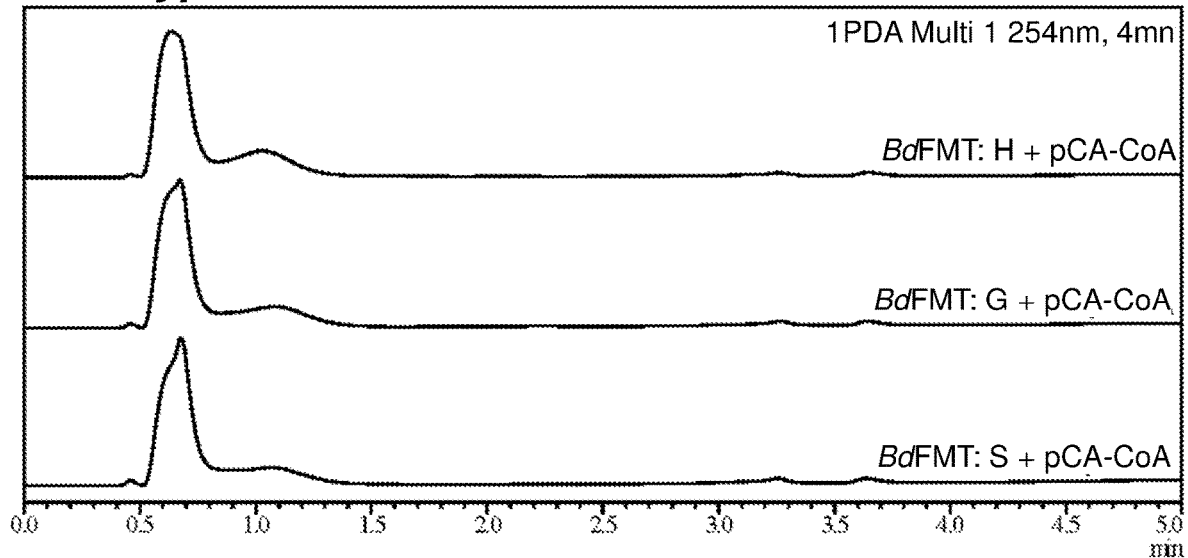

The data show definitive evidence that the putative OsFMT is an active transferase that couples monolignols to both feruloyl-CoA (FIG. 4A and Table 1) and p-coumaroyl-CoA (FIG. 4B and Table 1). BAHD enzymes from maize (*Zea mays*, ZmFMT), sorghum (*Sorghum bicolor*, SbFMT), and switchgrass (*Panicum virgatum*, PvFMT), on the other hand, couple monolignols primarily to feruloyl-CoA (FIGS. 5A, 6A, and 7A and Table 1) and not p-coumaroyl-CoA (FIGS. 5B, 6B, and 7B and Table 1). The selectivity of these enzymes for feruloyl-CoA was not apparent from the gene/enzyme sequence alone and in this regard was unexpected. The homologous enzyme from *Brachypodium distachyon* (BdFMT), by contrast, was found to have no transferase activity for monolignols and either feruloyl-CoA or p-coumaroyl-CoA (FIGS. 8A and 8B and Table 1). The lack of FMT activity of the BdFMT enzyme shows that FMT activity is not apparent from sequence homology to known FMTs, such as OsFMT.

TABLE 1

Sequence and activity characteristics of known and putative FMTs.

| Enzyme | Species | Accession # | AA length | % Identity (Sequence Coverage) vs. AsFMT | % Identity (Sequence Coverage) vs. OsFMT | Activity with H, G, S pCA-CoA | Activity with H, G, S FA-CoA |
|---|---|---|---|---|---|---|---|
| AsFMT | Angelica sinensis | AHL24755 | 442 | — | 23% (95/422) | trace | +++ |
| OsFMT | Oryza sativa | LOC_Os05g19910.1 | 433 | 25% (49/199) | — | ++ | +++ |
| ZmFMT | Zea mays | GRMZM2G130728_P01 | 434 | 27% (34/128) | 73% (318/436) | trace | + |
| PvFMT | Panicum virgatum | Pavir.Ca02673.1 | 436 | 21% (74/351) | 76% (331/437) | + | +++ |
| SbFMT | Sorghum bicolor | Sb08g005680.1 | 441 | 26% (52/203) | 77% (335/436) | + | +++ |
| BdFMT | Brachypodium distachyon | Bradi4g06067.1 | 443 | 22% (91/421) | 69% (304/443) | — | — |

H, p-hydroxycinnamyl alcohol (p-coumaryl alcohol); G, coniferyl alcohol; S, sinapyl alcohol; pCA-CoA, p-coumaroyl-CoA; FA-COA, feruloyl-CoA.

Figure 9:
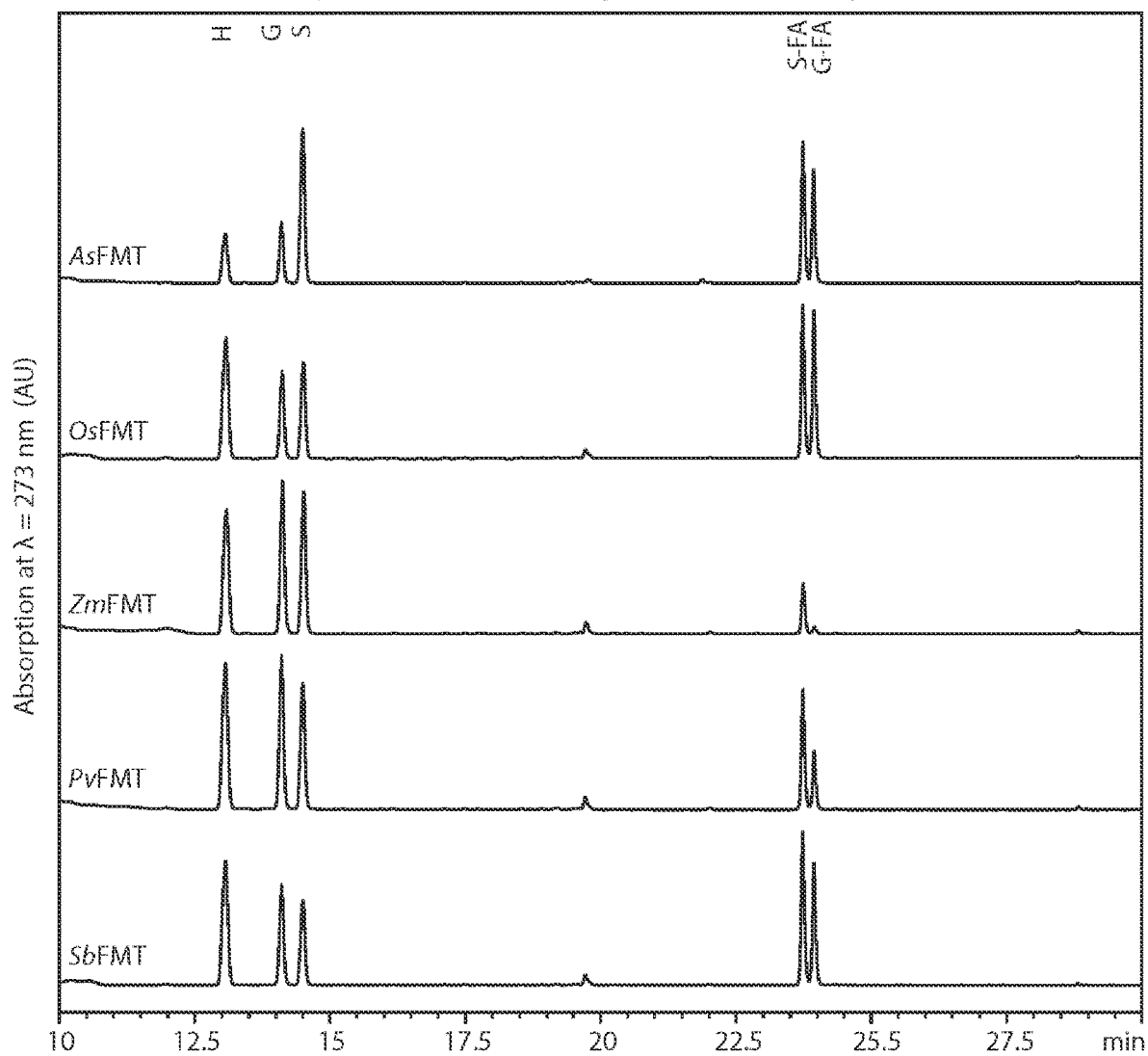
FIG. 9 shows LC-MS traces of chemical species present after incubating each of an FMT from Angelica sinensis (AsFMT) (Wilkerson C G, et al. (2014) Monolignol ferulate transferase introduces chemically labile linkages into the lignin backbone. Science 344(6179):90-93), OsFMT, ZmFMT, PvFMT, and SbFMT with p-hydroxycinnamyl alcohol (H), coniferyl alcohol (G), sinapyl alcohol (S) and feruloyl-CoA. Products include sinapyl ferulate (S-FA) and coniferyl ferulate (G-FA).
Figure 10:
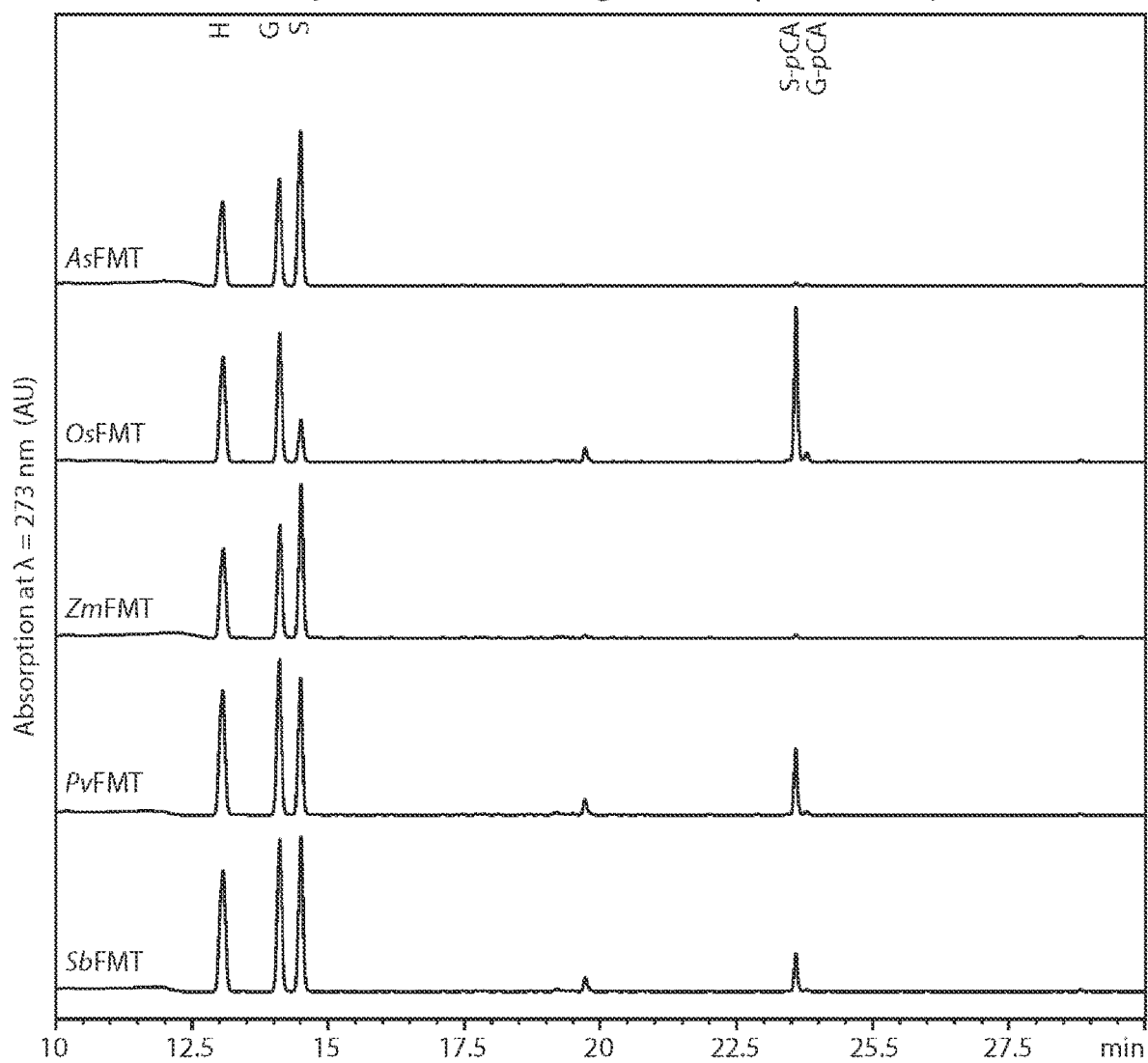
FIG. 10 shows LC-MS traces of chemical species present after incubating each of AsFMT, OsFMT, ZmFMT, PvFMT, and SbFMT with p-hydroxycinnamyl alcohol (H), coniferyl alcohol (G), sinapyl alcohol (S), and p-coumaroyl-CoA. Products include sinapyl coumarate (S-pCA) and coniferyl coumarate (G-pCA).
Figure 11:
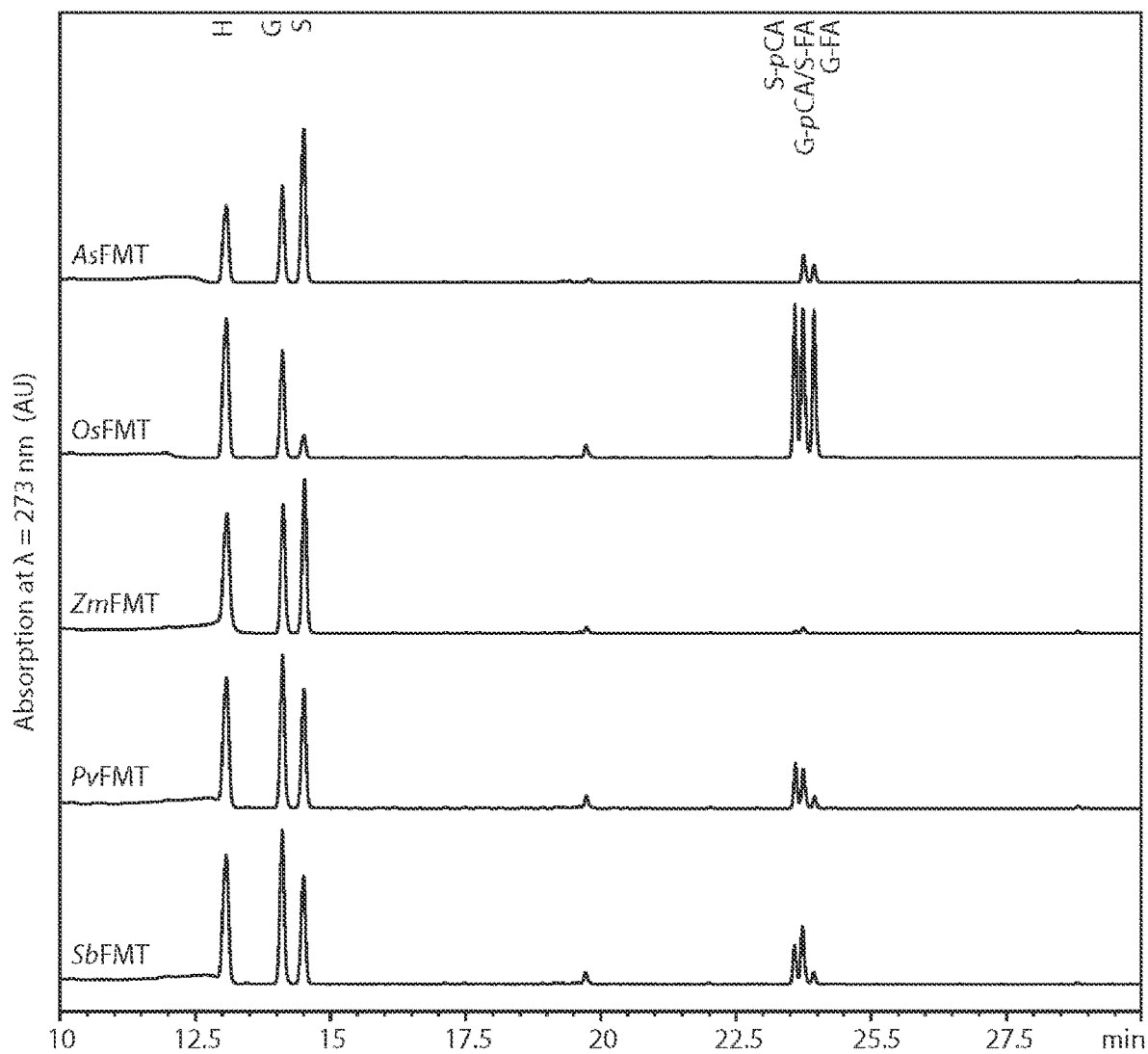
FIG. 11 shows LC-MS traces of chemical species present after incubating each of AsFMT, OsFMT, ZmFMT, PvFMT, and SbFMT with p-hydroxycinnamyl alcohol (H), coniferyl alcohol (G), sinapyl alcohol (S), p-coumaroyl-CoA, and feruloyl-CoA. Products include sinapyl coumarate (S-pCA), coniferyl coumarate (G-pCA), sinapyl ferulate (S-FA), and coniferyl ferulate (G-FA).

Using the cell-free translation system, we expanded the characterization of FMT enzyme function by performing competition assays. The FMT enzymes were fed monolignols (p-coumaryl alcohol, coniferyl alcohol, and sinapyl alcohol) and a mixture of feruloyl-CoA and p-coumaroyl-CoA substrates to determine which CoA ester was preferred by the enzyme when both were present. These experiments were designed to test the specificity of the FMT enzymes for their substrates ZmFMT had strongest activity with feruloyl-CoA and sinapyl alcohol, thereby producing sinapyl ferulate (FIG. 9 and Table 2). When fed both feruloyl-CoA and p-coumaroyl-CoA, the activity of the enzyme appeared to drop significantly, but the substrate preference for ZmFMT remained as feruloyl-CoA and sinapyl alcohol (FIG. 11 and Table 2), suggesting that ZmFMT is specifically an FMT enzyme. The SbFMT enzyme had high production of sinapyl ferulate and coniferyl ferulate when provided feruloyl-CoA and monolignols as substrates (FIG. 9 and Table 2). SbFMT was also capable of producing small amounts of sinapyl p-coumarate when fed p-coumaroyl-CoA and monolignols (FIG. 10 and Table 2). In the feruloyl-CoA and p-coumaroyl-CoA competition assay, SbFMT still preferentially produced sinapyl ferulate (FIG. 11 and Table 2), indicating primary activity as an FMT enzyme. The PvFMT enzyme also produced more sinapyl ferulate when fed feruloyl-CoA than other ferulate conjugates (FIG. 9 and Table 2) and was able to produce sinapyl p-coumarate when fed monolignols and p-coumaroyl-CoA (FIG. 10 and Table 2). In the competition assay, PvFMT produced equal amounts of sinapyl ferulate and sinapyl p-coumarate (FIG. 11 and Table 2), indicating that PvFMT is an FMT enzyme, but also appears capable of functioning as a p-coumaroyl-CoA:monolignol transferase (PMT) when multiple substrates are present.

TABLE 2

Products formed from competition experiments of known and putative FMTs.

| Enzyme | Species | CoA | Monolignol conjugates observed |
|---|---|---|---|
| SbFMT | S. bicolor | pCA-COA | S-pCA >> G-pCA* |
| SbFMT | S. bicolor | FA-COA | S-FA > G-FA |
| SbFMT | S. bicolor | FA-CoA + pCA-CoA | S-FA > S-pCA >> G-FA > G-pCA |
| PvFMT | P. virgatum | pCA-CoA | S-pCA >> G-pCA* |
| PvFMT | P. virgatum | FA-COA | S-FA > G-FA |
| PvFMT | P. virgatum | FA-CoA + pCA-CoA | S-pCA > S-FA >> G-FA > G-pCA |
| ZmFMT | Z. mays | pCA-CoA | S-pCA* |
| ZmFMT | Z. mays | FA-COA | S-FA >> G-FA |
| ZmFMT | Z. mays | FA-CoA + pCA-CoA | S-FA* > S-pCA* |
| AsFMT | A. sinensis | pCA-CoA | S-pCA* ≈ G-pCA* |
| AsFMT | A. sinensis | FA-COA | S-FA > G-FA |
| AsFMT | A. sinensis | FA-CoA + pCA-CoA | S-FA > G-FA |
| OsFMT | O. sativa | pCA-CoA | S-pCA >> G-pCA* |
| OsFMT | O. sativa | FA-COA | S-FA ≈ G-FA |
| OsFMT | O. sativa | FA-CoA + pCA-CoA | S-pCA ≈ S-FA ≈ G-FA |
| Wheat germ | | pCA-COA | No product |
| Wheat germ | | FA-COA | No product |
| Wheat germ | | FA-CoA + pCA-CoA | No product |

*Indicates trace level products (determined by low intensity peaks).
≈ Indicates similar intensity absorption peaks.
> Indicates a preference (stronger peak intensity) for the compound(s) to the left.
>> Indicates a much stronger preference (large difference in peak intensity) for the compound(s) to the left.

Example 2: Analysis of in Planta Expression of Zea mays, Panicum virgatum, and Sorghum bicolor FMTs The data in Example 1 indicate that the SbFMT, PvFMT and ZmFMT enzymes function as feruloyl-CoA monolignol transferases. The present example shows expression and activity of these enzymes in planta.

Methods

Gateway cloning technology (Invitrogen) was used to generate constructs to express the ZmFMT, SbFMT, and PvFMT genes in planta. The gateway constructs generated were: ProUBQ10: ZmFMT-GFP, ProUBQ10: SbFMT-GFP, ProUBQ10: PvFMT-GFP, and ProUBQ10: OsFMT-GFP as a positive control (pUBC:GFP (Grefen C, et al. (2010) A ubiquitin-10 promoter-based vector set for fluorescent protein tagging facilitates temporal stability and native protein distribution in transient and stable expression studies. *The Plant Journal* 64(2):355-365)). The plant expression constructs were introduced into *Agrobacterium tumefaciens* strain GV3101 and transformed into *Arabidopsis thaliana*, ecotype Col-0, using the floral dip method (Clough S J & Bent A F (1998) Floral dip: a simplified method for *Agrobacterium-mediated transformation of *Arabidopsis thaliana*. *Plant Journal* 16(6):735-743) to generate transgenic plants.

Transgenic seeds were sterilized with chlorine gas for 4 h prior to plating on half-strength Murashige and Skoog media (Sigma-Aldrich) with 25 mg/L glufosinate-ammonium (Basta; Fisher) to select for transformants. Seedlings were grown under long-day conditions (16 h light, 8 h dark, 20° C.) for one week and then positive transformants were screened for the presence of GFP. Whole seedlings were placed on a glass slide in water and examined for the presence of GFP using an epifluorescent microscope and a GFP excitation/emission filter set (488/525). Seedlings that showed resistance to Basta and strong fluorescence under the GFP filters were planted in soil and grown under long-day conditions.

After 4-5 weeks, 2-3 small leaves were collected from each plant for genomic DNA extraction and genotyping PCR. Briefly, the leaves were ground in Shorty extraction buffer (200 mM Tris-HCl, 250 mM NaCl, 25 mM NaEDTA, 0.5% SDS) and the samples were then centrifuged for 3 min. The supernatant was then washed with isopropanol (300 µL) and centrifuged again. The DNA pellet was washed with 70% ethanol (500 µL), centrifuged again and then the pellets were allowed to air dry. The DNA was re-suspended in 100 µL of TE buffer, pH 8.0. Genotyping PCR using MangoTaq polymerase (Bioline) was performed to confirm the presence of the ZmFMT, SbFMT, and PvFMT in *Arabidopsis*. Primers were designed to amplify part of Actin2 (At3g18780) from *Arabidopsis* as a positive control for DNA quality. The primers used to amplify the genes are listed in Table 3. PCR cycling conditions were as follows: 94° C. 1 min, (94° C. 10 s, 48° C. 15 s, 72° C. 45 s)×32, 72° C. 5 min, then cooled to 4° C.

TABLE 3

Primer sequences used for amplification of control (Actin 2) and transgenic genes (ZmFMT, SbFMT and PvFMT) in *Arabidopsis* genotyping study.

| Gene | Primers (5'-3') |
|---|---|
| Actin2-F | CCAGAAGGATGCATATGTTGGTGA (SEQ ID NO: 11) |
| Actin2-R | GAGGAGCCTCGGTAAGAAGA (SEQ ID NO: 12) |
| ZmFMT-F | ATGGCGAGCATCACC (SEQ ID NO: 13) |
| ZmFMT-R | AGCAAAGAAGGCTTTCATCTC (SEQ ID NO: 14) |
| SbFMT-F | ATGGCGACGACCATC (SEQ ID NO: 15) |
| SbFMT-R | AGCAAAGAAGGCCTTCA (SEQ ID NO: 16) |
| PvFMT-F | ATGGTGAACATCACCGTG (SEQ ID NO: 17) |
| PvFMT-R | AGCAAAGAAGGCCTTCAT (SEQ ID NO: 18) |

HPLC analysis was performed on a Shimadzu LCMS8040 equipped with a Prominence LC20. The mobile phase was a binary gradient of acetonitrile and water, pumped at 0.7 mL/min through a Phemonenex Kinetex 5µ XB-C18, 100 Å, 250×4.6 mm column (P/N: 00G-4605-E0) equipped with a guard column. The LC program was initially held at 5% acetonitrile for 2 min, then ramped over 28 min to 100% acetonitrile, held there for 4 min and ramped back over 1 min to 5% acetonitrile and held for 15 min. The samples were injected with an autoinjector onto the XB-C18 column and the eluent then flowed through a PDA detector scanning from 250-400 nm and into the MS ionization source operating in DUIS (ESI/APCI) mode with 2.5 L/min nebulizing gas, 15 L/min drying gas, 250° C. DL temperature, and 400° C. heat block. The MS scanned the ions in negative-ion mode from 120-600 m/z. Elution times for the analytes are reported in Table 4.

TABLE 4

Retention times for the monolignols and monolignol conjugates.

| Compound | Retention time |
|---|---|
| p-coumaryl alcohol | 13.07 min |
| coniferyl alcohol | 14.11 min |
| sinapyl alcohol | 14.51 min |
| sinapyl p-coumarate | 23.59 min |
| coniferyl p-coumarate | 23.79 min |
| sinapyl ferulate | 23.73 min |
| coniferyl ferulate | 23.94 min |

Results

The SbFMT, PvFMT and ZmFMT genes (with the OsFMT gene as a positive control) were cloned into the pUBC-GFP destination vector and transformed into *Arabidopsis thaliana*. *Arabidopsis* was used because it is a useful model organism when studying novel monolignol conjugates; *Arabidopsis* does not produce detectable levels of any monolignol conjugate, thereby making the presence and production of monolignol ferulates through the putative FMT enzymes more apparent. The FMT genes were expressed under the control of the *Arabidopsis* Ubiquitin 10 promoter and were fused to a green fluorescent protein (GFP) at the C-terminus. The ubiquitous promoter was chosen because monolignol ferulate conjugates can be difficult to detect in *Arabidopsis* and we therefore sought to achieve the highest expression level possible, with the assumption that it would lead to higher levels of the conjugates. The C-terminal GFP tag allows us to confirm that the FMT enzymes are being produced by the plant and also determine the intracellular location of the enzyme.

Seeds were plated on media containing Basta antibiotic to select for seedlings that contained the proUBQ10-FMT-GFP construct. Before planting, all seedlings were subjected to fluorescence microscopic analysis to confirm the presence of GFP (as a proxy for the presence of the FMT enzyme). Following the development of a healthy rosette (4 weeks after planting), 2-3 small leaves were dissected from each plant and used for genotyping analysis to confirm the presence of the FMT genes in the plants. Plants that did not express the FMT gene were marked as wild-type and will be used as control plants during the chemical analysis of lignin. The genotyping analysis confirmed that ZmFMT, SbFMT, and PvFMT genes have been successfully transformed into *Arabidopsis*. The genes were able to be amplified from the genomic DNA of respective transgenic plants and were not present in wild-type plants. Together with the GFP screening, these data indicate that the transgenes are present in the transgenic *Arabidopsis* and that the protein is being expressed.

Transgenic plants will continue to grow under long-day conditions until senescence, at which point the plants will be harvested for chemical analysis. Wild-type and transgenic plant samples will be ground and solvent extracted to remove water-, ethanol-, and acetone-soluble compounds (basically isolating the plant cell wall). The ground, dried cell wall samples will then be subjected to derivatization followed by reductive cleavage (DFRC) lignin analysis (Karlen S D, et al. (2016) Monolignol ferulate conjugates are naturally incorporated into plant lignins. *Science*

Advances 2(10):e1600393: 1600391-1600399; Lu F & Ralph J (1997) Derivatization followed by reductive cleavage (DFRC method), a new method for lignin analysis: Protocol for analysis of DFRC monomers. *Journal of Agricultural and Food Chemistry* 45(7):2590-2592; Lu F & Ralph J (1999) Detection and determination of p-coumaroylated units in lignins. *Journal of Agricultural and Food Chemistry* 47(5):1988-1992). This assay has been shown to yield peaks that are diagnostic for not only the production of monolignol conjugates (monolignol ferulates and monolignol p-coumarates) but their incorporation into the lignins of transgenic AsFMT *Arabidopsis thaliana* (Smith R A, et al. (2017) Defining the diverse cell populations contributing to lignification in *Arabidopsis* stems. *Plant Physiology* 174(2): 1028-1036; Smith R A, et al. (2015) Engineering monolignol p-coumarate conjugates into Poplar and *Arabidopsis* lignins. *Plant Physiology* 169(4):2992-3001). DFRC analysis is therefore expected to confirm that the ZmFMT, SbFMT and PvFMT enzymes produced by the transgenic *Arabidopsis thaliana* plants have the expected FMT activity in planta and that monolignol ferulates will be produced and form zip-lignins.

Example 3: Sequence Analysis of *Zea mays, Panicum virgatum,* and *Sorghum bicolor* FMTs Clustal Omega (v. 1.2.4) (Sievers F, Wilm A, Dineen D, Gibson T J, Karplus K, Li W, Lopez R, McWilliam H, Remmert M, Soding J, Thompson J D, Higgins D G. Fast, scalable generation of high-quality protein multiple sequence alignments using Clustal Omega. *Mol Syst Biol.* 2011 Oct. 11; 7:539) was used to align the amino acid sequences of ZmFMT, SbFMT, PvFMT, and BdFMT. Sequence alignments of ZmFMT, SbFMT, PvFMT, and BdFMT and of ZmFMT, SbFMT, and PvFMT are shown in FIGS. 12 and 13. These sequence alignments can be used to guide the design of variants of ZmFMT, SbFMT, and PvFMT that maintain FMT activity. The alignment shown in FIG. 13 was used as a basis for enzymes having an amino acid sequence of SEQ ID NO:7. An identity matrix for ZmFMT, SbFMT, PvFMT, and BdFMT is shown in FIG. 14. This identity matrix shows that ZmFMT, SbFMT, and PvFMT are all at least 80% identical with each other and are all less than 80% identical with the non-FMT-active BdFMT.

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and the methods and processes are not necessarily restricted to the orders of steps indicated herein or in the claims. As used herein and in the appended claims, the singular forms "a," "an," and "the" include plural reference unless the context clearly dictates otherwise. Thus, for example, a reference to "a nucleic acid" or "a polypeptide" includes a plurality of such nucleic acids or polypeptides (for example, a solution of nucleic acids or polypeptides or a series of nucleic acid or polypeptide preparations), and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

The following statements of the invention are intended to summarize some aspects of the invention according to the foregoing description given in the specification.

STATEMENTS OF THE INVENTION

1. An isolated nucleic acid encoding a feruloyl-CoA: monolignol transferase wherein the nucleic acid can selectively hybridize to a DNA with a SEQ ID NO:1, SEQ ID NO:3, or SEQ ID NO:5 sequence.
2. The isolated nucleic acid of statement 1, wherein the nucleic acid selectively hybridizes to a DNA with a SEQ ID NO:1, SEQ ID NO:3, or SEQ ID NO:5 sequence under stringent hybridization conditions.
3. The isolated nucleic acid of statement 2, wherein the stringent hybridization conditions comprise a wash in 0.1×SSC, 0.1% SDS at 65° C.
4. The isolated nucleic acid of any of statements 1-3, wherein the nucleic acid that selectively hybridizes to a DNA with a SEQ ID NO:1, SEQ ID NO:3, or SEQ ID NO:5 sequence has at least about 70% sequence identity with SEQ ID NO:1, SEQ ID NO:3, or SEQ ID NO:5.

5. The isolated nucleic acid of any of statements 1-4, wherein the nucleic acid encodes a feruloyl-CoA:monolignol transferase that can catalyze the synthesis of monolignol ferulate(s) from monolignol(s) and feruloyl-CoA.
6. The isolated nucleic acid of statement 5, wherein the monolignol is coniferyl alcohol, p-coumaryl alcohol, sinapyl alcohol or a combination thereof.
7. The isolated nucleic acid of any of statements 1-6, wherein the nucleic acid encodes a feruloyl-CoA:monolignol transferase polypeptide with a SEQ ID NO:2, SEQ ID NO:4, SEQ ID NO:6, or SEQ ID NO:7 sequence.
8. The isolated nucleic acid of any of statements 1-7, wherein the nucleic acid encodes a feruloyl-CoA:monolignol transferase that can catalyze the synthesis of monolignol ferulate(s) from a monolignol(s) and feruloyl-CoA with at least about 50% of the activity of a feruloyl-CoA:monolignol transferase with the SEQ ID NO:2, SEQ ID NO:4, SEQ ID NO:6, or SEQ ID NO:7.
9. A transgenic plant cell comprising the isolated nucleic acid of any of statements 1-8.
10. A transgenic plant comprising the plant cell of statement 9 or the isolated nucleic acid of any of statements 1-8.
11. An expression cassette comprising the feruloyl-CoA:monolignol transferase nucleic acid of any of statements 1-8 operably linked to a promoter functional in a host cell.
12. The expression cassette of statement 11, which further comprises a selectable marker gene.
13. The expression cassette of statement 11 or 12, further comprising plasmid DNA.
14. The expression cassette of any of statements 11-13, wherein the expression cassette is within an expression vector.
15. The expression cassette of any of statements 11-14, wherein the promoter is a promoter functional during plant development or growth.
16. The expression cassette of any of statements 11-15, wherein the promoter is a poplar xylem-specific secondary cell wall specific cellulose synthase 8 promoter, cauliflower mosaic virus promoter, Z10 promoter from a gene encoding a 10 kD zein protein, Z27 promoter from a gene encoding a 27 kD zein protein, pea rbcS gene or actin promoter from rice.
17. A plant cell comprising the expression cassette of any of statements 11-16.
18. The plant cell of statement 17, wherein the plant cell is a monocot cell.
19. The plant cell of statement 17, wherein the plant cell is a maize, grass or softwood cell.
20. The plant cell of statement 17, wherein the plant cell is a dicot cell.
21. The plant cell of statement 17, wherein the plant cell is a hardwood cell. 22. A plant comprising the expression cassette of any of statements 11-16.
23. The plant of statement 22, wherein the plant is a monocot.
24. The plant of statement 22, wherein the plant is a grass, maize or softwood.
25. The plant of statement 22, wherein the plant is a gymnosperm.
26. The plant of statement 22, wherein the plant is a dicot.
27. The plant of statement 22, wherein the dicot is a hardwood.

28. A method for incorporating monolignol ferulates into lignin of a plant, comprising:
   a) stably transforming plant cells with the expression cassette of any of statements 11-16 to generate transformed plant cells;
   b) regenerating the transformed plant cells into at least one transgenic plant, wherein feruloyl-CoA:monolignol transferase is expressed in at least one transgenic plant in an amount sufficient to incorporate monolignol ferulates into the lignin of the transgenic plant.
29. The method of statement 28, wherein the transgenic plant is fertile.
30. The method of statement 28 or 29, further comprising recovering transgenic seeds from the transgenic plant, wherein the transgenic seeds comprise the nucleic acid encoding a feruloyl-CoA:monolignol transferase.
31. The method of any of statements 28-30, wherein the plant is a monocot.
32. The method of any of statements 28-31, wherein the plant is a grass, maize or softwood plant.
33. The method of any of statements 28-32, wherein the plant is a gymnosperm.
34. The method of statement 28, wherein the plant is a dicot.
35. The method of statement 34, wherein the dicot plant is a hardwood.
36. The method of any of statements 28-35, wherein the lignin in the plant comprises at least 1% monolignol ferulate.
37. The method of any of statements 28-36, wherein the lignin in the plant comprises at least 5% monolignol ferulate.
38. The method of any of statements 28-37, wherein the lignin in the plant comprises at least 10% monolignol ferulate.
39. The method of any of statements 28-38, wherein the lignin in the plant comprises at least 20% monolignol ferulate.
40. The method of any of statements 28-39, wherein the lignin in the plant comprises at least 25% monolignol ferulate.
41. The method of any of statements 28-40, wherein the lignin in the plant comprises about 1-30% monolignol ferulate, or about 2-30% monolignol ferulate.
42. The method of any of statements 28-41, further comprising breeding a fertile transgenic plant to yield a progeny plant that has an increase in the percentage of monolignol ferulates in the lignin of the progeny plant relative to the corresponding untransformed plant.
43. The method of any of statements 28-42, further comprising breeding a fertile transgenic plant to yield a progeny plant that has an increase in the percentage of monolignol ferulates in the lignin of the progeny plant as a dominant trait while still maintaining functional agronomic characteristics relative to the corresponding untransformed plant.
44. The method of any of statements 28-43, wherein the transformed plant cell is transformed by a method selected from the group consisting of electroporation, microinjection, microprojectile bombardment, and liposomal encapsulation.
45. The method of any of statements 28-44, further comprising stably transforming the plant cell with at least one selectable marker gene.
46. A fertile transgenic plant having an increased percent of monolignol ferulates in the plant's lignin, the genome of which is stably transformed by the nucleic acid of any of statements 1-8, wherein the nucleic acid is operably linked to a promoter functional in a host cell, and wherein the feruloyl-CoA:monolignol transferase nucleic acid is transmitted through a complete normal sexual cycle of the transgenic plant to the next generation.

47. The plant of statement 46, wherein the plant is a monocot.
48. The plant of statement 46, wherein the plant is a grass, maize or softwood.
49. The plant of statement 46, wherein the plant is a gymnosperm.
50. The plant of statement 46, wherein the plant is a dicot.
51. The plant of statement 46, wherein the percent of monolignol ferulates in the plant's lignin is increased relative to the corresponding untransformed plant.
52. The plant of any of statements 46-51, wherein the percent of monolignol ferulates in the plant's lignin is increased by at least 1% relative to the corresponding untransformed plant.
53. The plant of any of statements 46-52, wherein the percent of monolignol ferulates in the plant's lignin is increased by at least 2-5% relative to the corresponding untransformed plant.
54. The plant of any of statements 46-53, wherein the lignin in the plant comprises at least 1% monolignol ferulates.
55. The plant of any of statements 46-54, wherein the lignin in the plant comprises at least 5% monolignol ferulates.
56. The plant of any of statements 46-55, wherein the lignin in the plant comprises at least 10% monolignol ferulates.
57. The plant of any of statements 46-56, wherein the lignin in the plant comprises at least 20% monolignol ferulates.
58. The plant of any of statements 46-57, wherein the lignin in the plant comprises at least 25% monolignol ferulates.
59. The plant of any of statements 46-58, wherein the lignin in the plant comprises about 1-30% monolignol ferulates.
60. A lignin isolated from a transgenic plant comprising the isolated nucleic of any of statements 1-8.
61. A method of making a product from a transgenic plant comprising:
 (a) providing or obtaining a transgenic plant that includes an isolated nucleic acid encoding a feruloyl-CoA:monolignol transferase comprising the isolated nucleic of any of statements 1-8; and
 (b) processing the transgenic plant's tissues under conditions sufficient to digest the lignin; and thereby generate the product from the transgenic plant,
 wherein the transgenic plant's tissues comprise lignin having an increased percent of monolignol ferulates relative to a corresponding untransformed plant.
62. The method of statement 61, wherein the conditions sufficient to digest the lignin comprise conditions sufficient to cleave ester bonds within monolignol ferulate-containing lignin.
63. The method of statement 61 or 62, wherein the conditions sufficient to digest the lignin comprise mildly alkaline conditions.
64. The method of any of statements 61-63, wherein the conditions sufficient to digest the lignin comprise contacting the transgenic plant's tissues with ammonia for a time and a temperature sufficient to cleave ester bonds within monolignol ferulate-containing lignin.
65. The method of any of statements 61-64, wherein the conditions sufficient to digest the lignin would not cleave substantially any of the ether and carbon-carbon bonds in lignin from a corresponding plant that does not contain the isolated nucleic acid encoding the feruloyl-CoA:monolignol transferase.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

Other embodiments are within the following claims.

We claim:

1. A transgenic plant comprising an isolated nucleic acid molecule, wherein the isolated nucleic acid molecule comprises a nucleotide sequence encoding a polypeptide having feruloyl-CoA:monolignol transferase activity, wherein the polypeptide comprises an amino acid sequence having at least 99% amino acid sequence identity to the amino acid sequence as set forth in SEQ ID NO: 4, wherein the nucleotide sequence is operably linked to a heterologous promoter functional or active in a plant cell, and wherein expression of the polypeptide in the transgenic plant increases percent of monolignol ferulates in the transgenic plant's lignin as compared to a control plant of the same species lacking the isolated nucleic acid molecule and grown under identical conditions.

2. The transgenic plant of claim 1, wherein the transgenic plant does not have an increased percent of monolignol coumarates in the transgenic plant's lignin as compared to the control plant.

3. The transgenic plant of claim 1, wherein genome of the transgenic plant is stably transformed with the isolated nucleic acid molecule.

4. The transgenic plant of claim 1, wherein the heterologous promoter is functional or active during plant growth or development.

5. The transgenic plant of claim 1, wherein the heterologous promoter is functional or active in a woody tissue of a plant.

6. The transgenic plant of claim 1, wherein the polypeptide has the amino acid sequence as set forth in SEQ ID NO:4.

7. A transgenic seed obtained from the transgenic plant of claim 1, wherein the transgenic seed comprises the isolated nucleic acid molecule.

8. The transgenic seed of claim 7, wherein the polypeptide has the amino acid sequence as set forth in SEQ ID NO:4.

9. A method for increasing a content of monolignol ferulates in lignin within a plant, comprising:
(a) planting the transgenic seed of claim 7; and
(b) cultivating a transgenic plant germinated from the transgenic seed, wherein expression of the polypeptide in the germinated transgenic plant increases the content of monolignol ferulates in the lignin within the germinated transgenic plant as compared to a control plant lacking the isolated nucleic acid molecule and grown under identical growth conditions.

10. A method of obtaining a plant having increased content of monolignol ferulates in lignin within the plant, comprising the steps:
(i) stably transforming plant cells with an isolated nucleic acid molecule, wherein the isolated nucleic acid molecule comprises a nucleotide sequence encoding a polypeptide having feruloyl-CoA:monolignol transferase activity, wherein the polypeptide comprises an amino acid sequence having at least 99% amino acid sequence identity to the amino acid sequence as set forth in SEQ ID NO:4, wherein the nucleotide sequence is operably linked to a heterologous promoter functional or active in a plant cell; and
(ii) regenerating a transgenic plant with the stably transformed plant cells from step (i), wherein genome of the regenerated transgenic plant is stably transformed with the isolated nucleic acid molecule, and wherein the regenerated transgenic plant has increased percent of monolignol ferulates in the regenerated transgenic plant's lignin as compared to a control plant of the same species lacking the isolated nucleic acid molecule and grown under identical conditions.

11. The method of claim 10, wherein the polypeptide has the amino acid sequence as set forth in SEQ ID NO:4.

* * * * *

SEQUENCE LISTING

```
<160> NUMBER OF SEQ ID NOS: 18

<210> SEQ ID NO 1
<211> LENGTH: 1302
<212> TYPE: DNA
<213> ORGANISM: Zea mays

<400> SEQUENCE: 1
atggcgagca tcaccgtgac aaggaaatcc caatccttcg tcgtgccatc gtccacgcca      60
actccgacga ccgagacgct cgagttgtcg cccatcgacc gcgttccagg cctgcgccac     120
acggtgcgat ccctgcacgt gttccgccgc aaggacgccg ccgcctccgc cgcccactac     180
gatgctgctg ccgccggcag gccggccgag gtgatccgcg cggcgctgtc ccgcgcgctg     240
gtggactacc gcccgttcgc cggccgtttc gtcggctcac tgtacgccgg ggaggcgagc     300
gttgagtgca ccgacgacgg tgcgtggttc gtggacgctg tcacagattg cagcctcgag     360
gacgtgaacg gcctcgacta cccgcttatg gtctccgagg aagagctgct gccggctcca     420
```

-continued

```
gaggaaggtg ttgacccaac cagtattccg attatgatgc aggtcacgga atttgcttgt     480
ggaggatttg tggtggggct agtcgcagtg cacaccttg  ctgacgggct cggtgcagct     540
caattcatca atgcaatttc tgagtttgcc cgtggagtag ttaaacctac aatagcacct     600
atatgggcac gggagttaat accaaaccca cctaaaatgc ctcctgggcc accaccatcc     660
ttcgagtgct tcgggttcaa acattttgtt atggatgtgg cagttaacaa tattgcacat     720
gtcaagagtg aatactttca aaccaatgga cactattgct ctacatttga tgttgccatt     780
gccaaggttt ggcaagctag acaagggca  atcaagtacg aaccaaattt caaggtgcat     840
gtttgcttct tgccaacac  tcgccacctc ctcacacatg tgctacccaa ggttggtggc     900
ttctatggaa attgcttcta ccagtgact  gtcacagcaa ctgctgaggt agttgctagt     960
tcaagattgc ttgatgtgat taggatgata agggatggga aggctaggct tcctttagag    1020
ttttccagat ggtccacggg caatgtgaaa gtagacccat atcaactaac attcaagcac    1080
aatgttctat ttgtgtccga ttggacacg  cttggattct tgaagttga  ctatgggtgg    1140 ggtgtaccaa accatatcct cccttt cact tatgcagact acatggctgt agcagttctt    1200
ggagctccac cgtctatgaa gaaggggact cgaataatga cacaatgtgt cgaggaggag    1260
catctcgtgg acttcaaggc cgagatgaaa gccttctttt ag                        1302
```

<210> SEQ ID NO 2
<211> LENGTH: 433
<212> TYPE: PRT
<213> ORGANISM: Zea mays

<400> SEQUENCE: 2

```
Met Ala Ser Ile Thr Val Thr Arg Lys Ser Gln Ser Phe Val Val Pro
1               5                   10                  15

Ser Ser Thr Pro Thr Pro Thr Thr Glu Thr Leu Glu Leu Ser Pro Ile
            20                  25                  30

Asp Arg Val Pro Gly Leu Arg His Thr Val Arg Ser Leu His Val Phe
        35                  40                  45

Arg Arg Lys Asp Ala Ala Ala Ser Ala Ala His Tyr Asp Ala Ala Ala
    50                  55                  60

Ala Gly Arg Pro Ala Glu Val Ile Arg Ala Ala Leu Ser Arg Ala Leu
65                  70                  75                  80

Val Asp Tyr Arg Pro Phe Ala Gly Arg Phe Val Gly Ser Leu Tyr Ala
                85                  90                  95

Gly Glu Ala Ser Val Glu Cys Thr Asp Asp Gly Ala Trp Phe Val Asp
            100                 105                 110

Ala Val Thr Asp Cys Ser Leu Glu Asp Val Asn Gly Leu Asp Tyr Pro
        115                 120                 125

Leu Met Val Ser Glu Glu Leu Leu Pro Ala Pro Glu Glu Gly Val
    130                 135                 140

Asp Pro Thr Ser Ile Pro Ile Met Met Gln Val Thr Glu Phe Ala Cys
145                 150                 155                 160

Gly Gly Phe Val Val Gly Leu Val Ala Val His Thr Leu Ala Asp Gly
                165                 170                 175

Leu Gly Ala Ala Gln Phe Ile Asn Ala Ile Ser Glu Phe Ala Arg Gly
            180                 185                 190

Val Val Lys Pro Thr Ile Ala Pro Ile Trp Ala Arg Glu Leu Ile Pro
        195                 200                 205

Asn Pro Pro Lys Met Pro Pro Gly Pro Pro Pro Ser Phe Glu Cys Phe
```

```
            210                 215                 220
Gly Phe Lys His Phe Val Met Asp Val Ala Val Asn Asn Ile Ala His
225                 230                 235                 240

Val Lys Ser Glu Tyr Phe Gln Thr Asn Gly His Tyr Cys Ser Thr Phe
                245                 250                 255

Asp Val Ala Ile Ala Lys Val Trp Gln Ala Arg Thr Arg Ala Ile Lys
                260                 265                 270

Tyr Glu Pro Asn Phe Lys Val His Val Cys Phe Phe Ala Asn Thr Arg
            275                 280                 285

His Leu Leu Thr His Val Leu Pro Lys Val Gly Gly Phe Tyr Gly Asn
        290                 295                 300

Cys Phe Tyr Pro Val Thr Val Thr Ala Thr Ala Glu Val Val Ala Ser
305                 310                 315                 320

Ser Arg Leu Leu Asp Val Ile Arg Met Ile Arg Asp Gly Lys Ala Arg
                325                 330                 335

Leu Pro Leu Glu Phe Ser Arg Trp Ser Thr Gly Asn Val Lys Val Asp
                340                 345                 350

Pro Tyr Gln Leu Thr Phe Lys His Asn Val Leu Phe Val Ser Asp Trp
            355                 360                 365

Thr Arg Leu Gly Phe Phe Glu Val Asp Tyr Gly Trp Gly Val Pro Asn
        370                 375                 380

His Ile Leu Pro Phe Thr Tyr Ala Asp Tyr Met Ala Val Ala Val Leu
385                 390                 395                 400

Gly Ala Pro Pro Ser Met Lys Lys Gly Thr Arg Ile Met Thr Gln Cys
                405                 410                 415

Val Glu Glu Glu His Leu Val Asp Phe Lys Ala Glu Met Lys Ala Phe
            420                 425                 430

Phe

<210> SEQ ID NO 3
<211> LENGTH: 1323
<212> TYPE: DNA
<213> ORGANISM: Sorghum bicolor

<400> SEQUENCE: 3
atggcgacga ccatcatcac ggtgacaagg aaatcccagt cgttcgtcgt gccgtcgtcg      60
tcgtccgcgc cggtgccgac gacggccgaa acgctggagc tgtcggccat cgaccgcgtg     120
ccggggctgc gccacacggt gcggtccctg cacgtgttcc gccgcaaggc ggacgacgac     180
gccgccgccg ccgccgctgc tgccagcagg aggcctgcgg aggtgatccg ggcagcgctg     240
tcccgcgctc tggtggacta ccgtccgttc gccggccgct tcgtcggctc gctgtacgcc     300
ggggaggcgt cgtcgagtg caccgacgag gcgcctggt tcgtggaggc cgtcgctgac      360
tgcagcctcg atgacgtgaa cggcctcgac gactacccgc tcatggtctc cgaggaagag     420
ctgctgccgg cccagagga aggtgttgac cctaccagta ttcccatgat gatgcaggtc     480 acggaattt cttgtggagg atttgtggtg gggctggtcg cagtccacac ccttgcagat     540
gggctcggtg cagctcaatt catcaatgca atttccgagt ttgcccgtgg actagataaa     600
cttacaatag cacctgtgtg ggctcggtcg ttaataccaa acccacctaa gctgcctcct     660
gcgccgccac catcctttga gtcctttggg ttcaaacatt ttgtcatgga tgttactttt     720
gacaatattg cacatgtcaa gactgagtac tttcaagcca atggacaata ctgctctaca     780
ttcgatgttg ccattgccaa ggtttggcaa gctaggacca gggcaatcaa gtacaatcca     840
```

```
gatgtcaagg tccatgtttg cttctttgcc aacactcgcc acctcctcac acgggagctt      900
ccaaacgatg ggggcttcta tggaaattgc ttctatccgg tgactgtaac agcaactgct      960
gagggtgttg ctagtggagg attgcatgat gtgattagga tgatacggga tgggaaggct     1020
aggctgcctt tggagtttgc caaatggtcc atgggtgatg tgaaggtaga cccatatcaa     1080
ctgacattca agcacaatgt tctgtttgtg tctgattgga cgaggcttgg attctttgag     1140
gttgactatg ggtggggtgt accaaaccat atcataccct tcacttatgc agactacatg     1200
gctgtagcag ttcttggggc tccacctact acagtgaaga caaggggac tcgaataatg      1260 acacagtgcg tggaggagaa gcatctcatg gaattcaagg atgagatgaa ggccttcttt     1320
tag                                                                  1323
```

<210> SEQ ID NO 4
<211> LENGTH: 440
<212> TYPE: PRT
<213> ORGANISM: Sorghum bicolor

<400> SEQUENCE: 4

```
Met Ala Thr Thr Ile Ile Thr Val Thr Arg Lys Ser Gln Ser Phe Val
1               5                   10                  15

Val Pro Ser Ser Ser Ala Pro Val Pro Thr Thr Ala Glu Thr Leu
            20                  25                  30

Glu Leu Ser Ala Ile Asp Arg Val Pro Gly Leu Arg His Thr Val Arg
        35                  40                  45

Ser Leu His Val Phe Arg Arg Lys Ala Asp Asp Ala Ala Ala Ala
    50                  55                  60

Ala Ala Ala Ser Arg Arg Pro Ala Glu Val Ile Arg Ala Ala Leu
65                  70                  75                  80

Ser Arg Ala Leu Val Asp Tyr Arg Pro Phe Ala Gly Arg Phe Val Gly
                85                  90                  95

Ser Leu Tyr Ala Gly Glu Ala Cys Val Glu Cys Thr Asp Glu Gly Ala
            100                 105                 110

Trp Phe Val Glu Ala Val Ala Asp Cys Ser Leu Asp Asp Val Asn Gly
        115                 120                 125

Leu Asp Asp Tyr Pro Leu Met Val Ser Glu Glu Leu Leu Pro Ala
    130                 135                 140

Pro Glu Glu Gly Val Asp Pro Thr Ser Ile Pro Met Met Met Gln Val
145                 150                 155                 160

Thr Glu Phe Ser Cys Gly Gly Phe Val Val Gly Leu Val Ala Val His
                165                 170                 175

Thr Leu Ala Asp Gly Leu Gly Ala Ala Gln Phe Ile Asn Ala Ile Ser
            180                 185                 190

Glu Phe Ala Arg Gly Leu Asp Lys Leu Thr Ile Ala Pro Val Trp Ala
        195                 200                 205

Arg Ser Leu Ile Pro Asn Pro Lys Leu Pro Pro Ala Pro Pro Pro
    210                 215                 220

Ser Phe Glu Ser Phe Gly Phe Lys His Phe Val Met Asp Val Thr Phe
225                 230                 235                 240

Asp Asn Ile Ala His Val Lys Thr Glu Tyr Phe Gln Ala Asn Gly Gln
                245                 250                 255

Tyr Cys Ser Thr Phe Asp Val Ala Ile Ala Lys Val Trp Gln Ala Arg
            260                 265                 270

Thr Arg Ala Ile Lys Tyr Asn Pro Asp Val Lys Val His Val Cys Phe
        275                 280                 285
```

```
Phe Ala Asn Thr Arg His Leu Leu Thr Arg Glu Leu Pro Asn Asp Gly
    290                 295                 300
Gly Phe Tyr Gly Asn Cys Phe Tyr Pro Val Thr Val Thr Ala Thr Ala
305                 310                 315                 320
Glu Gly Val Ala Ser Gly Gly Leu His Asp Val Ile Arg Met Ile Arg
                325                 330                 335
Asp Gly Lys Ala Arg Leu Pro Leu Glu Phe Ala Lys Trp Ser Met Gly
            340                 345                 350
Asp Val Lys Val Asp Pro Tyr Gln Leu Thr Phe Lys His Asn Val Leu
        355                 360                 365
Phe Val Ser Asp Trp Thr Arg Leu Gly Phe Phe Glu Val Asp Tyr Gly
    370                 375                 380
Trp Gly Val Pro Asn His Ile Ile Pro Phe Thr Tyr Ala Asp Tyr Met
385                 390                 395                 400
Ala Val Ala Val Leu Gly Ala Pro Pro Thr Thr Val Lys Asn Lys Gly
                405                 410                 415
Thr Arg Ile Met Thr Gln Cys Val Glu Glu Lys His Leu Met Glu Phe
            420                 425                 430
Lys Asp Glu Met Lys Ala Phe Phe
        435                 440

<210> SEQ ID NO 5
<211> LENGTH: 1308
<212> TYPE: DNA
<213> ORGANISM: Panicum virgatum

<400> SEQUENCE: 5
atggtgaaca tcaccgtgac aaggaaatcc cagtccttcg tcgtgccggc gtcgtccgag    60
ccggcgtcgg ccgagacgac gctcgagcta tcggcgatcg accgcgtgcc gggcctccgc   120
cacacggtgc ggtcgctgca cgtgttccgc aacaagaagg agtccgccgc aggcgccggc   180
tgcgacgacg acgatgctgc cagcaggccg ggggaggtga tccgcgcggc gctgtcccgc   240
gcgctggtgg attaccgccc gttcgccggc cgcttcgtcg gctcggtcgc cgccggggag   300
acctgcgtcg agtgcaccga cgacggcgcg tggttcgtgg aggccgtcgc cgactgcagt   360
ctcgagggcg tgaatggcct cgactacccg ctcatggtct ccgaggaaga gctgctgccc   420
gctccagagg aaggcgttga ccctacaagt attccgatca tgatgcaggt tacagaattt   480
gcatgcggag gatttgtggt tgggctggta gcagtccaca ctcttgctga cgggctcggc   540
gccgcccaat tcatcaacgc gatttctgag tttgctcgtg ggatggaaaa gcccacggta   600
gcacccgtat gggctcgggc tttaatacca aacccaccca aactgcttcc cggggcacca   660
ccgtccttca gtcctttggg gttccagcac ttcaccgtgg atgtgacctc tgaccggatt   720
gcctacgtca agacccagta ccatcaggcc actggacagt actgctccac ctttgatgtc   780
gccattgcca aggtttggca ggcaagaacc aaggcaatca agtacagctt ggagtcccaa   840
gttcatgtct gcttcttcgc caacacccgc cacctcctca cccaggtgct gcccaagaat   900
gggggattct atggcaactg cttctaccca gtttctgtga cggccactgc tgaggatgtt   960
gtcactgcag ggttgcttga tgtgatcagg atgataagga tgggaaggc caggcttccc  1020 ctggagtttt ccaagtgggc agcaggggat gtgagtgtgg atccatacca gttgacattt  1080
gagcacaacg tgttgtttgt gtctgattgg acgagacttg ggttctccga ggttgactat  1140
gggtggggtg taccggatca tatcgtgcca ttcacctatg cagactacat ggcggtggcg  1200
```

```
gttcttgggg ctccgccttc gccgaagaag ggaactcgga ttatgacgca gtgtgtggag      1260
gagaagcacc tcatggactt caaggatgag atgaaggcct tcttttag                   1308
```

<210> SEQ ID NO 6
<211> LENGTH: 435
<212> TYPE: PRT
<213> ORGANISM: Panicum virgatum

<400> SEQUENCE: 6

```
Met Val Asn Ile Thr Val Thr Arg Lys Ser Gln Ser Phe Val Val Pro
1               5                   10                  15

Ala Ser Ser Glu Pro Ala Ser Ala Glu Thr Thr Leu Glu Leu Ser Ala
            20                  25                  30

Ile Asp Arg Val Pro Gly Leu Arg His Thr Val Arg Ser Leu His Val
        35                  40                  45

Phe Arg Asn Lys Lys Glu Ser Ala Ala Gly Ala Gly Cys Asp Asp Asp
    50                  55                  60

Asp Ala Ala Ser Arg Pro Gly Glu Val Ile Arg Ala Ala Leu Ser Arg
65                  70                  75                  80

Ala Leu Val Asp Tyr Arg Pro Phe Ala Gly Arg Phe Val Gly Ser Val
                85                  90                  95

Ala Ala Gly Glu Thr Cys Val Glu Cys Thr Asp Asp Gly Ala Trp Phe
            100                 105                 110

Val Glu Ala Val Ala Asp Cys Ser Leu Glu Gly Val Asn Gly Leu Asp
        115                 120                 125

Tyr Pro Leu Met Val Ser Glu Glu Leu Leu Pro Ala Pro Glu Glu
    130                 135                 140

Gly Val Asp Pro Thr Ser Ile Pro Ile Met Met Gln Val Thr Glu Phe
145                 150                 155                 160

Ala Cys Gly Gly Phe Val Val Gly Leu Val Ala Val His Thr Leu Ala
                165                 170                 175

Asp Gly Leu Gly Ala Ala Gln Phe Ile Asn Ala Ile Ser Glu Phe Ala
            180                 185                 190

Arg Gly Met Glu Lys Pro Thr Val Ala Pro Val Trp Ala Arg Ala Leu
        195                 200                 205

Ile Pro Asn Pro Pro Lys Leu Leu Pro Gly Ala Pro Pro Ser Phe Lys
    210                 215                 220

Ser Phe Gly Phe Gln His Phe Thr Val Asp Val Thr Ser Asp Arg Ile
225                 230                 235                 240

Ala Tyr Val Lys Thr Gln Tyr His Gln Ala Thr Gly Gln Tyr Cys Ser
                245                 250                 255

Thr Phe Asp Val Ala Ile Ala Lys Val Trp Gln Ala Arg Thr Lys Ala
            260                 265                 270

Ile Lys Tyr Ser Leu Glu Ser Gln Val His Val Cys Phe Phe Ala Asn
        275                 280                 285

Thr Arg His Leu Leu Thr Gln Val Leu Pro Lys Asn Gly Gly Phe Tyr
    290                 295                 300

Gly Asn Cys Phe Tyr Pro Val Ser Val Thr Ala Thr Ala Glu Asp Val
305                 310                 315                 320

Val Thr Ala Gly Leu Leu Asp Val Ile Arg Met Ile Arg Asn Gly Lys
                325                 330                 335

Ala Arg Leu Pro Leu Glu Phe Ser Lys Trp Ala Ala Gly Asp Val Ser
            340                 345                 350

Val Asp Pro Tyr Gln Leu Thr Phe Glu His Asn Val Leu Phe Val Ser
```

```
                355                 360                 365
Asp Trp Thr Arg Leu Gly Phe Ser Glu Val Asp Tyr Gly Trp Gly Ala
    370                 375                 380

Pro Asp His Ile Val Pro Phe Thr Tyr Ala Asp Tyr Met Ala Val Ala
385                 390                 395                 400

Val Leu Gly Ala Pro Pro Ser Pro Lys Lys Gly Thr Arg Ile Met Thr
                405                 410                 415

Gln Cys Val Glu Glu Lys His Leu Met Asp Phe Lys Asp Glu Met Lys
            420                 425                 430

Ala Phe Phe
        435

<210> SEQ ID NO 7
<211> LENGTH: 442
<212> TYPE: PRT
<213> ORGANISM: Artificial Sequence
<220> FEATURE:
<223> OTHER INFORMATION: Feruloyl-CoA:Monolignol Transferase
<220> FEATURE:
<221> NAME/KEY: misc_feature
<222> LOCATION: (2)..(2)
<223> OTHER INFORMATION: Xaa = A; V; or a conservative substitution of
      A or V
<220> FEATURE:
<221> NAME/KEY: misc_feature
<222> LOCATION: (3)..(3)
<223> OTHER INFORMATION: Xaa = T; a conservative substitution of T; a
      non-conservative substitution of T; or absent
<220> FEATURE:
<221> NAME/KEY: misc_feature
<222> LOCATION: (4)..(4)
<223> OTHER INFORMATION: Xaa = T; a conservative substitution of T; a
      non-conservative substitution of T; or absent
<220> FEATURE:
<221> NAME/KEY: misc_feature
<222> LOCATION: (5)..(5)
<223> OTHER INFORMATION: Xaa = I; S; N; a conservative substitution of
      I, S, or N; or a non-conservative substitution of I, S, or N
<220> FEATURE:
<221> NAME/KEY: misc_feature
<222> LOCATION: (19)..(19)
<223> OTHER INFORMATION: Xaa = S; A; or a conservative substitution of
      S or A
<220> FEATURE:
<221> NAME/KEY: misc_feature
<222> LOCATION: (21)..(21)
<223> OTHER INFORMATION: Xaa = S; T; or a conservative substitution of
      S or T
<220> FEATURE:
<221> NAME/KEY: misc_feature
<222> LOCATION: (22)..(22)
<223> OTHER INFORMATION: Xaa = S; P; E; a conservative substitution of
      S, P, or E; or a nonconservative substitution of S, P, or E
<220> FEATURE:
<221> NAME/KEY: misc_feature
<222> LOCATION: (23)..(23)
<223> OTHER INFORMATION: Xaa = A; T; P; a conservative substitution of
      A, T, or P; or a nonconservative substitution of A, T, or P
<220> FEATURE:
<221> NAME/KEY: misc_feature
<222> LOCATION: (24)..(24)
<223> OTHER INFORMATION: Xaa = P; A; or a conservative substitution of
      P or A; or a nonconservative substitution of P or A
<220> FEATURE:
<221> NAME/KEY: misc_feature
<222> LOCATION: (25)..(25)
<223> OTHER INFORMATION: Xaa = V; a conservative substitution of V; a
      nonconservative substitution of V; or absent
<220> FEATURE:
<221> NAME/KEY: misc_feature
<222> LOCATION: (26)..(26)
<223> OTHER INFORMATION: Xaa = P; a conservative substitution of P; a
      nonconservative substitution of P; or absent
```

```
<220> FEATURE:
<221> NAME/KEY: misc_feature
<222> LOCATION: (27)..(27)
<223> OTHER INFORMATION: Xaa = T; S; a conservative substitution of T
      or S; a nonconservative substitution of T or S; or absent
<220> FEATURE:
<221> NAME/KEY: misc_feature
<222> LOCATION: (28)..(28)
<223> OTHER INFORMATION: Xaa = T; A; a conservative substitution  of T
      or A; or nonconservative substitution of T or A
<220> FEATURE:
<221> NAME/KEY: misc_feature
<222> LOCATION: (29)..(29)
<223> OTHER INFORMATION: Xaa = A; T; E; a conservative substitution of
      A, T, or E; or a nonconservative substitution of A, T, or E
<220> FEATURE:
<221> NAME/KEY: misc_feature
<222> LOCATION: (30)..(30)
<223> OTHER INFORMATION: Xaa = E; T; a conservative substitution of E or
      T; or a nonconservative substitution of E or T
<220> FEATURE:
<221> NAME/KEY: misc_feature
<222> LOCATION: (36)..(36)
<223> OTHER INFORMATION: Xaa = A; P; a conservative substitution or A or
      P; or a nonconservative substitution of A or P
<220> FEATURE:
<221> NAME/KEY: misc_feature
<222> LOCATION: (55)..(55)
<223> OTHER INFORMATION: Xaa = R; N; a conservative substitution  of R
      or N; or a nonconservative substitution of R or N
<220> FEATURE:
<221> NAME/KEY: misc_feature
<222> LOCATION: (57)..(57)
<223> OTHER INFORMATION: Xaa = A; D; K; a conservative substitution of
      A, D, or K; or a nonconservative substitution of A, D, or K
<220> FEATURE:
<221> NAME/KEY: misc_feature
<222> LOCATION: (58)..(58)
<223> OTHER INFORMATION: Xaa = D; A; E; a conservative substitution of
      D, A, or E; or a nonconservative substitution of D, A, or E
<220> FEATURE:
<221> NAME/KEY: misc_feature
<222> LOCATION: (59)..(59)
<223> OTHER INFORMATION: Xaa = D; A; S; a conservative substitution of
      D, A, or S; or a nonconservative substitution of D, A, or S
<220> FEATURE:
<221> NAME/KEY: misc_feature
<222> LOCATION: (60)..(60)
<223> OTHER INFORMATION: Xaa = D; A; a conservative substitution of D or
      A; or a nonconservative substitution of D or A
<220> FEATURE:
<221> NAME/KEY: misc_feature
<222> LOCATION: (61)..(61)
<223> OTHER INFORMATION: Xaa = A; S; a conservative substitution of A
      or S; or a nonconservative substitution of A or S
<220> FEATURE:
<221> NAME/KEY: misc_feature
<222> LOCATION: (62)..(62)
<223> OTHER INFORMATION: Xaa = A; G; a conservative substitution of A or
      G; or a nonconservative substitution of A or G
<220> FEATURE:
<221> NAME/KEY: misc_feature
<222> LOCATION: (63)..(63)
<223> OTHER INFORMATION: Xaa = A; a conservative substitution of A; a
      nonconservative substitution of A; or absent
<220> FEATURE:
<221> NAME/KEY: misc_feature
<222> LOCATION: (64)..(64)
<223> OTHER INFORMATION: Xaa = G; a conservative substitution of G; a
      nonconservative substitution of G; or absent
<220> FEATURE:
<221> NAME/KEY: misc_feature
<222> LOCATION: (65)..(65)
<223> OTHER INFORMATION: Xaa = A; H; C; a conservative substitution of
      A, H, or C; or a nonconservative substitution of A, H, or C
<220> FEATURE:
<221> NAME/KEY: misc_feature
<222> LOCATION: (66)..(66)
<223> OTHER INFORMATION: Xaa = A; Y; D; a conservative substitution of
```

-continued

```
      A, Y, or D; or a nonconservative substitution of A, Y, or D
<220> FEATURE:
<221> NAME/KEY: misc_feature
<222> LOCATION: (67)..(67)
<223> OTHER INFORMATION: Xaa = A; D; a conservative substitution of A or
      D; or a nonconservative substitution of A or D
<220> FEATURE:
<221> NAME/KEY: misc_feature
<222> LOCATION: (68)..(68)
<223> OTHER INFORMATION: Xaa = A; D; a conservative substitution of A or
      D; or a nonconservative substitution of A or D
<220> FEATURE:
<221> NAME/KEY: misc_feature
<222> LOCATION: (69)..(69)
<223> OTHER INFORMATION: Xaa = A; D; a conservative substitution of A or
      D; or a nonconservative substitution of A or D
<220> FEATURE:
<221> NAME/KEY: misc_feature
<222> LOCATION: (70)..(70)
<223> OTHER INFORMATION: Xaa = A; a conservative substitution of A; or a
      nonconservative substitution of A
<220> FEATURE:
<221> NAME/KEY: misc_feature
<222> LOCATION: (71)..(71)
<223> OTHER INFORMATION: Xaa = S; A; a conservative substitution of S or
      A; or a nonconservative substitution of S or A
<220> FEATURE:
<221> NAME/KEY: misc_feature
<222> LOCATION: (72)..(72)
<223> OTHER INFORMATION: Xaa = R; G; S; a conservative substitution of
      R, G, or S; or a nonconservative substitution of R, G, or S
<220> FEATURE:
<221> NAME/KEY: misc_feature
<222> LOCATION: (75)..(75)
<223> OTHER INFORMATION: Xaa = A; G; or a conservative substitution of
      A or G
<220> FEATURE:
<221> NAME/KEY: misc_feature
<222> LOCATION: (100)..(100)
<223> OTHER INFORMATION: Xaa = L; V; or a conservative substitution of
      L or V
<220> FEATURE:
<221> NAME/KEY: misc_feature
<222> LOCATION: (101)..(101)
<223> OTHER INFORMATION: Xaa = Y; A; a conservative substitution of Y or
      A; or a nonconservative substitution of Y or A
<220> FEATURE:
<221> NAME/KEY: misc_feature
<222> LOCATION: (105)..(105)
<223> OTHER INFORMATION: Xaa = A; T; or a conservative substitution of
      A or T
<220> FEATURE:
<221> NAME/KEY: misc_feature
<222> LOCATION: (106)..(106)
<223> OTHER INFORMATION: Xaa = C; S; or a conservative substitution of
      C or S
<220> FEATURE:
<221> NAME/KEY: misc_feature
<222> LOCATION: (112)..(112)
<223> OTHER INFORMATION: Xaa = E; D; or a conservative substitution of
      E or D
<220> FEATURE:
<221> NAME/KEY: misc_feature
<222> LOCATION: (118)..(118)
<223> OTHER INFORMATION: Xaa = E; D; or a conservative substitution of
      E or D
<220> FEATURE:
<221> NAME/KEY: misc_feature
<222> LOCATION: (121)..(121)
<223> OTHER INFORMATION: Xaa = A; T; or a conservative substitution of
      A or T
<220> FEATURE:
<221> NAME/KEY: misc_feature
<222> LOCATION: (126)..(126)
<223> OTHER INFORMATION: Xaa = D; E; or a conservative substitution of
      D or E
<220> FEATURE:
<221> NAME/KEY: misc_feature
<222> LOCATION: (127)..(127)
```

```
<223> OTHER INFORMATION: Xaa = D; G; or a conservative substitution of
      D or G
<220> FEATURE:
<221> NAME/KEY: misc_feature
<222> LOCATION: (132)..(132)
<223> OTHER INFORMATION: Xaa = D; a conservative substitution of D; a
      nonconservative substitution of D; or absent
<220> FEATURE:
<221> NAME/KEY: misc_feature
<222> LOCATION: (158)..(158)
<223> OTHER INFORMATION: Xaa = M; I; or a conservative substitution of
      M or I
<220> FEATURE:
<221> NAME/KEY: misc_feature
<222> LOCATION: (166)..(166)
<223> OTHER INFORMATION: Xaa = S; A; or a conservative substitution of
      S or A
<220> FEATURE:
<221> NAME/KEY: misc_feature
<222> LOCATION: (200)..(200)
<223> OTHER INFORMATION: Xaa = L; V; M; or a conservative substitution
      of L, V, or M
<220> FEATURE:
<221> NAME/KEY: misc_feature
<222> LOCATION: (201)..(201)
<223> OTHER INFORMATION: Xaa = D; V; E; a conservative substitution of
      D, V, or E; or a nonconservative substitution of D, V, or E
<220> FEATURE:
<221> NAME/KEY: misc_feature
<222> LOCATION: (203)..(203)
<223> OTHER INFORMATION: Xaa = L; P; a conservative substitution of L or
      P; or a nonconservative substitution of L or P
<220> FEATURE:
<221> NAME/KEY: misc_feature
<222> LOCATION: (205)..(205)
<223> OTHER INFORMATION: Xaa = I; V; or a conservative substitution of
      I or V
<220> FEATURE:
<221> NAME/KEY: misc_feature
<222> LOCATION: (208)..(208)
<223> OTHER INFORMATION: Xaa = V; I; or a conservative substitution of
      V or I
<220> FEATURE:
<221> NAME/KEY: misc_feature
<222> LOCATION: (212)..(212)
<223> OTHER INFORMATION: Xaa = S; E; A; a conservative substitution of
      S, E, or A; or a nonconservative substitution of S, E, or A
<220> FEATURE:
<221> NAME/KEY: misc_feature
<222> LOCATION: (220)..(220)
<223> OTHER INFORMATION: Xaa = L; M; or a conservative substitution of
      L or M
<220> FEATURE:
<221> NAME/KEY: misc_feature
<222> LOCATION: (221)..(221)
<223> OTHER INFORMATION: Xaa = P; L; a conservative substitution of P or
      L; or a nonconservative substitution of P or L
<220> FEATURE:
<221> NAME/KEY: misc_feature
<222> LOCATION: (223)..(223)
<223> OTHER INFORMATION: Xaa = A; G; or a conservative substitution of
      A or G
<220> FEATURE:
<221> NAME/KEY: misc_feature
<222> LOCATION: (224)..(224)
<223> OTHER INFORMATION: Xaa = P; A; a conservative substitution of P or
      A; or a nonconservative substitution of P or A
<220> FEATURE:
<221> NAME/KEY: misc_feature
<222> LOCATION: (229)..(229)
<223> OTHER INFORMATION: Xaa = E; K; or a conservative substitution of
      E or K
<220> FEATURE:
<221> NAME/KEY: misc_feature
<222> LOCATION: (230)..(230)
<223> OTHER INFORMATION: Xaa = S; C; or a conservative substitution of
      S or C
<220> FEATURE:
<221> NAME/KEY: misc_feature
```

```
<222> LOCATION: (234)..(234)
<223> OTHER INFORMATION: Xaa = K; Q; or a conservative substitution of
      K or Q
<220> FEATURE:
<221> NAME/KEY: misc_feature
<222> LOCATION: (237)..(237)
<223> OTHER INFORMATION: Xaa = V; T; or a conservative substitution of
      V or T
<220> FEATURE:
<221> NAME/KEY: misc_feature
<222> LOCATION: (238)..(238)
<223> OTHER INFORMATION: Xaa = M; V; or a conservative substitution of
      M or V
<220> FEATURE:
<221> NAME/KEY: misc_feature
<222> LOCATION: (241)..(241)
<223> OTHER INFORMATION: Xaa = T; A; or a conservative substitution of
      T or A
<220> FEATURE:
<221> NAME/KEY: misc_feature
<222> LOCATION: (242)..(242)
<223> OTHER INFORMATION: Xaa = F; V; S; or a conservative substitution
      of F, V, or S
<220> FEATURE:
<221> NAME/KEY: misc_feature
<222> LOCATION: (243)..(243)
<223> OTHER INFORMATION: Xaa = D; N; or a conservative substitution of
      D or N
<220> FEATURE:
<221> NAME/KEY: misc_feature
<222> LOCATION: (244)..(244)
<223> OTHER INFORMATION: Xaa = N; R; or a conservative substitution of
      N or R
<220> FEATURE:
<221> NAME/KEY: misc_feature
<222> LOCATION: (247)..(247)
<223> OTHER INFORMATION: Xaa = H; Y; or a conservative substitution of
      H or Y
<220> FEATURE:
<221> NAME/KEY: misc_feature
<222> LOCATION: (250)..(250)
<223> OTHER INFORMATION: Xaa = T; S; or a conservative substitution of
      T or S
<220> FEATURE:
<221> NAME/KEY: misc_feature
<222> LOCATION: (251)..(251)
<223> OTHER INFORMATION: Xaa = E; Q; or a conservative substitution of
      E or Q
<220> FEATURE:
<221> NAME/KEY: misc_feature
<222> LOCATION: (253)..(253)
<223> OTHER INFORMATION: Xaa = F; H; or a conservative substitution of
      F or H
<220> FEATURE:
<221> NAME/KEY: misc_feature
<222> LOCATION: (255)..(255)
<223> OTHER INFORMATION: Xaa = A; T; or a conservative substitution of
      A or T
<220> FEATURE:
<221> NAME/KEY: misc_feature
<222> LOCATION: (256)..(256)
<223> OTHER INFORMATION: Xaa = N; T; or a conservative substitution of
      N or T
<220> FEATURE:
<221> NAME/KEY: misc_feature
<222> LOCATION: (258)..(258)
<223> OTHER INFORMATION: Xaa = Q; H; or a conservative substitution of
      Q or H
<220> FEATURE:
<221> NAME/KEY: misc_feature
<222> LOCATION: (276)..(276)
<223> OTHER INFORMATION: Xaa = R; K; or a conservative substitution of
      R or K
<220> FEATURE:
<221> NAME/KEY: misc_feature
<222> LOCATION: (281)..(281)
<223> OTHER INFORMATION: Xaa = N; E; S; or a conservative substitution
      of N, E, or S
<220> FEATURE:
```

```
<221> NAME/KEY: misc_feature
<222> LOCATION: (282)..(282)
<223> OTHER INFORMATION: Xaa = P; L; a conservative substitution of P or
      L; or a nonconservative substitution of P or L
<220> FEATURE:
<221> NAME/KEY: misc_feature
<222> LOCATION: (283)..(283)
<223> OTHER INFORMATION: Xaa = D; N; E; or a conservative substitution
      of D, N, or E
<220> FEATURE:
<221> NAME/KEY: misc_feature
<222> LOCATION: (284)..(284)
<223> OTHER INFORMATION: Xaa = V; F; S; or a conservative substitution
      of V, F, or S
<220> FEATURE:
<221> NAME/KEY: misc_feature
<222> LOCATION: (285)..(285)
<223> OTHER INFORMATION: Xaa = K; Q; or a conservative substitution of
      K, or Q
<220> FEATURE:
<221> NAME/KEY: misc_feature
<222> LOCATION: (300)..(300)
<223> OTHER INFORMATION: Xaa = R; H; Q; or a conservative substitution
      of R, H, or Q
<220> FEATURE:
<221> NAME/KEY: misc_feature
<222> LOCATION: (301)..(301)
<223> OTHER INFORMATION: Xaa = E; V; a conservative substitution of E or
      V; or a nonconservative substitution of E or V
<220> FEATURE:
<221> NAME/KEY: misc_feature
<222> LOCATION: (304)..(304)
<223> OTHER INFORMATION: Xaa = N; K; or a conservative substitution of N
      or K
<220> FEATURE:
<221> NAME/KEY: misc_feature
<222> LOCATION: (305)..(305)
<223> OTHER INFORMATION: Xaa = D; V; N; or a conservative substitution of
      D, V, or N; or a nonconservative substitution of D, V, or N
<220> FEATURE:
<221> NAME/KEY: misc_feature
<222> LOCATION: (317)..(317)
<223> OTHER INFORMATION: Xaa = T; S; or a conservative substitution of T
      or S
<220> FEATURE:
<221> NAME/KEY: misc_feature
<222> LOCATION: (324)..(324)
<223> OTHER INFORMATION: Xaa = G; V; D; a conservative substitution of
      G, V, or D; or a nonconservative substitution of G, V, or D
<220> FEATURE:
<221> NAME/KEY: misc_feature
<222> LOCATION: (326)..(326)
<223> OTHER INFORMATION: Xaa = A; V; or a conservative substitution of
      A or V
<220> FEATURE:
<221> NAME/KEY: misc_feature
<222> LOCATION: (327)..(327)
<223> OTHER INFORMATION: Xaa = S; T; or a conservative substitution of S
      or T
<220> FEATURE:
<221> NAME/KEY: misc_feature
<222> LOCATION: (328)..(328)
<223> OTHER INFORMATION: Xaa = G; S; A; or a conservative substitution
      of G, S, or A
<220> FEATURE:
<221> NAME/KEY: misc_feature
<222> LOCATION: (329)..(329)
<223> OTHER INFORMATION: Xaa = G; R; a conservative or substitution of G
      or R; or a nonconservative substitution of G or R
<220> FEATURE:
<221> NAME/KEY: misc_feature
<222> LOCATION: (331)..(331)
<223> OTHER INFORMATION: Xaa = H; L; a conservative or substitution of H
      or L; or a nonconservative substitution of H or L
<220> FEATURE:
<221> NAME/KEY: misc_feature
<222> LOCATION: (339)..(339)
<223> OTHER INFORMATION: Xaa = D; N; or a conservative substitution of D
      or N
```

```
<220> FEATURE:
<221> NAME/KEY: misc_feature
<222> LOCATION: (349)..(349)
<223> OTHER INFORMATION: Xaa = A; S; or a conservative substitution of A
     or S
<220> FEATURE:
<221> NAME/KEY: misc_feature
<222> LOCATION: (350)..(350)
<223> OTHER INFORMATION: Xaa = K; R; or a conservative substitution of K
     or R
<220> FEATURE:
<221> NAME/KEY: misc_feature
<222> LOCATION: (352)..(352)
<223> OTHER INFORMATION: Xaa = S; A; or a conservative substitution of S
     or A
<220> FEATURE:
<221> NAME/KEY: misc_feature
<222> LOCATION: (353)..(353)
<223> OTHER INFORMATION: Xaa = M; T; A; a conservative substitution of
     M, T, or A, or a nonconservative substitution of M, T, or A
<220> FEATURE:
<221> NAME/KEY: misc_feature
<222> LOCATION: (355)..(355)
<223> OTHER INFORMATION: Xaa = D; N; or a conservative substitution of D
     or N
<220> FEATURE:
<221> NAME/KEY: misc_feature
<222> LOCATION: (357)..(357)
<223> OTHER INFORMATION: Xaa = K; S; or a conservative substitution of K
     or S
<220> FEATURE:
<221> NAME/KEY: misc_feature
<222> LOCATION: (366)..(366)
<223> OTHER INFORMATION: Xaa = K; E; or a conservative substitution of K
     or E
<220> FEATURE:
<221> NAME/KEY: misc_feature
<222> LOCATION: (381)..(381)
<223> OTHER INFORMATION: Xaa = F; S; a conservative substitution of F or
     S; or a nonconservative substitution of F or S
<220> FEATURE:
<221> NAME/KEY: misc_feature
<222> LOCATION: (389)..(389)
<223> OTHER INFORMATION: Xaa = V; A; or a conservative substitution of V
     or A
<220> FEATURE:
<221> NAME/KEY: misc_feature
<222> LOCATION: (391)..(391)
<223> OTHER INFORMATION: Xaa = N; D; or a conservative substitution of N
     or D
<220> FEATURE:
<221> NAME/KEY: misc_feature
<222> LOCATION: (394)..(394)
<223> OTHER INFORMATION: Xaa = I; L; V; or a conservative substitution
     of I, L, or V
<220> FEATURE:
<221> NAME/KEY: misc_feature
<222> LOCATION: (412)..(412)
<223> OTHER INFORMATION: Xaa = T; S; or a conservative substitution of T
     or S
<220> FEATURE:
<221> NAME/KEY: misc_feature
<222> LOCATION: (413)..(413)
<223> OTHER INFORMATION: Xaa = T; M; P; a conservative substitution of
     T, M, or P; or a nonconservative substitution of T, M, or P
<220> FEATURE:
<221> NAME/KEY: misc_feature
<222> LOCATION: (414)..(414)
<223> OTHER INFORMATION: Xaa = V; a conservative substitution of V, a
     nonconservative substitution of V; or absent
<220> FEATURE:
<221> NAME/KEY: misc_feature
<222> LOCATION: (415)..(415)
<223> OTHER INFORMATION: Xaa = K; a conservative substitution of K; a
     nonconservative substitution of K; or absent
<220> FEATURE:
<221> NAME/KEY: misc_feature
<222> LOCATION: (416)..(416)
<223> OTHER INFORMATION: Xaa = N; K; or a conservative substitution of N
``` or K
<220> FEATURE:
<221> NAME/KEY: misc_feature
<222> LOCATION: (429)..(429)
<223> OTHER INFORMATION: Xaa = K; E; or a conservative substitution of K
    or E
<220> FEATURE:
<221> NAME/KEY: misc_feature
<222> LOCATION: (432)..(432)
<223> OTHER INFORMATION: Xaa = M; V; or a conservative substitution of M
    or V
<220> FEATURE:
<221> NAME/KEY: misc_feature
<222> LOCATION: (433)..(433)
<223> OTHER INFORMATION: Xaa = E; D; or a conservative substitution of E
    or D
<220> FEATURE:
<221> NAME/KEY: misc_feature
<222> LOCATION: (436)..(436)
<223> OTHER INFORMATION: Xaa = D; A; a conservative substitution of D or
    A, or a nonconservative substitution of D or A

<400> SEQUENCE: 7

Met Xaa Xaa Xaa Xaa Ile Thr Val Thr Arg Lys Ser Gln Ser Phe Val
1               5                   10                  15

Val Pro Xaa Ser Xaa Xaa Xaa Xaa Xaa Xaa Xaa Xaa Xaa Thr Leu
            20                  25                  30

Glu Leu Ser Xaa Ile Asp Arg Val Pro Gly Leu Arg His Thr Val Arg
            35                  40                  45

Ser Leu His Val Phe Arg Xaa Lys Xaa Xaa Xaa Xaa Xaa Xaa Xaa
    50                  55                  60

Xaa Xaa Xaa Xaa Xaa Xaa Xaa Xaa Arg Pro Xaa Glu Val Ile Arg Ala
65                  70                  75                  80

Ala Leu Ser Arg Ala Leu Val Asp Tyr Arg Pro Phe Ala Gly Arg Phe
                85                  90                  95

Val Gly Ser Xaa Xaa Ala Gly Glu Xaa Xaa Val Glu Cys Thr Asp Xaa
            100                 105                 110

Gly Ala Trp Phe Val Xaa Ala Val Xaa Asp Cys Ser Leu Xaa Xaa Val
            115                 120                 125

Asn Gly Leu Xaa Asp Tyr Pro Leu Met Val Ser Glu Glu Leu Leu
130                 135                 140

Pro Ala Pro Glu Glu Gly Val Asp Pro Thr Ser Ile Pro Xaa Met Met
145                 150                 155                 160

Gln Val Thr Glu Phe Xaa Cys Gly Gly Phe Val Val Gly Leu Val Ala
                165                 170                 175

Val His Thr Leu Ala Asp Gly Leu Gly Ala Ala Gln Phe Ile Asn Ala
            180                 185                 190

Ile Ser Glu Phe Ala Arg Gly Xaa Xaa Lys Xaa Thr Xaa Ala Pro Xaa
            195                 200                 205

Trp Ala Arg Xaa Leu Ile Pro Asn Pro Pro Lys Xaa Xaa Pro Xaa Xaa
210                 215                 220

Pro Pro Ser Phe Xaa Xaa Phe Gly Phe Xaa His Phe Xaa Xaa Asp Val
225                 230                 235                 240

Xaa Xaa Xaa Xaa Ile Ala Xaa Val Lys Xaa Xaa Tyr Xaa Gln Xaa Xaa
                245                 250                 255

Gly Xaa Tyr Cys Ser Thr Phe Asp Val Ala Ile Ala Lys Val Trp Gln
        260                 265                 270

Ala Arg Thr Xaa Ala Ile Lys Tyr Xaa Xaa Xaa Xaa Val His Val
            275                 280                 285

Cys Phe Phe Ala Asn Thr Arg His Leu Leu Thr Xaa Xaa Leu Pro Xaa

```
            290                 295                 300
Xaa Gly Gly Phe Tyr Gly Asn Cys Phe Tyr Pro Val Xaa Val Thr Ala
305                 310                 315                 320

Thr Ala Glu Xaa Val Xaa Xaa Xaa Xaa Leu Xaa Asp Val Ile Arg Met
                325                 330                 335

Ile Arg Xaa Gly Lys Ala Arg Leu Pro Leu Glu Phe Xaa Xaa Trp Xaa
            340                 345                 350

Xaa Gly Xaa Val Xaa Val Asp Pro Tyr Gln Leu Thr Phe Xaa His Asn
            355                 360                 365

Val Leu Phe Val Ser Asp Trp Thr Arg Leu Gly Phe Xaa Glu Val Asp
370                 375                 380

Tyr Gly Trp Gly Xaa Pro Xaa His Ile Xaa Pro Phe Thr Tyr Ala Asp
385                 390                 395                 400

Tyr Met Ala Val Ala Val Leu Gly Ala Pro Pro Xaa Xaa Xaa Xaa Xaa
                405                 410                 415

Lys Gly Thr Arg Ile Met Thr Gln Cys Val Glu Glu Xaa His Leu Xaa
            420                 425                 430

Xaa Phe Lys Xaa Glu Met Lys Ala Phe Phe
            435                 440

<210> SEQ ID NO 8
<211> LENGTH: 2951
<212> TYPE: DNA
<213> ORGANISM: Artificial Sequence
<220> FEATURE:
<223> OTHER INFORMATION: C4H Promoter

<400> SEQUENCE: 8
aagcttagag gagaaactga gaaaatcagc gtaatgagag acgagagcaa tgtgctaaga      60
gaagagattg ggaagagaga agagacgata aaggaaacgg aaaagcatat ggaggagctt     120
catatggagc aagtgaggct gagaagacgg tcgagtgagc ttacggaaga agtggaaagg     180
acgagagtgt ctgcatcgga aatggctgag cagaaaagag aagctataag acagctttgt     240
atgtctcttg accattacag agatgggtac gacaggcttt ggagagttgt tgccggccat     300
aagagtaaga gagtagtggt tttaacaact tgaagtgtaa gaacaatgag tcaatgacta     360
cgtgcaggac attggacata ccgtgtgttc ttttggattg aaatgttgtt tcgaagggct     420
gttagttgat gttgaaaata ggttgaagtt gaataatgca tgttgatata gtaaatatca     480
atggtaatat tttctcattt cccaaaactc aaatgatatc atttaattat aaactaacgt     540
aaactgttga caatacactt atggttaaaa atttggagtc ttgttttagt atacgtatca     600
ccaccgcacg gtttcaaaac cacataattg taaatgttat tggaaaaaag aacccgcaat     660
acgtattgta ttttggtaaa catagctcta agcctctaat atataagctc tcaacaattc     720
tggctaatgg tcccaagtaa gaaaagccca tgtattgtaa ggtcatgatc tcaaaaacga     780
gggtgaggtg gaatactaac atgaggagaa agtaaggtga caaattttg gggcaatagt     840
ggtggatatg gtggggaggt aggtagcatc atttctccaa gtcgctgtct ttcgtggtaa     900
tggtaggtgt gtctctcttt atattattta ttactactca ttgttaattt ctttttttct     960
acaatttgtt tcttactcca aaatacgtca caaatataat actaggcaaa taattattta    1020
attgtaagtc aatagagtgg ttgttgtaaa attgattttt gatattgaaa gagttcatgg    1080
acggatgtgt atgcgccaaa tgctaagccc ttgtagtctt gtactgtgcc gcgcgtatat    1140
tttaaccacc actagttgtt tctctttttc aaaaacacac aaaaaataat tgttttcgt     1200
```

-continued

```
aacggcgtca aatctgacgg cgtctcaata cgttcaattt tttctttctt tcacatggtt    1260
tctcatagct ttgcattgac cataggtaaa gggataagga taaaggtttt ttctcttgtt    1320
tgttttatcc ttattattca aaatggataa aaaaacagtc ttattttgat ttctttgatt    1380
aaaaaagtca ttgaaattca tatttgattt tttgctaaat gtcaactcag agacacaaac    1440
gtaatgcact gtcgccaata ttcatggatc atgaccatga atatcactag aataattgaa    1500
aatcagtaaa atgcaaacaa agcatttcct aattaaaaca gtcttctaca ttcacttaat    1560
tggaatttcc tttatcaaac ccaaagtcca aaacaatcgg caatgttttg caaaatgttc    1620
aaaactattg gcgggttggt ctatccgaat tgaagatctt ttctccatat gatagaccaa    1680
cgaaattcgg catacgtgtt ttttttttg ttttgaaaac cctttaaaca accttaattc    1740
aaaatactaa tgtaaccttta ttgaacgtgc atctaaaaat tttgaacttt gcttttgaga    1800
aataatcaat gtaccaataa agaagatgta gtacatacat tataattaaa tacaaaaaag    1860
gaatcaccat atagtacatg gtagacaatg aaaaacttta aaacatatac aatcaataat    1920
actctttgtg cataactttt tttgtcgtct cgagtttata tttgagtact tatacaaact    1980
attagattac aaactgtgct cagatacatt aagttaatct tatatacaag agcactcgag    2040
tgttgtcctt aagttaatct taagatatct tgaggtaaat agaaatagtt aactcgtttt    2100
tattttcttt tttttaccat gagcaaaaaa agatgaagta agttcaaaac gtgacgaatc    2160
tacatgttac tacttagtat gtgtcaatca ttaaatcggg aaaacttcat catttcagga    2220
gtactacaaa actcctaaga gtgagaacga ctacatagta catattttga taaaagactt    2280
gaaaacttgc taaaacgaat ttgcgaaaat ataatcatac aagtagaacc actgatttga    2340
tcgaattatt catagctttg taggatgaac ttaactaaat aatatctcac aaaagtattg    2400
acagtaaacct agtactatac tatctatgtt agaatatgat tatgatataa tttatcccct    2460
cacttattca tatgattttt gaagcaacta ctttcgtttt tttaacattt tcttttttgg    2520
tttttgttaa tgaacatatt tagtcgtttc ttaattccac tcaaatagaa aatcaaaga    2580
gaactttatt taatagatat gaacataatc tcacatcctc ctcctacctt caccaaacac    2640
ttttacatac actttgtggt ctttctttac ctaccaccat caacaacaac accaagcccc    2700
actcacacac acgcaatcac gttaaatcta acgccgttta ttatctcatc attcaccaac    2760
tcccacgtac ctaacgccgt ttacctttttg ccgttggtcc tcatttctca aaccaaccaa    2820
acctctccct cttataaaat cctctctccc ttctttattt cttcctcagc agcttcttct    2880
gctttcaatt actctcgccg acgattttct caccggaaaa aaacaatatc attgcggata    2940
cacaaactat a                                                         2951
```

<210> SEQ ID NO 9
<211> LENGTH: 1329
<212> TYPE: DNA
<213> ORGANISM: Brachypodium distachyon

<400> SEQUENCE: 9

```
atggcagaaa tctgcaccgt gaacaggaag tcccagtcct tcgtcaagcc ggccgcgcca      60
acgccaacgc ctcagacgcc gccgccgctg ctggagctgt cggccatcga ccgcgtgccc     120
gggctgcgcc acaccgtgcg ctctctccac gtcttccgcc cgccgccgca cggcgacggc     180
gccgcctgca gcaggccggc cgaggtgatc cgcgccgcgc tggcccgcgc gctcgtggag     240
tacccccgcgt cgccgggcg gctcgtcgtc ggcggctccg ctcggactg cggcgtggcg     300
tgcaccggcg acggagcgtg gttcgttgaa gcggccgccg gctgtaacct ggaggacgtg     360
```

```
aacgagctgg actaccctct cgtggtctgc gaggaggagc tgctccccac cgcccctgag    420
ggagagctgg atcctacaag cattccggtc atgatgcagg tgaccgaatt cagctgcgga    480
ggatttgtgg tgggcctggt agcagtccac accttcgcag acgggctcgg cgcggcccaa    540
ttcatcaacg ccatcgccga attcgcccgt ggcctaaaca ggcccacagt gaatcccata    600
tgggcccgag ccacaatccc caacccgccc aaattccctc ccggcccacc accatccttc    660
caatccttcg gcttccagca tttcgccacg gacatccgtc cagaccgcat cgcccacgcc    720
aaagccgagt acctcaaggc cacgggcacc cactgctcgg ccttcgacgt cgccgtggcc    780
aaggtctggc aggcccgaac ccgggccgta aggtacggcc cagaggccca ggtgcaggtc    840
tgcttcttcg ccaacacgag gcaccttctc ggagagcttc tccccgaagg tttctacggc    900
aactgcttct tcccggtcac cgtgaaggcc agagctgggg atgttgccgg cagcaaggat    960
ttacttggta ttatccggat gatcagggac gggaaggcca ggctgccttt ggagttcgcc   1020
gattgggcgt caggtttagg aggaggaggg gctggggata agatgaagtt tgtgcaggat   1080
gatccttatg agctgaggtt tgagcataat gtgttgtttg tgtcggattg gacgaggctt   1140
gggttcttgg aggtggacta tggctggggc gtgcctagcc atgttatacc tttcaattat   1200
gcggactaca tggcggtcgc ggtgctcggt gctccgccgg cgccggtgaa ggggactcgg   1260
gtcatgacgc agtgcgtgga ggagaagcat cttaaggagt tcagggatga gatggaaggc   1320
tccttttag                                                          1329

<210> SEQ ID NO 10
<211> LENGTH: 442
<212> TYPE: PRT
<213> ORGANISM: Brachypodium distachyon

<400> SEQUENCE: 10

Met Ala Glu Ile Cys Thr Val Asn Arg Lys Ser Gln Ser Phe Val Lys
1               5                   10                  15

Pro Ala Ala Pro Thr Pro Thr Pro Gln Thr Pro Pro Leu Leu Glu
            20                  25                  30

Leu Ser Ala Ile Asp Arg Val Pro Gly Leu Arg His Thr Val Arg Ser
        35                  40                  45

Leu His Val Phe Arg Pro Pro His Gly Asp Gly Ala Ala Cys Ser
    50                  55                  60

Arg Pro Ala Glu Val Ile Arg Ala Ala Leu Ala Arg Ala Leu Val Glu
65                  70                  75                  80

Tyr Pro Ala Phe Ala Gly Arg Leu Val Val Gly Ser Gly Ser Asp
                85                  90                  95

Cys Gly Val Ala Cys Thr Gly Asp Gly Ala Trp Phe Val Glu Ala Ala
            100                 105                 110

Ala Gly Cys Asn Leu Glu Asp Val Asn Glu Leu Asp Tyr Pro Leu Val
        115                 120                 125

Val Cys Glu Glu Glu Leu Leu Pro Thr Ala Pro Glu Gly Glu Leu Asp
    130                 135                 140

Pro Thr Ser Ile Pro Val Met Met Gln Val Thr Glu Phe Ser Cys Gly
145                 150                 155                 160

Gly Phe Val Val Gly Leu Val Ala Val His Thr Phe Ala Asp Gly Leu
                165                 170                 175

Gly Ala Ala Gln Phe Ile Asn Ala Ile Ala Glu Phe Ala Arg Gly Leu
            180                 185                 190
```

-continued

```
Asn Arg Pro Thr Val Asn Pro Ile Trp Ala Arg Ala Thr Ile Pro Asn
            195                 200                 205
Pro Pro Lys Phe Pro Pro Gly Pro Pro Ser Phe Gln Ser Phe Gly
    210                 215                 220
Phe Gln His Phe Ala Thr Asp Ile Arg Pro Asp Arg Ile Ala His Ala
225                 230                 235                 240
Lys Ala Glu Tyr Leu Lys Ala Thr Gly Thr His Cys Ser Ala Phe Asp
                245                 250                 255
Val Ala Val Ala Lys Val Trp Gln Ala Arg Thr Arg Ala Val Arg Tyr
            260                 265                 270
Gly Pro Glu Ala Gln Val Gln Val Cys Phe Ala Asn Thr Arg His
    275                 280                 285
Leu Leu Gly Glu Leu Leu Pro Glu Gly Phe Tyr Gly Asn Cys Phe Phe
290                 295                 300
Pro Val Thr Val Lys Ala Arg Ala Gly Asp Val Ala Gly Ser Lys Asp
305                 310                 315                 320
Leu Leu Gly Ile Ile Arg Met Ile Arg Asp Gly Lys Ala Arg Leu Pro
                325                 330                 335
Leu Glu Phe Ala Asp Trp Ala Ser Gly Leu Gly Gly Gly Ala Gly
            340                 345                 350
Asp Lys Met Lys Phe Val Gln Asp Pro Tyr Glu Leu Arg Phe Glu
    355                 360                 365
His Asn Val Leu Phe Val Ser Asp Trp Thr Arg Leu Gly Phe Leu Glu
    370                 375                 380
Val Asp Tyr Gly Trp Gly Val Pro Ser His Val Ile Pro Phe Asn Tyr
385                 390                 395                 400
Ala Asp Tyr Met Ala Val Ala Val Leu Gly Ala Pro Pro Ala Pro Val
                405                 410                 415
Lys Gly Thr Arg Val Met Thr Gln Cys Val Glu Glu Lys His Leu Lys
            420                 425                 430
Glu Phe Arg Asp Glu Met Glu Gly Ser Phe
    435                 440

<210> SEQ ID NO 11
<211> LENGTH: 24
<212> TYPE: DNA
<213> ORGANISM: Artificial Sequence
<220> FEATURE:
<223> OTHER INFORMATION: Actin2-F Promoter

<400> SEQUENCE: 11
ccagaaggat gcatatgttg gtga                                              24

<210> SEQ ID NO 12
<211> LENGTH: 20
<212> TYPE: DNA
<213> ORGANISM: Artificial Sequence
<220> FEATURE:
<223> OTHER INFORMATION: Actin2-R Promoter

<400> SEQUENCE: 12
gaggagcctc ggtaagaaga                                                   20

<210> SEQ ID NO 13
<211> LENGTH: 15
<212> TYPE: DNA
<213> ORGANISM: Artificial Sequence
<220> FEATURE:
<223> OTHER INFORMATION: ZmFMT-F Promoter
```

```
<400> SEQUENCE: 13
atggcgagca tcacc                                                    15

<210> SEQ ID NO 14
<211> LENGTH: 21
<212> TYPE: DNA
<213> ORGANISM: Artificial Sequence
<220> FEATURE:
<223> OTHER INFORMATION: ZmFMT-R Promoter

<400> SEQUENCE: 14
agcaaagaag gctttcatct c                                             21

<210> SEQ ID NO 15
<211> LENGTH: 15
<212> TYPE: DNA
<213> ORGANISM: Artificial Sequence
<220> FEATURE:
<223> OTHER INFORMATION: SbFMT-F Promoter

<400> SEQUENCE: 15
atggcgacga ccatc                                                    15

<210> SEQ ID NO 16
<211> LENGTH: 17
<212> TYPE: DNA
<213> ORGANISM: Artificial Sequence
<220> FEATURE:
<223> OTHER INFORMATION: SbFMT-R Promoter

<400> SEQUENCE: 16
agcaaagaag gccttca                                                  17

<210> SEQ ID NO 17
<211> LENGTH: 18
<212> TYPE: DNA
<213> ORGANISM: Artificial Sequence
<220> FEATURE:
<223> OTHER INFORMATION: PvFMT-F Promoter

<400> SEQUENCE: 17
atggtgaaca tcaccgtg                                                 18

<210> SEQ ID NO 18
<211> LENGTH: 18
<212> TYPE: DNA
<213> ORGANISM: Artificial Sequence
<220> FEATURE:
<223> OTHER INFORMATION: PvFMT-R Promoter

<400> SEQUENCE: 18
agcaaagaag gccttcat                                                 18
```